US010053731B2

(12) United States Patent
Blainey et al.

(10) Patent No.: US 10,053,731 B2
(45) Date of Patent: Aug. 21, 2018

(54) SIEVE VALVES, MICROFLUIDIC CIRCUITS, MICROFLUIDIC DEVICES, KITS, AND METHODS FOR ISOLATING AN ANALYTE

(71) Applicants: THE BROAD INSTITUTE, INC., Cambridge, MA (US); MASSACHUSETTS INSTITUTE OF TECHNOLOGY, Cambridge, MA (US); Paul Blainey, Cambridge, MA (US); Soohong Kim, Cambridge, MA (US)

(72) Inventors: Paul Blainey, Cambridge, MA (US); Soohong Kim, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/696,469

(22) Filed: Sep. 6, 2017

(65) Prior Publication Data
US 2018/0016633 A1    Jan. 18, 2018

Related U.S. Application Data

(60) Division of application No. 15/087,684, filed on Mar. 31, 2016, now Pat. No. 9,790,549, which is a
(Continued)

(51) Int. Cl.
*B01L 3/00* (2006.01)
*C12Q 1/6874* (2018.01)
(Continued)

(52) U.S. Cl.
CPC .......... *C12Q 1/6874* (2013.01); *B01D 35/02* (2013.01); *B01L 3/502715* (2013.01);
(Continued)

(58) Field of Classification Search
None
See application file for complete search history.

(56) References Cited

U.S. PATENT DOCUMENTS 6,793,753 B2   9/2004 Unger
6,899,137 B2   5/2005 Unger
(Continued)

FOREIGN PATENT DOCUMENTS

WO        2006071470 A2    7/2006
WO    WO 2009039246 A2    3/2009
WO        2012097450 A1    7/2012

OTHER PUBLICATIONS

Au, A. K., et al., "Microvalves and Micropumps for BioMEMS", Micromachines 2, 179-220, 2011.
(Continued)

*Primary Examiner* — Rebecca L Martinez
(74) *Attorney, Agent, or Firm* — Melissa Hunter-Ensor; Leslie Serunian; Greenberg Traurig, LLP

(57) ABSTRACT

The invention generally provides a sieve valve including: a substrate defining a channel; a flexible membrane adapted and configured for deployment at an intersection with the channel; and one or more protrusions extending into the channel from the substrate or the flexible membrane. The one or more protrusions define a plurality of recesses extending beyond the intersection between the channel and the flexible membrane;

A microfluidic circuit including one or more sieve valves. In particular embodiments, the circuit comprises one or more input/output valves. The one or one or more input/output valves can include one or more input valves and one or more output valves.

(Continued)

The microfluidic circuit can further include a mixing circuit. At least one of the sieve valves can be positioned between the one or more input/output valves and the mixing circuit. The invention further provides methods of using the device for the analysis of samples comprising cells.

19 Claims, 80 Drawing Sheets

Related U.S. Application Data continuation-in-part of application No. PCT/US2014/058637, filed on Oct. 1, 2014.

(60) Provisional application No. 61/885,257, filed on Oct. 1, 2013, provisional application No. 61/940,324, filed on Feb. 14, 2014, provisional application No. 62/043,330, filed on Aug. 28, 2014.

(51) Int. Cl.
| | |
|---|---|
| *B01D 35/02* | (2006.01) |
| *B01L 7/00* | (2006.01) |
| *C12N 15/10* | (2006.01) |
| *C12Q 1/6806* | (2018.01) |
| *F16K 99/00* | (2006.01) |

(52) U.S. Cl.
CPC ... *B01L 3/502738* (2013.01); *B01L 3/502753* (2013.01); *B01L 3/502761* (2013.01); *B01L 7/52* (2013.01); *C12N 15/1006* (2013.01); *C12Q 1/6806* (2013.01); *F16K 99/0015* (2013.01); *F16K 99/0026* (2013.01); *F16K 99/0059* (2013.01); *B01L 3/502707* (2013.01); *B01L 7/525* (2013.01); *B01L 2200/0668* (2013.01); *B01L 2200/10* (2013.01); *B01L 2300/021* (2013.01); *B01L 2300/0663* (2013.01); *B01L 2300/0861* (2013.01); *B01L 2300/0867* (2013.01); *B01L 2300/0887* (2013.01); *B01L 2300/123* (2013.01); *B01L 2400/0409* (2013.01); *B01L 2400/0487* (2013.01); *B01L 2400/06* (2013.01); *B01L 2400/0622* (2013.01); *B01L 2400/0655* (2013.01); *F16K 2099/008* (2013.01); *F16K 2099/0074* (2013.01); *F16K 2099/0084* (2013.01)

(56) References Cited

U.S. PATENT DOCUMENTS

| | | | |
|---|---|---|---|
| 6,929,030 | B2 | 8/2005 | Unger |
| 7,040,338 | B2 | 5/2006 | Unger |
| 7,052,545 | B2 | 5/2006 | Quake |
| 7,144,616 | B1 | 12/2006 | Unger |
| 7,169,314 | B2 | 1/2007 | Unger |
| 7,216,671 | B2 | 5/2007 | Unger |
| 7,250,128 | B2 | 7/2007 | Unger |
| 8,075,851 | B2 | 12/2011 | Elizarov et al. |
| 8,206,593 | B2 | 6/2012 | Lee |
| 2001/0033796 | A1 | 10/2001 | Unger |
| 2001/0054778 | A1 | 12/2001 | Unger |
| 2002/0029814 | A1 | 3/2002 | Unger |
| 2002/0144738 | A1 | 10/2002 | Unger |
| 2002/0145231 | A1 | 10/2002 | Quake |
| 2003/0019833 | A1 | 1/2003 | Unger |
| 2003/0206806 | A1 | 11/2003 | Paul et al. |
| 2005/0112882 | A1 | 5/2005 | Unger |
| 2005/0166980 | A1 | 8/2005 | Unger |
| 2005/0226742 | A1 | 10/2005 | Unger |
| 2006/0006065 | A1 | 1/2006 | Pinkas et al. |
| 2006/0054228 | A1 | 3/2006 | Unger |
| 2007/0059494 | A1 | 3/2007 | Unger |
| 2007/0281309 | A1 | 12/2007 | Kong |
| 2008/0173365 | A1 | 7/2008 | Unger |
| 2008/0210319 | A1 | 9/2008 | Unger |
| 2008/0210320 | A1 | 9/2008 | Unger |
| 2008/0210321 | A1 | 9/2008 | Unger |
| 2008/0210322 | A1 | 9/2008 | Unger |
| 2008/0220216 | A1 | 9/2008 | Unger |
| 2008/0236669 | A1 | 10/2008 | Unger |
| 2008/0277005 | A1 | 11/2008 | Unger |
| 2008/0277007 | A1 | 11/2008 | Unger |
| 2008/0277494 | A1 | 11/2008 | Davies et al. |
| 2009/0215125 | A1 | 8/2009 | Reed |
| 2011/0030808 | A1 | 2/2011 | Chiou |
| 2012/0061305 | A1 | 3/2012 | Quake et al. |
| 2012/0125444 | A1 | 5/2012 | Tipler |
| 2013/0139899 | A1 | 6/2013 | Galas et al. |
| 2014/0041727 | A1 | 2/2014 | Hansen |
| 2014/0065653 | A1 | 3/2014 | Maerkl |

OTHER PUBLICATIONS

Beattie, W., "Rare Cell Separation Using Resettable Cell Traps", Thesis in Partial Fulfillment of Requirements for the Degree of Master of Applied Science, The University of British Columbia, Aug. 2013.

Burkert Global, "Hygienic Process Applications / Reverse and By-Pass flow for columns and filters", http://www.burkert.com/COM/2844.htm, 2014.

Gerhardt, T., "Chromatographic Cell Separation based on Size and Rigidity using Dynamic Microstructures", Thesis submitted in partial fulfillment of the requirements for the Degree of Master of Applied Science, The University of British Columbia, Jun. 2010.

Grabowski, M., et al., "Valve Concepts for Microfluidic Cell Handling", Acta Polytechnica vol. 50 No. 4, 41-47, 2010.

Harvard, "SU-8 Photolithography Process", CNS Standard Operating Procedure—SOP031, Aug. 1-5, 2008.

Huft, J., et al., Fabrication of High-Quality Microfluidic Solid-Phase Chromatography Columns, Analytical Chemistry, 85, 1797-1802, 2013.

Melin, J., et al., "Microfluidic Large-Scale Integration: The Evolution of Design Rules for Biological Automation", Annu. Rev. Biophys. Biolmol. Struct. 36:213-231, 2007.

Micro.Chem, NANOtm SU-8 2000, Negative Tone Photoresist Formulations 2002-2025, 2000.

Tan, S. J., et al., "A Microfluidic Device for Preparing Next Generation DNA Sequencing Libraries and for Automating Other Laboratory Protocols That Require One or More Column Chromatography Steps", Microfluidic Automation of NGS Library Preparation, PLOS ONE, vol. 8, Issue 7, Jul. 2013.

International Search Report and Written Opinion, for corresponding PCT/US2014/058637, dated Mar. 3, 2015 (12 pages).

PCT International Search Report and Written Opinion issued in International Application No. PCT/US2016/019606 dated Jul. 26, 2016 (14 pages).

Supplementary Partial European Search Report, dated Mar. 23, 2017, received in corresponding European patent application No. 14850347.7, (7 pages).

Extended European Search Report, dated Aug. 8, 2017, received in corresponding European patent application No. 14850347.7, (12 pages).

400

402 loading a cell into a holding chamber of a microfluidic device, wherein the holding chamber is coupled to an input port of a mixing circuit

404 loading a capture substrate configured to capture a nucleic acid into the holding chamber

406 passing the cell and the capture substrate into the mixing circuit, wherein the mixing circuit comprises a plurality of chambers, and the mixing circuit has a height that is substantially the same along the entire mixing circuit

408 lysing the cell to release components of the cell

410 capturing a target component of the cell on the capture substrate

412 washing the capture substrate to remove uncaptured components

414 releasing the target component from the capture substrate

FIG. 4

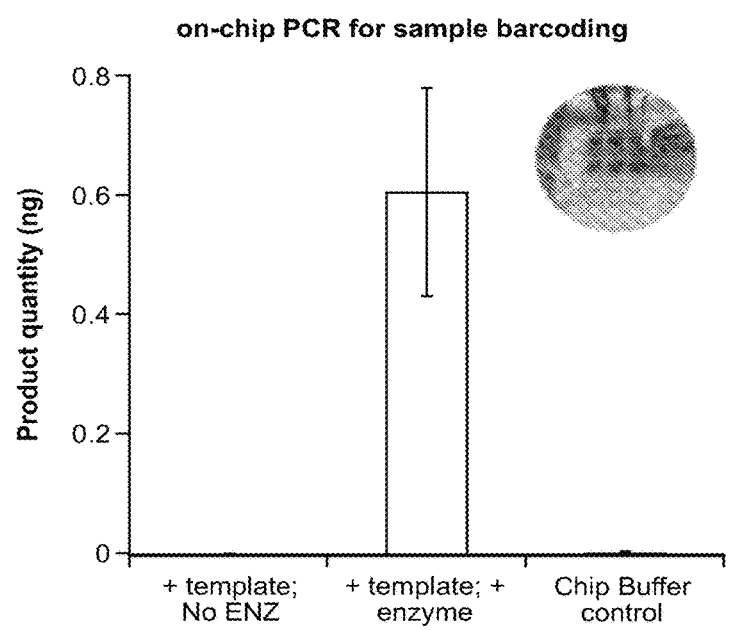
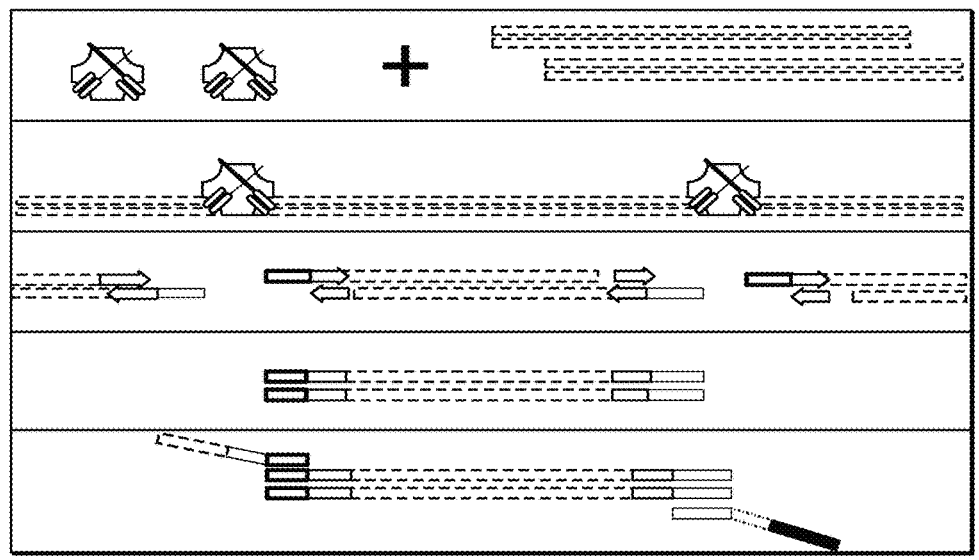
proof of concept in 40 nL reactor design
once barcoded, the samples can be pooled
FIG. 29

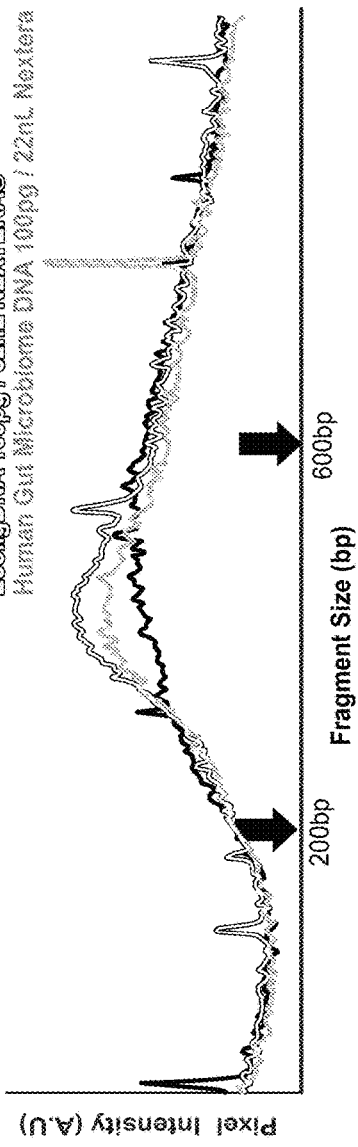
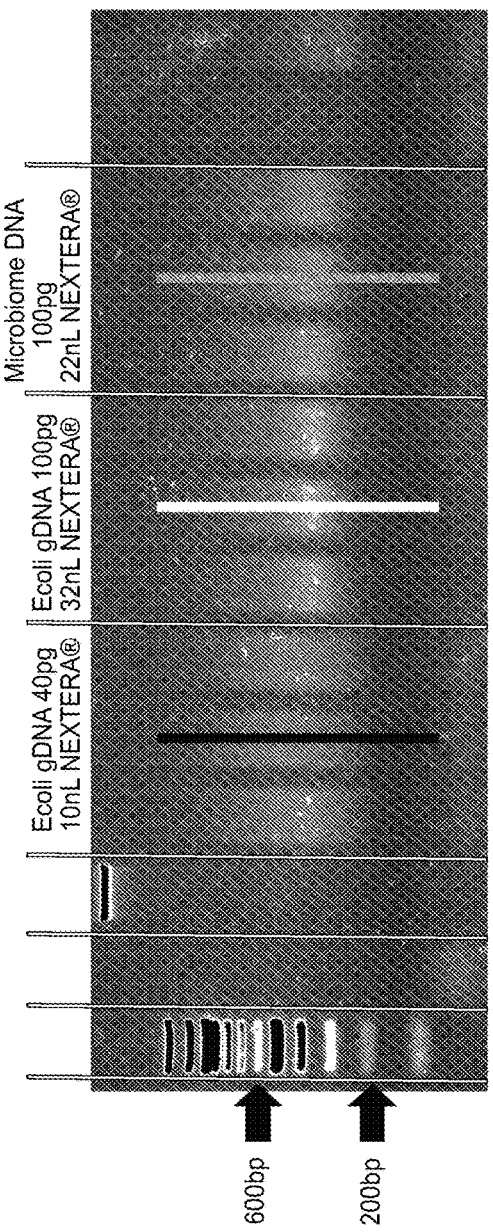
FIG. 42

0.1%
- Subdoligranulum:Subdoligranulum_variabile
- Lactobacillus:Lactobacillus_casei
- Holdemania:Holdemania_filiformis
- Anaerotruncus:Anaerotruncus_colihominis
- Slackia:Slackia_unclassified
- Eggerthella:Eggerthella_lenta
- Clostridium:Clostridium_bartlettii
- Bacteroides:Bacteroides_ovatus
- Bacteroides:Bacteroides_xylanisolvens
- Eubacterium:Eubacterium_ventriosum
- Roseburia:Roseburia_intestinalis
- Propionibacterium:Propionibacterium_freudenreichii
- Alistipes:Alistipes_shahii 0.25%
- Streptococcus:Streptococcus_thermophilus
- Bacteroides:Bacteroides_finegoldii
- Clostridium:Clostridium_leptum
- Blautia:Blautia_hydrogenotrophica
- Roseburia:Roseburia_inulinivorans
- Dorea:Dorea_formicigenerans
- Faecalibacterium:Faecalibacterium_cf
- Ruminococcus:Ruminococcus_gnavus
- Phascolarctobacterium:Phascolarctobacterium_unclassified
- Ruminococcus:Ruminococcus_torques
- Coprococcus:Coprococcus_catus
- Bifidobacterium:Bifidobacterium_longum
- Ruminococcus:Ruminococcus_obeum 1%
- Odoribacter:Odoribacter_splanchnicus
- Eubacterium:Eubacterium_hallii
- Bacteroides:Bacteroides_vulgatus
- Coprococcus:Coprococcus_comes
- Bacteroides:Bacteroides_caccae
- Parabacteroides:Parabacteroides_merdae
- Faecalibacterium:Faecalibacterium_prausnitzii
- Dorea:Dorea_longicatena
- Bifidobacterium:Bifidobacterium_bifidum
- Bifidobacterium:Bifidobacterium_adolescentis
- Collinsella:Collinsella_aerofaciens 10%
- Bacteroides:Bacteroides_stercoris
- Ruminococcus:Ruminococcus_bromii
- Bacteroides:Bacteroides_uniformis
- Eubacterium:Eubacterium_rectale
- Alistipes:Alistipes_putredinis
- Akkermansia:Akkermansia_muciniphila

FIG. 45B

Is $1 Sequencing Sample Prep Possible?

Assumptions

| | |
|---|---|
| # libraries/run | 128 |
| # runs/chip | 20 |
| # runs per day | 1 |
| chip controller cost | $ 5,000 per device |
| reagent utilization factor | 75% |
| equipment useful life | 3 years |

| Item | cost/unit | # libraries/unit | Direct cost/library |
|---|---|---|---|
| technician labor/hr | $ 50 | 128 | $ 0.39 |
| filter tip pipet tips | $ 0.10 | 0.5 | $ 0.20 |
| Tn5 transposase | $ 73 | 384 | $ 0.19 |
| microfluidic chip | $ 200 | 2,560 | $ 0.08 |
| chip controller | $ 5,000 | 96,000 | $ 0.05 |
| multi-channel pipet | $ 1,000 | 96,000 | $ 0.01 |
| buffers and PCR reagents | $ 1,000 | 128,000 | $ 0.01 |
| M-270 beads | $ 1,300 | 192,000 | $ 0.01 |
| 6 micron filler beads | $ 200 | 256,000 | $ 0.00 |
| | | Totals $ | 0.94 |

From Cells to Library

FIG. 50

$1 Sample prep possible – if labor is minimized by automation and reaction volumes are reduced by > 100 fold

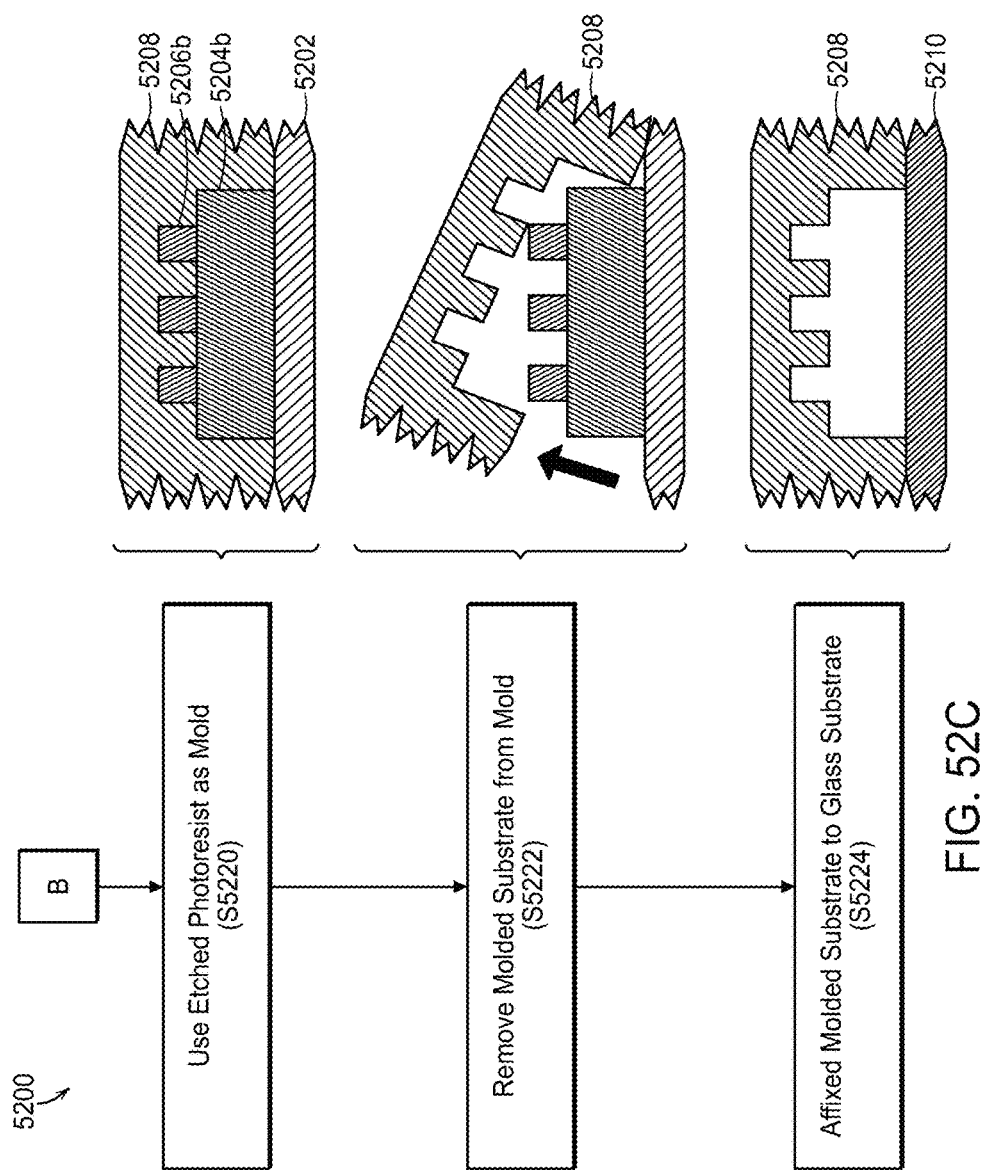

Fragment Diversity – pre-PCR

Starting DNA amount = 100 pg = 20000 Cells
Library Conversion Efficiency = $1e^{-3}$
E. coli Genomic DNA = $4.6e^6 bp$
Fragment size = 300bp
Tagmented library amount = $100e^{-12}g \times 1e{-3} \times 6.022e23/$ (MW of 300bp fragments) = $3e^5$ molecules Informational Complexity from 100 pgDNA Tagmented library amount/100pg DNA = $3e^5$ molecules
Fragment size = 300bp
E. coli Genomic DNA = $4.6e^6 bp$ $3e^5$ molecules x 300bp / $4.6e6bp$ = 20x (20 genome equivalence)

FIG. 62

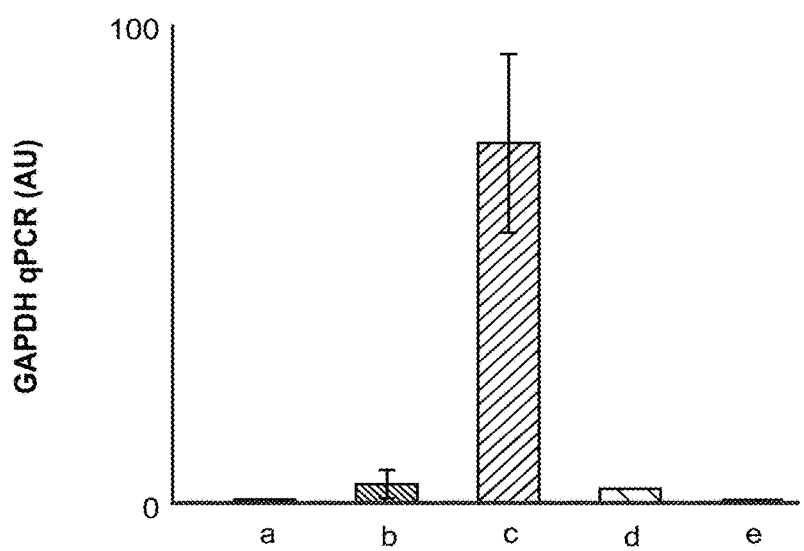

On-chip reverse transcription and cDNA conversion SmartSeq2 reagents. Validation of successful RT→cDNA was done by relatively quantifying the GAPDH gene present in the samples recovered from the chip after the RT/cDNA reaction using SmartSeq2 reagents. The histogram bars are; a) No RNA, b) RNA only, c) all reagents, d) chip wash buffer collected to measure washing efficiency of the reactor walls, f) water only control.

FIG. 64

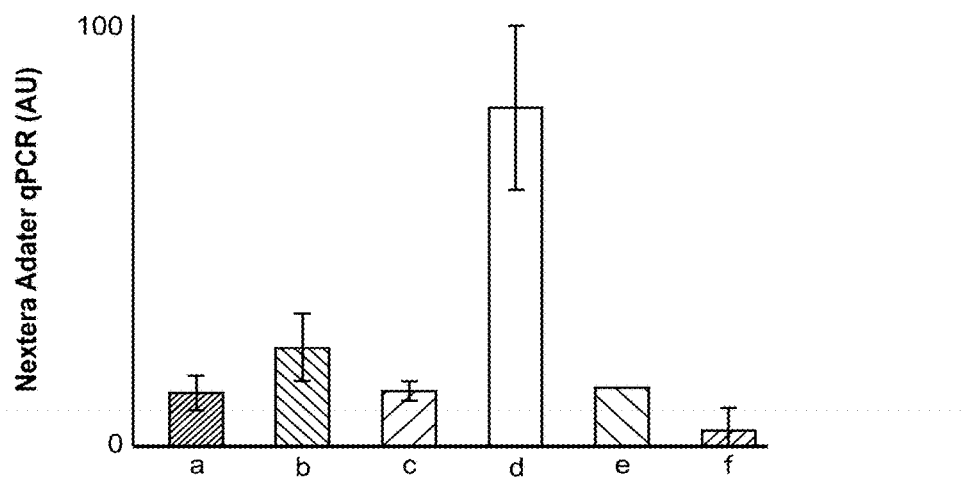

On-chip RNA-seq library construction with SmartSeq2 reagents.
Validation of successful RT→cDNA→library construction with NEXTERA®
on-chip was done by relatively quantifying the fragments that have the
NEXTERA® adapter sequence tagged. This quantification is done by performing
qPCR on the samples recovered from the device after the entire on-chip
SmartSeq2 reaction, with PCR primers against the adapter sequence.
The histogram bars are; a) RNA only, b) RNA only with NEXTERA® enzymes,
c) all reagents without NEXTERA® enzymes, d) all reagents with NEXTERA®
enzymes, e) chip wash buffer collected to measure washing efficiency
of the reactor walls, f) water only control.

FIG. 65

SIEVE VALVES, MICROFLUIDIC CIRCUITS, MICROFLUIDIC DEVICES, KITS, AND METHODS FOR ISOLATING AN ANALYTE

CROSS-REFERENCE TO RELATED APPLICATIONS

This application is a divisional of U.S. patent application Ser. No. 15/087,684, filed on Mar. 31, 2016, which is a continuation-in-part of International PCT Application No. PCT/US2014/058637, which was filed on Oct. 1, 2014 and which claims priority to U.S. Provisional Patent Application No. 61/885,257, filed on Oct. 1, 2013, U.S. Provisional Patent Application No. 61/940,324, filed on Feb. 14, 2014, and U.S. Provisional Patent Application No. 62/043,330, filed on Aug. 28, 2014. The entire contents of each of the foregoing applications are hereby incorporated by reference herein.

STATEMENT REGARDING GOVERNMENT SUPPORT

This invention was made with government support under Grant No. 1308852 awarded by the National Science Foundation. The government has certain rights in the invention.

BACKGROUND OF THE INVENTION

As genome sequencing and other cellular analytic techniques become more and more commonplace, interest in characterizing collections of cells has grown. For example, sequencing and characterizing microbial isolates, such as those from natural microbial systems or newly engineered microbes, would allow scientists to gain an understanding of the many different types of microbial ecology and phylogeny that exist. Similarly, analyzing many cells in a tissue sample would increase understanding of cellular diversity in the tissue. However, analysis of collections of cells has been difficult to perform on large scales due to the high costs associated with analytical processes. For example, sequencing processes require preparation of a nucleic acid "library" from each cell that is subsequently sequenced to analyze the associated genomic data. While sequencing costs have decreased over time, the cost of library preparation has remained relatively expensive.

Current solutions for single-cell analysis are expensive because they involve costly chemicals that are not efficiently utilized and multi-step processes that are carried out manually or through expensive liquid-handling robots.

SUMMARY OF THE INVENTION

One aspect of the invention provides a sieve valve including: a substrate defining a channel; a flexible membrane adapted and configured for deployment at an intersection with the channel; and one or more protrusions extending into the channel from the substrate or the flexible membrane. The one or more protrusions define a plurality of recesses extending beyond the intersection between the channel and the flexible membrane.

This aspect of the invention can have a variety of embodiments. The plurality of recesses can have a cross-sectional width of less than 50 µm. The plurality of recesses can have a cross-sectional width between about 5 µm and about 15 µm. The plurality of recesses can have a cross-sectional height between about 0.5 µm and about 10 µm. The plurality of recesses can have a cross-sectional height between about 3 µm and about 5 µm.

The substrate, the channel, the flexible membrane, and the one or more protrusions can be dimensioned such that when the flexible membrane is deployed using a pressure of between about 35 psi and about 45 psi, the flexible membrane will partially occlude the channel so that unoccluded portions of the channel have a combined cross-sectional area between about 100 $\mu m^2$ and about 400 $\mu m^2$.

The channel can have a substantially-rectangular profile. The channel can have a width selected from the group consisting of: between about 1 µm and about 5 µm, between about 5 µm and about 25 µm, between about 25 µm and about 50 µm, between about 50 µm and about 75 µm, between about 75 µm and about 100 µm, between about 100 µm and about 125 µm, between about 125 µm and about 150 µm, between about 150 µm and about 175 µm, between about 175 µm and about 200 µm, between about 200 µm and about 225 µm, between about 225 µm and about 250 µm, between about 250 µm and about 275 µm, and between about 275 µm and about 300 µm.

The channel can have a height, excluding any protrusions, selected from the group consisting of: between about 5 µm and about 10 µm, between about 10 µm and about 15 µm, between about 15 µm and about 20 µm, between about 20 µm and about 25 µm, between about 25 µm and about 30 µm, between about 30 µm and about 35 µm, between about 35 µm and about 40 µm, between about 40 µm and about 45 µm, between about 45 µm and about 50 µm, and between about 50 µm and about 55 µm.

The channel can have an aspect ratio of height to width selected from the group consisting of: less than about 1:2, less than about 1:5, less than about 1:10, and less than about 1:15.

The one or more protrusions can each have a substantially rectangular profile. The one or more protrusions can each have a width selected from the group consisting of: between about 0.1 µm and 5 µm, 5 µm and about 10 µm, between about 10 µm and about 15 µm, between about 15 µm and about 20 µm, and between about 20 µm and about 25 µm.

The flexible membrane can be an elastomer. The elastomer can be selected from the group consisting of: PDMS, polytetrafluoroethylene, urethanes, silicones, and perfluoropolyethers. The flexible membrane can have a Young's modulus selected from the group consisting of less than about 10 gPa, less than about 5 gPa, less than about 1 gPa, less than about 0.1 gPa, less than about 0.01 gPa, less than about 0.001 gPa, and less than about 0.0001 gPa.

The channel or membrane can have 2 protrusions. The channel or membrane can have 3 protrusions. The channel or membrane can have 4 or more protrusions.

The sieve valve can further include a pressure channel extending below the flexible membrane.

Another aspect of the invention provides a microfluidic circuit including one or more sieve valves as described herein.

This aspect of the invention can have a variety of embodiments. The microfluidic circuit can further include one or more input/output valves. The one or one or more input/output valves can include one or more input valves and one or more output valves.

The microfluidic circuit can include a mixing circuit. At least one of the sieve valves can be positioned between the one or more input/output valves and the mixing circuit. At least one of the sieve valves can be positioned along the mixing circuit.

Another aspect of the invention provides a microfluidic device including: a plurality of microfluidic circuits as described herein.

Another aspect of the invention provides a microfluidic circuit including: an input valve; a holding chamber in fluid communication with the input valve; a mixing circuit; and a sieve valve as described herein positioned between the holding chamber and the mixing circuit.

Another aspect of the invention provides a microfluidic device including a plurality of microfluidic circuits as described herein.

This aspect of the invention can have a variety of embodiments. The plurality of microfluidic circuits can lie in a plurality of laminar layers of the microfluidic device. The plurality of microfluidic circuits can span across a plurality of laminar layers of the microfluidic device.

Another aspect of the invention provides a kit including: the microfluidic device as described herein; and a capture substrate.

This aspect of the invention can have a variety of embodiments. The kit can further include one or more reagents suitable for performing cell analysis using the microfluidic device. The one or more reagents can include a reagent for promoting cell lysis. The one or more reagents can include an enzyme for promoting cell lysis. The kit can further include instructions for use of the microfluidic device. The capture substrate can include a plurality of beads. The plurality of beads can include a plurality of sets of beads, each set having a different diameter.

Another aspect of the invention provides a system including: a microfluidic device a described herein and a thermocycler.

This aspect of the invention can have a variety of embodiments. The system can further include a detector. The detector can be a mass spectrometer, an optical detector, or a DNA-sequence-based detector.

Another aspect of the invention provides a microfluidic circuit including: a first sieve valve; a second sieve valve fluidically coupled to the first sieve valve; and a control structure adapted and configured to generate fluid flow over the first sieve valve and the second sieve valve in opposite directions.

Another aspect of the invention provides a method of fabricating a microfluidic device. The method includes: depositing a first layer of photoresist; exposing a portion of the first layer of photoresist a cross-linking energy source; depositing a second layer of photoresist; exposing a portion of the second layer of photoresist the cross-linking energy source; and etching the first layer of photoresist and the second layer of photoresist in a single etching step.

Another aspect of the invention provides a microfluidic device fabricated according to the methods described herein.

Another aspect of the invention provides a sieve valve including: a substrate defining a channel; a flexible membrane adapted and configured for deployment within the channel; and one or more protrusions extending into the channel from the substrate or the flexible membrane.

This aspect of the invention can have a number of embodiments. The channel can have a substantially-rectangular profile. The channel can have a width selected from the group consisting of: between about 1 µm and about 5 µm, between about 5 µm and about 25 µm, between about 25 µm and about 50 µm, between about 50 µm and about 75 µm, between about 75 µm and about 100 µm, between about 100 µm and about 125 µm, between about 125 µm and about 150 µm, between about 150 µm and about 175 µm, between about 175 µm and about 200 µm, between about 200 µm and about 225 µm, between about 225 µm and about 250 µm, between about 250 µm and about 275 µm, and between about 275 µm and about 300 µm. The channel can have a height, excluding any protrusions, selected from the group consisting of: between about 5 µm and about 10 µm, between about 10 µm and about 15 µm, between about 15 µm and about 20 µm, between about 20 µm and about 25 µm, between about 25 µm and about 30 µm, between about 30 µm and about 35 µm, between about 35 µm and about 40 µm, between about 40 µm and about 45 µm, between about 45 µm and about 50 µm, and between about 50 µm and about 55 µm. The channel can have an aspect ratio of height to width selected from the group consisting of: less than about 1:2, less than about 1:5, less than about 1:10, and less than about 1:15

The one or more protrusions can each have a substantially rectangular profile. The one or more protrusions can each have a width selected from the group consisting of: between about 0.1 µm and 5 µm, 5 µm and about 10 µm, between about 10 µm and about 15 µm, between about 15 µm and about 20 µm, and between about 20 µm and about 25 µm.

The flexible membrane can be an elastomer. The elastomer can be selected from the group consisting of: PDMS, polytetrafluoroethylene, urethanes, silicones, and perfluoropolyethers.

The flexible membrane can have a Young's modulus selected from the group consisting of: less than about 10 gPa, less than about 5 gPa, less than about 1 gPa, less than about 0.1 gPa, less than about 0.01 gPa, less than about 0.001 gPa, and less than about 0.0001 gPa.

The channel or membrane can include 2 protrusions. The channel or membrane can include 3 protrusions. The channel or membrane can include 4 or more protrusions.

The sieve valve can further include a pressure channel extending below the flexible membrane.

Another aspect of the invention provides a microfluidic circuit including one or more sieve valves as described herein.

This aspect of the invention can have a number of embodiments. The microfluidic circuit can further include one or more input/output valves. The one or one or more input/output valves can include: one or more input valves and one or more output valves.

The microfluidic circuit can further include a mixing circuit. At least one of the sieve valves can be positioned between the one or more input/output valves and the mixing circuit. At least one of the sieve valves can be positioned along the mixing circuit.

Another aspect of the invention provides a microfluidic device including a plurality of microfluidic circuits a described herein.

This aspect of the invention can have a variety of embodiments. The microfluidic circuit can include: an input valve; a holding chamber in fluid communication with the input valve; a mixing circuit; and a sieve valve as described herein positioned between the holding chamber and the mixing circuit.

Another aspect of the invention provides a microfluidic device including a plurality of microfluidic circuits as described herein.

This aspect of the invention can have a variety of embodiments. The plurality of microfluidic circuits can lie in a plurality of laminar layers of the microfluidic device. The plurality of microfluidic circuits can span across a plurality of laminar layers of the microfluidic device.

Another aspect of the invention provides a kit including a microfluidic device as described herein and a capture substrate.

This aspect of the invention can have a variety of embodiments. The kit can include one or more reagents suitable for performing cell analysis using the microfluidic device. The one or more reagents can include a reagent for promoting cell lysis. The one or more reagents can include an enzyme for promoting cell lysis.

The kit can include instructions for use of the microfluidic device.

The capture substrate can include a plurality of beads. The plurality of beads can include a plurality of sets of beads, each set having a different diameter.

Another aspect of the invention provides a system including a microfluidic device as discussed herein and a thermocycler.

This aspect of the invention can have a variety of embodiments. The system can further include a detector. The detector can be a mass spectrometer. The detector can be an optical detector. The detector can be a DNA-sequence-based detector.

Another aspect of the invention provides a method for isolating an analyte, the method comprising: loading a sample into a holding chamber of the microfluidic circuit of the invention, where the holding chamber is in fluid communication to an input port of a mixing circuit; passing the sample into the mixing circuit; capturing the analyte on a capture substrate in the mixing circuit; washing the capture substrate to remove uncaptured components; and releasing the analyte from the capture substrate.

This aspect of the invention can have a variety of embodiments. The capture substrate can be loaded into the microfluidic circuit, the holding chamber, and/or the mixing circuit. The capture substrate can include a bead, microbead, or surface of the microfluidic circuit. The analyte can be a cell, virus, organelle, particle, nucleic acid molecule (e.g., DNA, RNA), polypeptide, carbohydrate, lipid, small molecule, or fragment thereof. The sample can include without limitation an organism, tissue, cell, virus, organelle, particle, nucleic acid molecule, agent comprising a nucleic acid molecule, polypeptide, carbohydrate, lipid, small molecule, or fragment thereof. The capture substrate can include one or more capture reagents, including without limitation an antibody, carboxylic acid, cation, anion, cationic group, anionic group, hydrophobic group, magnetic material, protein, ligand, nucleic acid, and/or an affinity agent.

In another aspect, the invention features a method for generating a library, the method involving loading a cell into a holding chamber of the microfluidic circuit of a previous aspect, wherein the holding chamber is in fluid communication to an input port of a mixing circuit; passing the cell into the mixing circuit and contacting the cell with a lysis reagent, thereby releasing genomic nucleic acid molecules; fragmenting the genomic nucleic acid molecules and fixing an amplification adaptor to the 5' and 3' end of the fragments;

amplifying the fragments to obtain a library pool;

capturing the library pool on a capture substrate in the mixing circuit;

washing the capture substrate to remove uncaptured components; and releasing the library pool from the capture substrate. In one embodiment, the method further involves analyzing the library pool by mass spectrometry, optical detection, or DNA-sequence-based detection. In another embodiment, the cell is a bacterial, archaeal, plant, fungal, mammalian, animal, human, chimeric, or hybrid cell. In another embodiment, the cell is selected from the group consisting of a soil bacterium, *M. tuberculosis, P. aeruginosa*, and *E. coli*.

In various embodiments, the method further involves opening at least one of the sieve valves to remove the capture substrate from the microfluidic circuit, the holding chamber, and/or the mixing circuit.

In various embodiments, at least one of the sieve valves is positioned between the holding chamber and the mixing circuit, and the method further involves activating the sieve valve positioned between the holding chamber and the mixing circuit in order to retain the capture substrate and the sample within the holding chamber while permitting fluid to pass through the sieve valve. In various embodiments, the method further involves washing the capture substrate with a washing solution; and releasing the analyte from the washed capture substrate.

In various embodiments, the method further involves loading one or more reagents for modifying the analyte in the microfluidic circuit; and mixing the one or more reagents and the analyte in the mixing circuit to modify the analyte; and removing the modified analyte from the microfluidic circuit. The modifying can include fixing a label, reporter, nucleic acid molecule, polypeptide, or synthetic molecule to the analyte. The modifying can include amplification of a nucleic acid molecule (e.g., DNA) and/or reverse transcription of a nucleic acid molecule (e.g., RNA to cDNA).

In particular embodiments, the analyte is a nucleic acid molecule, and the method further involves loading one or more reagents for fragmenting the nucleic acid molecule in the microfluidic circuit (e.g., engineered Tn5 transposomes); and mixing the one or more reagents and the nucleic acid molecule in the mixing circuit to fragment the nucleic acid molecule; and removing the nucleic acid fragments from the microfluidic circuit. The method can further involve fixing an amplification adaptor to the 5' and 3' ends of the nucleic acid fragments (e.g., engineered Tn5 transposomes with adapter oligo transposons that simultaneously fragment and adapter tag the genomic DNA). The method can further involve contacting the nucleic acid fragments with primers that hybridize the amplification adaptors inside the mixing circuit; and amplifying the nucleic acid fragments inside the mixing circuit. Amplifying can involve, for example without limitation, polymerase chain reaction (PCR), helicase-dependent amplification (HDA), nicking enzyme amplification reaction (NEAR), loop mediated isothermal amplification (LAMP), rolling circle amplification (RCA), or recombinase polymerase amplification (RPA).

The nucleic acid fragments can provide a sequence library pool consisting of individual samples having a coefficient of variation of 0.5 or less in their respective quantities. The sample can contain a single prokaryotic or eukaryotic cell or a plurality of cells (e.g., bacterial, archaeal, plant, fungal, mammalian, animal, human, chimeric, and hybrid cells). In one embodiment, the bacterium is *M. tuberculosis*. In another embodiment, the sample is a soil sample containing soil bacteria.

BRIEF DESCRIPTION OF THE DRAWINGS

For a fuller understanding of the nature and desired objects of the present invention, reference is made to the following detailed description taken in conjunction with the figure wherein:

FIG. 4 shows a flow diagram of a high level process for collecting components of a cell, in accordance with an embodiment of the disclosure;

FIG. 29 is a chart depicting amplification of a nucleic acid sample by barcoding nucleic acid molecules in the sample with adaptors for amplification and PCR amplification using the microfluidic device in accordance with an embodiment of the disclosure;

FIG. 42 depicts optimal fragment size distribution (~200-~600 bp) for next generation sequencing (e.g., ILLUMINA®);

FIGS. 45A and 45B depicts a heat map of Human Gut Microbiome (HGMB) sequencing with <100 pg (20,000 cells) input;

FIG. 50 is a chart showing the reduced cost of sequencing using the microfluidic chip and the feasibility of <$1 sequencing sample preparation;

FIGS. 52A-52C depicts a method for fabricating a microfluidic device according to an embodiment of the invention;

FIG. 62 depicts fragment diversity and information complexity of human genomic DNA in sequencing library prepared on chip;

FIG. 64 is a graph depicting on chip reverse transcription and cDNA conversion (e.g., for preparation of sequencing library);

FIG. 65 is a graph depicting on-chip RNA-seq library construction;

FIG. 67A provides a photograph of the 96×36 nL microfluidic library construction device filled with food coloring to highlight features. The dime and white scale bar (1 cm) show physical size. Inset: the reactor unit (medium gray at bottom), filter unit (light gray in middle), and reservoir unit (dark gray at top). Black and gray arrows designate reagent input ports and sample input/output ports, respectively.

FIG. 67B is a schematic diagram that describes a microfluidic sample preparation workflow that distinguishes the gDNA input mode (top) from cell input mode (bottom) is depicted.

FIG. 67C shows the estimated complexity and mapping rate to the *P. aeruginosa* PA14 reference genome for the clinical *P. aeruginosa* isolate DNA where the input to our device was gDNA.

FIG. 67D provides a graphical representation of the sequencing statistics for low input *E. coli* processed with the device. The *E. coli* mapping rate is that mapped to the reference *E. coli* BL21-DE3. For each of FIGS. 67D, E, and F, the library complexity was calculated using Picard tools (http://broadinstitute.github.io/picard/) and the human DNA read fraction was determined using deconseq (http://deconseq.sourceforge.net/).

FIG. 67E provides a graphical representation of the sequencing statistics for low input soil microbes processed with the device.

FIG. 67F provides a graphical representation of the sequencing statistics for low input *M. tuberculosis* cells processed with the device. The *M. tuberculosis* reads were mapped to the *M. tuberculosis* OFXR-14 reference genome.

DEFINITIONS

Figure 1:
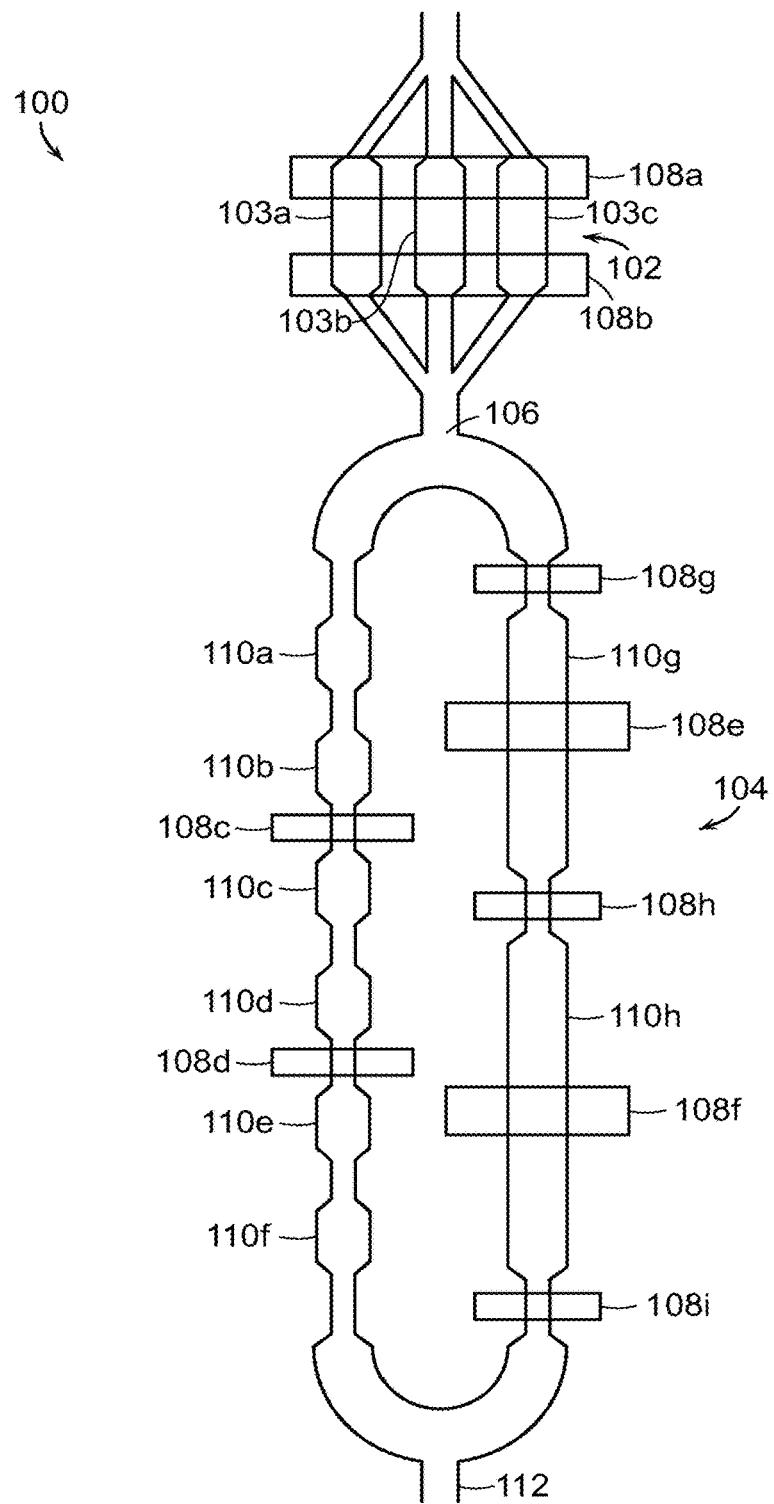
FIG. 1 shows an illustrative diagram of a microfluidic channel for collecting components of a cell, in accordance with an embodiment of the present disclosure.

The instant invention is most clearly understood with reference to the following definitions:

As used in the specification and claims, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The term "analyte" is meant any compound under investigation using an analytical method. In particular embodiments, analytes include any nucleic acid molecule, polypeptide, carbohydrate, lipid, small molecule, marker, or fragments thereof. In other embodiments, analytes include a cell, virus, organelle, or particle.

By "capture reagent" or "capture substrate" is meant a reagent that specifically binds an analyte to select or isolate the analyte. Exemplary capture reagents include without limitation an antibody, carboxylic acid, cation, anion, cationic group, anionic group, hydrophobic group, magnetic material, protein, ligand, nucleic acid, and an affinity agent. Capture substrates may be in the form of a bead, microbead, or surface of a microfluidic circuit.

The term "cell" is meant to include eukaryotic and prokaryotic cells, such as bacteria. Exemplary cells include, but are not limited to, *E. coli*.

As used in the specification and claims, the terms "comprises," "comprising," "containing," "having," and the like can have the meaning ascribed to them in U.S. patent law and can mean "includes," "including," and the like.

By "decreases" is meant a negative alteration of at least 10%, 25%, 50%, 75%, 100%, 200%, 300%, 400%, 500%, 1000%, or more.

By "fragment" is meant a portion of an analyte. With reference to a polypeptide or nucleic acid molecule, a portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "increase" is meant a positive alteration of at least 10%, 25%, 50%, 75%, 100%, 200%, 300%, 400%, 500%, 1000%, or more.

As used herein, "isolated" refers to a molecule that is substantially free of other elements present in its natural environment. For instance, an isolated nucleic acid molecule is substantially free of cellular material or other nucleic acid molecules from the cell or tissue source from which it is derived. The term "isolated" also refers to preparations at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

By "reference" is meant a standard or control condition.

The term "sample" is meant to include any material collected for analysis. A sample can include, for example, molecules (e.g., toxins such as ricin, pharmaceuticals, and the like), biomolecules (e.g., polynucleotides, polypeptides, lipids, and the like), cells (e.g., eukaryotic and prokaryotic cells, such as bacteria), spores (e.g., *B. anthracis*), viruses (e.g., influenza, smallpox, and the like), and other materials.

By "specifically binds" is meant a compound (e.g., capture reagent) that recognizes and binds a molecule (e.g., an analyte), but which does not substantially recognize and bind other molecules in a sample, for example, a biological sample.

Any compounds, compositions, or methods provided herein can be combined with one or more of any of the other compositions and methods provided herein.

Unless specifically stated or obvious from context, as used herein, the term "or" is understood to be inclusive. The term "including" is used herein to mean, and is used interchangeably with, the phrase "including but not limited to."

Other features and advantages of the invention will be apparent from the following description of the desirable embodiments thereof, and from the claims.

DETAILED DESCRIPTION

To provide an overall understanding of the disclosure, certain illustrative embodiments will now be described. However, the systems and methods described herein can be adopted and modified as is appropriate for the application being addressed. The systems and methods described herein can be employed in other suitable applications, and that such other additions and modifications will not depart from the scope thereof.

FIG. 1 shows a diagram of a single microfluidic channel 100 for collecting components of a cell. The microfluidic channel includes a holding chamber 102 and a mixing circuit 104. The holding chamber 102 includes individual chambers 103a-103c that are connected to an input port 106 of the mixing circuit 104. In other embodiments, the holding chamber 102 can be a single chamber. Sieve valves 108a and 108b span across chambers 103a-103c and are controlled using control lines or channels (not shown) that run underneath or above the microfluidic channel 100. In other embodiments, one or more sieve valves may span across part of the holding chamber 102 to provide selective control of the passage of material through the holding chamber 102. The control lines can be filled with a liquid such as water or a gas such as air to control the sieve valves 108a-108b, although any suitable fluid can be used. The holding chamber 102 has a height that is substantially the same along its length. In some embodiments, the holding chamber 102 may have a height that is substantially the same as the height of the mixing circuit 104. In other embodiments, the holding chamber may have a height that varies along its length. The holding chamber can have a total volume between about 10 nL and about 1000 nL.

The holding chamber 102 can be configured to store or trap a capture substrate, such as a nucleic acid capture substrate, when the sieve valves 108a and 108b are closed. Any suitable capture substrate for capturing a cellular component of interest can be used, provided that the substrate can reversibly bind the cellular component of interest. For capturing nucleic acids, the capture substrate can be any substrate that binds nucleic acids in its activated state, such as solid phase reversible immobilization (SPRI) capture beads or any other suitable substrate that can capture a nucleic acid. A non-limiting example of a capture substrate that can be used to capture a nucleic acid is DYNABEADS® capture beads available from Life Technologies of Carlsbad, Calif. In some embodiments, the capture substrate can be configured to capture a protein, such as hemoglobin, antibodies, carbohydrates, small molecules, or any other cellular component that can be collected from a cell. When in the presence of an activation chemical, or after treatment with an activation chemical, the capture substrate is in an activated state. While activated, the capture substrate selectively binds a cellular component of interest, such as nucleic acids. A non-limiting example of an activation chemical that binds a component of a cell to a capture substrate is a solution of 20% polyethylene glycol (PEG) and 2.5M NaCl.

To trap the capture substrate, sieve valve 108a and/or 108b is closed and flow of the fluid in the microfluidic channel is directed through the holding chamber 102. Generally, the capture substrate has a dimension that is smaller than a height of the microfluidic channel 100, but larger than the height of the microfluidic channel 100 at a closed sieve valve, such as any of sieve valves 108a-108i. For example, the SPRI beads have a diameter that is smaller than the height of the holding chamber, but larger than a height of the holding chamber at one of closed sieve valves 108a or 108b. Those of skill in the art will understand that a height, as the term is used herein, can be altered by lowering a ceiling or by raising a floor, so long as the dimension of the affected passage is reduced. Thus, the capture substrate is trapped at sieve valve 108a or 108b when the sieve valve 108a or 108b is closed. In some embodiments, the capture substrate may comprise more than one capture bead loaded into the microfluidic channel 100. When multiple capture beads are trapped at one of the sieve valves 108a or 108b, a column of capture beads is created that can block the passage of cells, while being sufficiently porous to permit the passage of fluid around the beads. Using this column of beads, cells can be concentrated inside holding chamber 102 before passing the cells to further processing steps inside the mixing circuit 104.

The capture substrate can be trapped in the holding chamber 102 by sieve valve 108a and/or 108b and subsequently washed with a washing solution to remove contaminants. The capture substrate may also be washed after activation and have bound cellular components. Similarly, to purify the bound components, the capture substrate can be washed with a washing solution to remove contaminants and then deactivated with an elution buffer or elution wash to release the cellular components, e.g., nucleic acids. After the capture substrate is washed and the cellular components collected, sieve valves 108a and 108b can be opened and the capture substrate can be passed out of the channel or back into the mixing circuit 104.

The mixing circuit 104 includes chambers 110a-110h, sieve valves 108c-108i, and an output port 112. The mixing circuit 104 can have substantially the same height along its entire length. In some embodiments, the height of the mixing circuit 104 can vary along its length. For example, the chamber 110a can have a first height and the chamber 110b can have a second height. The total volume of the mixing circuit can be between about 10 nL and about 1000 nL. Because smaller volumes require smaller amounts of reagents and solvents and therefore lower costs, smaller volumes are preferred. Accordingly, in some embodiments, the total volume of the mixing circuit is between about 30 nL and about 200 nL. Each of chambers 110a-110h can have a volume between about 10 nL and about 250 nL. Chambers 110a-110h can have different volumes. For example, chamber 110a can have a first volume and chamber 110h can have a second volume that is larger than the first volume. A valve such as valve 108e can be provided on the chamber 110g and can be closed to effectively create two separate chambers, optionally in at least partial fluid communication. The sieve valves 108c-108i can be used as a peristaltic pump to pump fluid around the mixing circuit. To do so, some or all of sieve valves 108c-108i are closed in a sequence along the length of the mixing circuit to push fluid around the circuit.

Figure 2A:
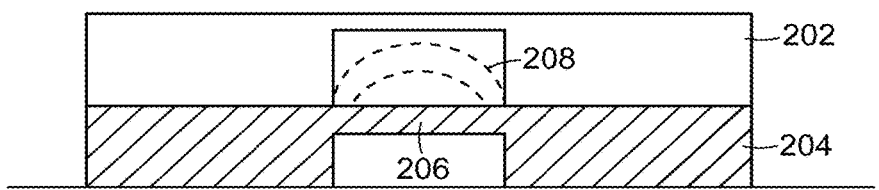
FIG. 2A shows an illustrative diagram of a cross-section of a sieve valve, in accordance with an embodiment of the disclosure.

FIG. 2A shows an illustrative diagram of a sieve valve 200 that can correspond to any of valves 108a-108i. The microfluidic channel 202 sits on a "control" layer 204. The control layer includes a membrane 206 that can be deflected upwards. When the sieve valve 200 is closed, the membrane 206 deflects to a closed position shown by dotted line 208. While in a closed position, the membrane reduces a height of the channel 202.

Sieve valve 200 can be closed using fluid pressure, gas pressure, or any other suitable mechanism to deflect the membrane 206. For example, sieve valve 200 can be actuated by injecting gases (e.g., air, nitrogen, and argon), liquids (e.g., water, silicon oils, and other oils), solutions containing salts and/or polymers (including, but not limited to, polyethylene glycol, glycerol, and carbohydrates), and the like into the control channel. In addition to elastomeric valves actuated by pressure-based actuation systems, monolithic valves with an elastomeric component and electrostatic, magnetic, electrolytic and electrokinetic actuation systems can be used as discussed, for example, in U.S. Pat. No. 6,767,706 and U.S. Patent Application Publication Nos. 2002/0109114 and 2002/0127736.

Membrane 206 can be any material capable of deforming sufficient to partially occlude the flow channel. In general, any material having a Young's modulus less than a metal will be sufficient. For example, the membrane 206 can have a Young's modulus of less than about 10 gPa, less than about 5 gPa, less than about 1 gPa, less than about 0.1 gPa, less than about 0.01 gPa, less than about 0.001 gPa, less than about 0.0001 gPa, and the like.

Suitable membrane materials include elastomers such as PDMS, polytetrafluoroethylene (PTFE), urethanes, silicones, perfluoropolyethers, and the like.

A large variety of elastomeric materials may be used in fabrication of the devices of the invention. Elastomers in general are polymers existing at a temperature between their glass transition temperature and liquefaction temperature. For illustration, a brief description of the most common classes of elastomers is presented below.

Silicone polymers have great structural variety, and a large number of commercially available formulations. In an exemplary aspect of the present invention, the present systems are fabricated from an elastomeric polymer such as GE® RTV 615 (formulation), a vinyl-silane cross-linked (type) silicone elastomer (family). In one embodiment, the silicone polymer is polydimethylsiloxane (PDMS).

Functionalized photocurable perfluoropolyether (PFPE) is particularly useful as a material for fabricating solvent-resistant microfluidic devices for use with certain organic solvents. These PFPEs have material properties and fabrication capabilities similar to PDMS but with compatibility with a broader range of solvents. Suitable PFPE compounds are described, for example, in International Publication Nos. WO 2005/030822 and WO 2005/084191 and Rolland et al., "Solvent-resistant photocurable 'liquid Teflon' for microfluidic device fabrication," 126 J. Amer. Chem. Soc. 2322-23 (2004).

Other suitable materials include polyisoprenes, polybutadienes, polychloroprenes, polyisobutylenes, poly(styrene-butadiene-styrene)s, polyurethanes, poly(bis(fluoroalkoxy)phosphazene) (PNF, Eypel-F), poly(carborane-siloxanes) (e.g., Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (available, for example, under the VITON® trademark), elastomeric compositions of polyvinylchloride (PVC), polysulfone, polycarbonate, polymethylmethacrylate (PMMA), and polytetrafluoroethylene (available, for example, under the TEFLON® trademark).

Figure 2B:
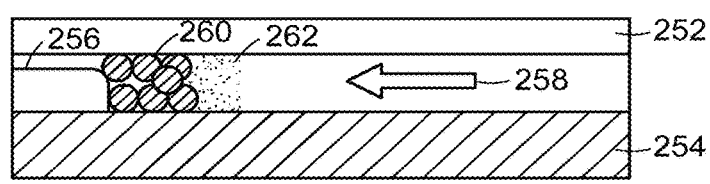
FIG. 2B shows an illustrative diagram of a cross-section of a "closed" sieve valve with a column of capture beads and cells trapped at the sieve valve, in accordance with an embodiment of the disclosure.

In other embodiments, a valve that seals an entire portion of the channel 202 can be used. In this case, when the membrane 206 is deflected, the membrane 206 will match the shape of the channel 202 and seal the channel 202 to block the passage of fluid and particles. FIG. 2B shows an illustrative diagram of a sieve valve 250 with a column of capture beads 260 and cells 262 trapped at the deflected membrane 256. When the sieve valve 250 is activated, fluid may still continue to flow, for example in direction 258, through the valve. Capture beads 260 are trapped at the membrane 256 because they are too large to fit past the partial seal of the membrane 256. As more and more capture beads 260 are trapped at the sieve valve, the capture beads 260 form a column that traps cells 262. The column of capture beads 260 can be used to concentrate cells at a sieve valve 250.

Capture beads of varying diameters can be used to retain samples of varying sizes. For example if capture beads having a diameter of 1 mm are insufficient to retain a sample, 1 mm diameter capture beads can be introduced upstream of the deployed sieve valve, followed by capture beads of 0.75 mm, and so on until a desired porosity is achieved.

When sieve valves 108 are closed, a membrane associated with the control layer deflects and creates a partial seal in the microfluidic channel so that fluid may continue to flow through the valve, but a height of the channel is reduced. The deflected membrane may have a different profile shape than the microfluidic channel. For example, the deflected membrane can have a rounded profile while the channel can have a rectangular profile. In this case, when the membrane deflects, the corners of the channel remain open to the passage of the fluid, even while larger solid particles, such as capture beads, are blocked.

Figure 3:
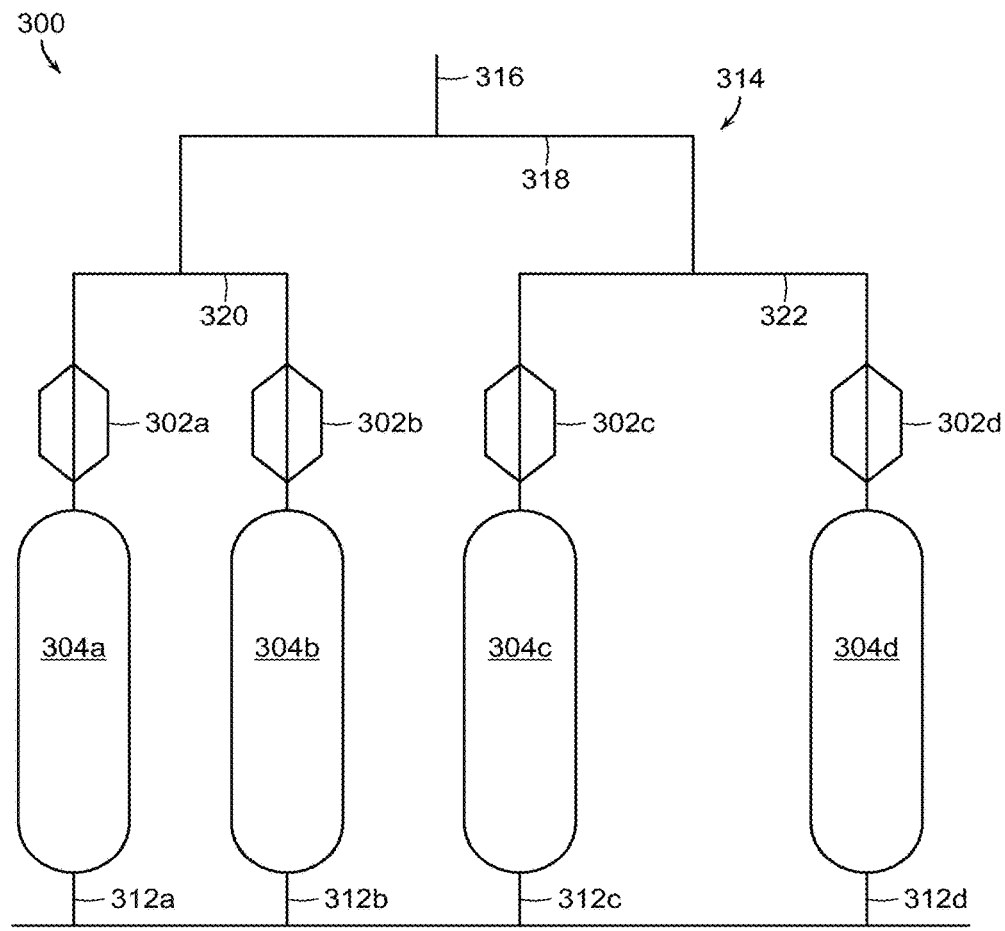
FIG. 3 shows an illustrative diagram of a microfluidic system having a cell separation circuit connected to several holding chambers and mixing circuits, in accordance with an embodiment of the disclosure.

FIG. 3 shows an illustrative diagram of a microfluidic system 300 having a cell separation circuit 314 connected to several holding chambers 302a-302d and mixing circuits 304a-304d. Cell separation circuit 300 can receive a cell at an input port 316. The input port 316 can be coupled to a well that is compatible with a pipette, such as a multi-channel pipette. The cell can be cultured and allowed to divide. After division, the daughter cells can be separated in a separation channel 318. Each cell can be allowed to divide again and the daughter cells can be separated in separation channels 320 and 322. Any number of separation stages or channels can be included in cell separation circuit. Each of holding chambers 302a-302d and each of mixing circuits 304a-304d can correspond to a cell line. The process of sequence library preparation as described below can be performed on each cell line and the resulting nucleic acid libraries can be extracted from output ports 312a-312d. While FIG. 3 only shows four holding chambers and four mixing circuits, any number of holding chambers and mixing circuits can be included in the system. Each of the steps described below can be parallelized across each of holding chambers 302a-302d and mixing circuits 304a-304d for uniformity and consistency of sample preparation.

FIG. 4 shows a flow diagram of a high-level process 400 for collecting components of a cell. Process 400 can be conducted by loading a cell into a holding chamber of a microfluidic device, wherein the holding chamber is coupled to an input port of a mixing circuit (402), loading a capture substrate configured to capture a nucleic acid into the holding chamber (404), passing the cell and the capture substrate into the mixing circuit, wherein the mixing circuit comprises a plurality of chambers, and the mixing circuit has a height that is substantially the same along the entire mixing circuit (406), lysing the cell to release components of the cell (408), capturing a target component of the cell on the capture substrate (410), washing the capture substrate to remove uncaptured components (412), and releasing the target component from the capture substrate (414). This process, in part or in its entirety, can be repeated until a desired purity or yield of cellular components is achieved.

At step 402, a cell is loaded into a holding chamber of a microfluidic device and the holding chamber is connected to an input port of a mixing circuit. In other embodiments, more than one cell can be loaded into the holding chamber. At step 404, a capture substrate configured to capture a nucleic acid or other cellular component is loaded into the holding chamber. Capture substrate can correspond to a capture bead such as an SPRI bead. At 406, the cell and the capture substrate are passed into the mixing circuit. The cells and capture substrate can be concentrated at a sieve valve in the holding chamber before passage into the mixing circuit.

At step 408, the cell is lysed to release components of the cell and the capture substrate is activated to capture the cellular component of interest. For example, a chemical for promoting cell lysis can be loaded into a first chamber of the mixing circuit and an enzyme for promoting cell lysis can be loaded into a second chamber of the mixing circuit.

An activation chemical for activating the capture substrate can be added to a third chamber of the mixing circuit. The chemical, enzyme, and activation chemical can then be mixed in the mixing circuit while applying an elevated temperature to lyse the cell and release cellular components for capture by the capture substrate.

As one of skill in the art would recognize, other processes for lysing the cell can be employed (e.g., with or without elevating the temperature), the reagents can be added sequentially or together, the cell and the capture substrate can be held in different chambers (e.g., so that the activation chemical is added directly to the capture substrate and does not contact the cell prior to lysis), and the various steps can be conducted in any suitable order, provided that the cellular components are released for capture by the activated capture substrate.

To keep the microfluidic device from drying out while applying an elevated temperature, hydration lines can be included in the control layer or the channel layer. When applying the elevated temperature, a fluid from the hydration lines will evaporate and permeate the microfluidic channel, thus keeping the channel from drying out. The fluid pressure in the hydration lines can be varied to modify the amount of hydration that is applied to the microfluidic device while applying an elevated temperature, e.g., to maintain suitable hydration throughout the device.

The cellular components can be nucleic acids.

After cell lysis, the enzyme can be neutralized and/or diluted in the mixing circuit.

To elevate the temperature of the microfluidic device, any suitable method of controlling the temperature of the device can be used. For example, the device can be placed on a thermocycler to elevate the temperature of the device and maintain a specified temperature of the device. Alternatively, the thermocycler can be set to vary between a lower temperature and a higher temperature over a predetermined period of time. The predetermined period of time can correspond to a minimum amount of time for a cell lysis reaction to occur in the mixing circuit. In other embodiments, the device can be subjected to a lower temperature to cool the device, chemicals, enzymes, fluid, and/or components of the cell. This microfluidic device is well suited for various temperature control solutions through standard lab equipment and without extensive modifications to the equipment.

At step 410, a target component of the cell is captured on the capture substrate. While in the presence of the activation chemical, the capture substrate selectively binds target cellular components. After capturing the target cellular components, the capture substrate (having the target components bound thereto) can be moved into the holding chamber and trapped in the holding chamber by sieve valves so that the capture substrate can be washed. Collecting the capture substrate in the holding chamber, which is located outside the mixing circuit, allows for fluid in the mixing circuit to flow around the circuit with less resistance than if the capture substrate were collected in the mixing circuit.

At step 412, the capture substrate is washed to remove uncaptured components. This washing process removes the components of the cell that were not captured by the capture substrate.

At step 414, the target component is released from the capture substrate. To release the target components from the capture substrate, the activation chemical can be washed away or diluted by an elution solution or elution buffer. In other embodiments, the capture substrate can be contacted by a deactivation chemical to release the target components. Release of the target components can occur in the mixing circuit or while the capture substrate is trapped in the holding chamber. If the target components are released in the mixing circuit, the target components can be passed into the holding chamber in a subsequent step. Process 400 can be repeated in part or in its entirety until a predetermined yield or purity of target components is achieved.

After the desired purity of target components is achieved, target components can be passed back into the mixing circuit for further processing. If the target components are nucleic acids, a first chemical for fragmenting the nucleic acids can be added into a first chamber in the mixing circuit. A second chemical for promoting fragmentation of the nucleic acid can be added to a second chamber of the mixing circuit. In some embodiments, the first and second chemical can correspond to reagents in the NEXTERA® DNA sample preparation kit that simultaneously fragment and tag nucleic acids with sequencing adaptors. The nucleic acids and chemicals can then be mixed in the mixing circuit to fragment the nucleic acids into fragmented nucleic acids. After fragmentation, a tagging chemical can optionally be loaded into the mixing circuit to tag the fragmented nucleic acids. After tagging, a capture substrate can be loaded into the mixing circuit with the activation chemical (or after activation by an activation chemical), and the tagged nucleic acid fragments can be captured on the substrate. In some embodiments, the fragmentation and tagging are performed together.

The capture substrate (having the tagged nucleic acid fragments bound thereto) can then be trapped in the holding chamber and subsequently washed to remove uncaptured nucleic acids. In an alternative embodiment, the nucleic acids can be fragmented using an enzyme such as the NEB fragmentase enzyme. The ends of the fragmented nucleic acids can be repaired using conventional end repair techniques and dsDNA adaptor ligation. This alternative embodiment can reduce reagent costs compared to the simultaneous fragmenting and tagging as described above.

A barcoding primer can be loaded into the mixing circuit to barcode the nucleic acid fragments. After the nucleic acids are barcoded, polymerase chain reaction (PCR) can be performed on the nucleic acids to amplify the nucleic acids. A capture substrate can be loaded into the mixing circuit again to capture the amplified nucleic acids. At this point, size selection and normalization of the nucleic acids occurs. Nucleic acid sizes can be selected by varying the concentration of capture substrate that is loaded into the microfluidic channel as a lower ratio of capture substrate to nucleic acids will selectively bind larger nucleic acids. Smaller nucleic acids will be washed away during each washing process leaving larger nucleic acids attached to the capture substrate.

Size selection can be an important factor for further processing, such as sequencing on a sequencing device. For example, a nucleic acid sequencing device may require sequences of sufficient length to accurately and precisely obtain sequencing information from the fragments. Normalization of the concentration of the solution of nucleic acids (or any other target components) can occur at any point in the process. Normalization refers to modifying the concentration of the solution of nucleic acids (or other target components) to facilitate its use in subsequent processing (e.g., sequencing in a sequencing device). Preferably, each sample prepared using the microfluidic device will be normalized to a substantially similar concentration of nucleic acids (or other target component). The capture substrate can be activated with an activation chemical to capture the amplified nucleic acids and then trapped in the holding chamber using sieve valves as described above. After washing the capture substrate with a washing solution and releasing and collecting the nucleic acids with an elution solution, the nucleic acids can be removed from the microfluidic device. The removed nucleic acids correspond to a sequence library that can be sequenced to generate genomic data.

Figure 5:
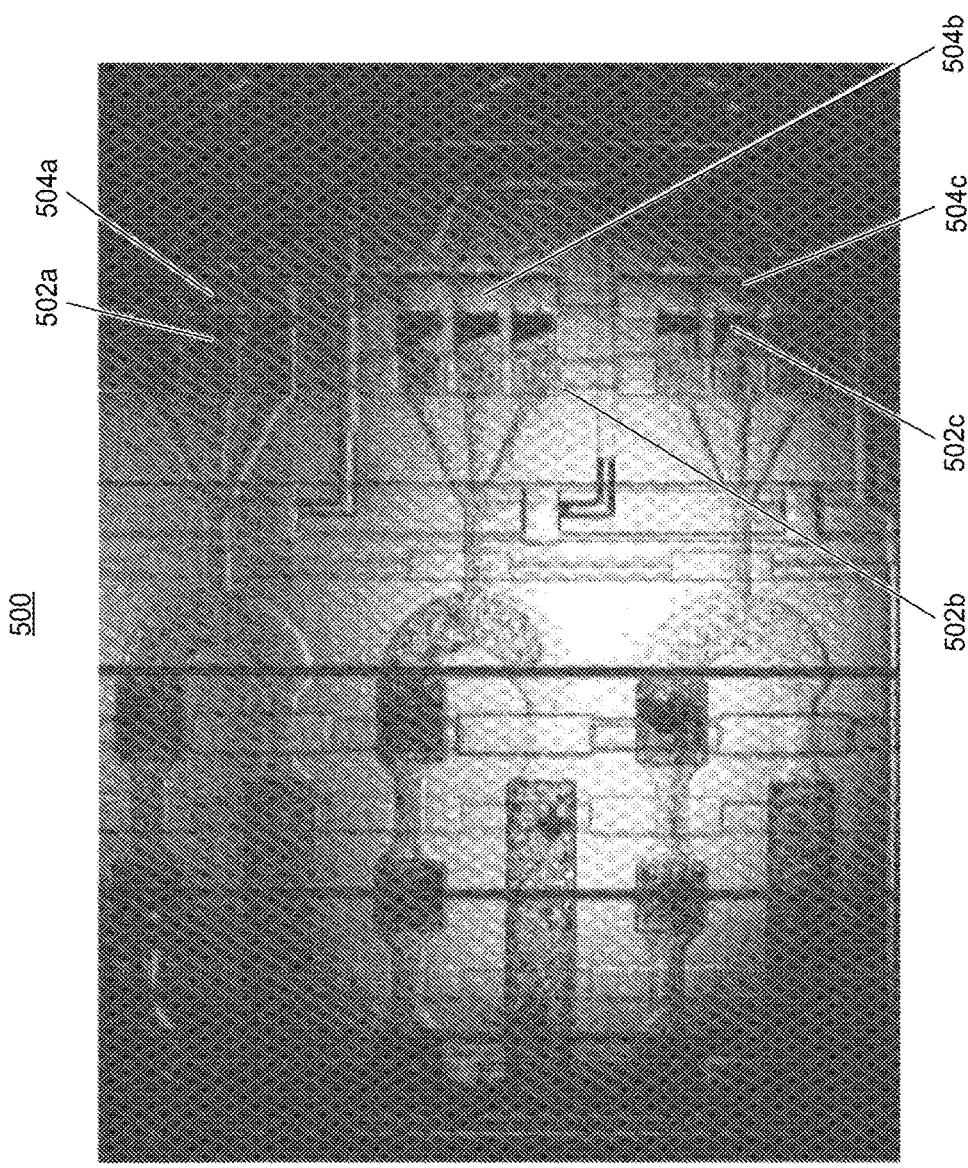
FIG. 5 shows an image of a microfluidic device with capture beads trapped at various sieve valves, in accordance with an embodiment of the disclosure.

FIG. 5 shows an image of a microfluidic device 500 with capture beads 502a-502c trapped at various sieve valves 504a-504c, in accordance with an embodiment of the disclosure. As can be seen by this image taken from a microscope, columns of capture beads 502a-502c have formed at closed sieve valves 504a-504c. This image demonstrates a proof of concept for trapping a capture substrate inside a microfluidic device, such as an SPRI bead, to create a reversible substrate column at a sieve valve. This image can correspond to a snapshot of step 410 of process 400 described above with respect to FIG. 4, where a capture substrate is trapped in a holding chamber located outside the mixing circuit. Trapping the capture substrate outside the mixing circuit is beneficial because the resulting column of capture beads does not impede fluid flow inside the mixing circuit.

Figure 6:
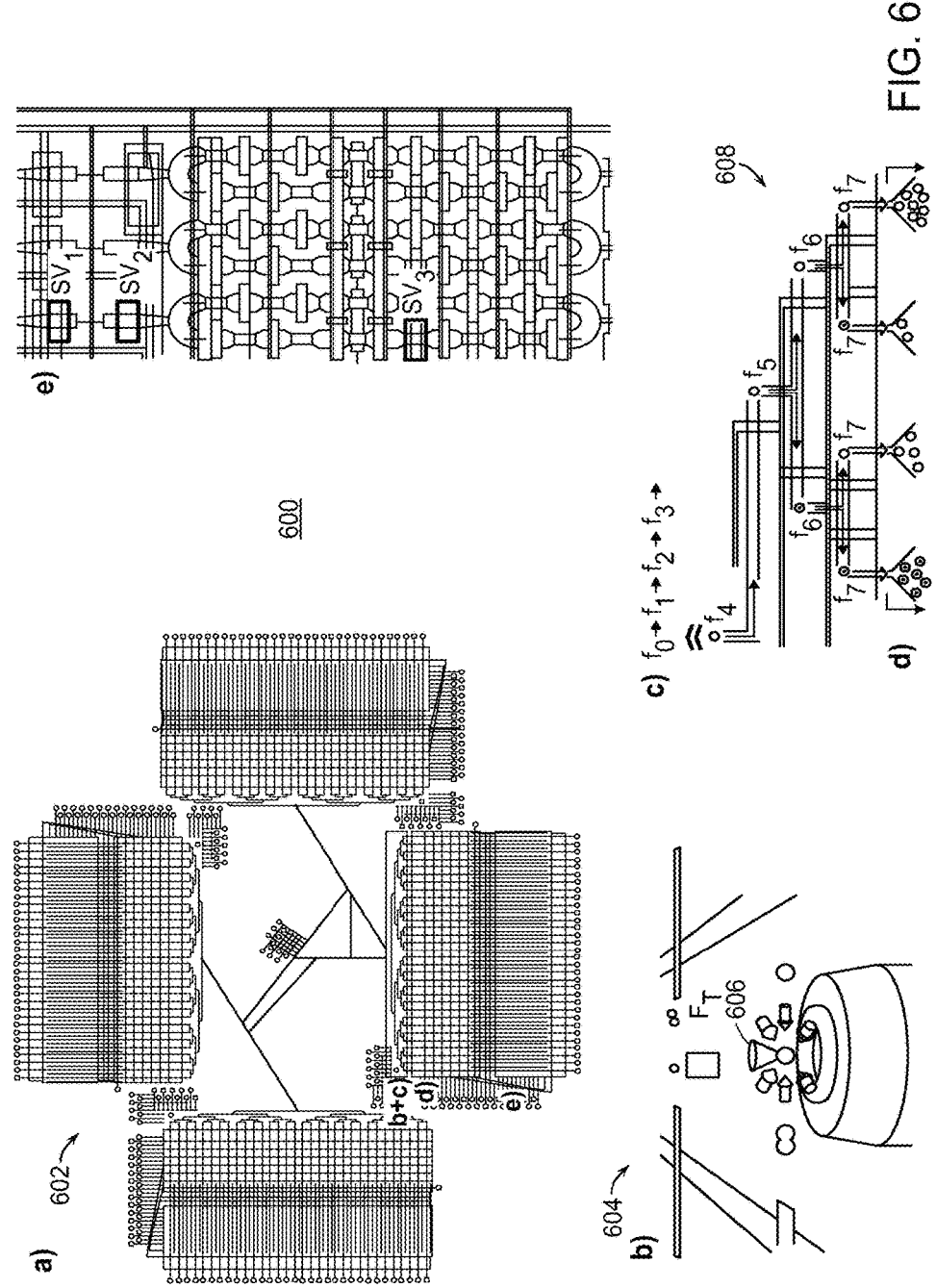
FIG. 6 shows an illustrative diagram of a microfluidic device for separating cells and capturing components of the cells, in accordance with an embodiment of the disclosure.

FIG. 6 shows an illustrative diagram of a microfluidic device 600 for separating cells and capturing components of the cells, in accordance with an embodiment of the disclosure. The microfluidic system 602 can correspond to the system described above with respect to FIGS. 1-3. Optical tweezers 606 can be used to move individual cells through a channel in a microfluidic device 604. Cell separation circuit 608 can correspond to the cell separation circuit discussed with respect to FIG. 3.

Figure 7A:
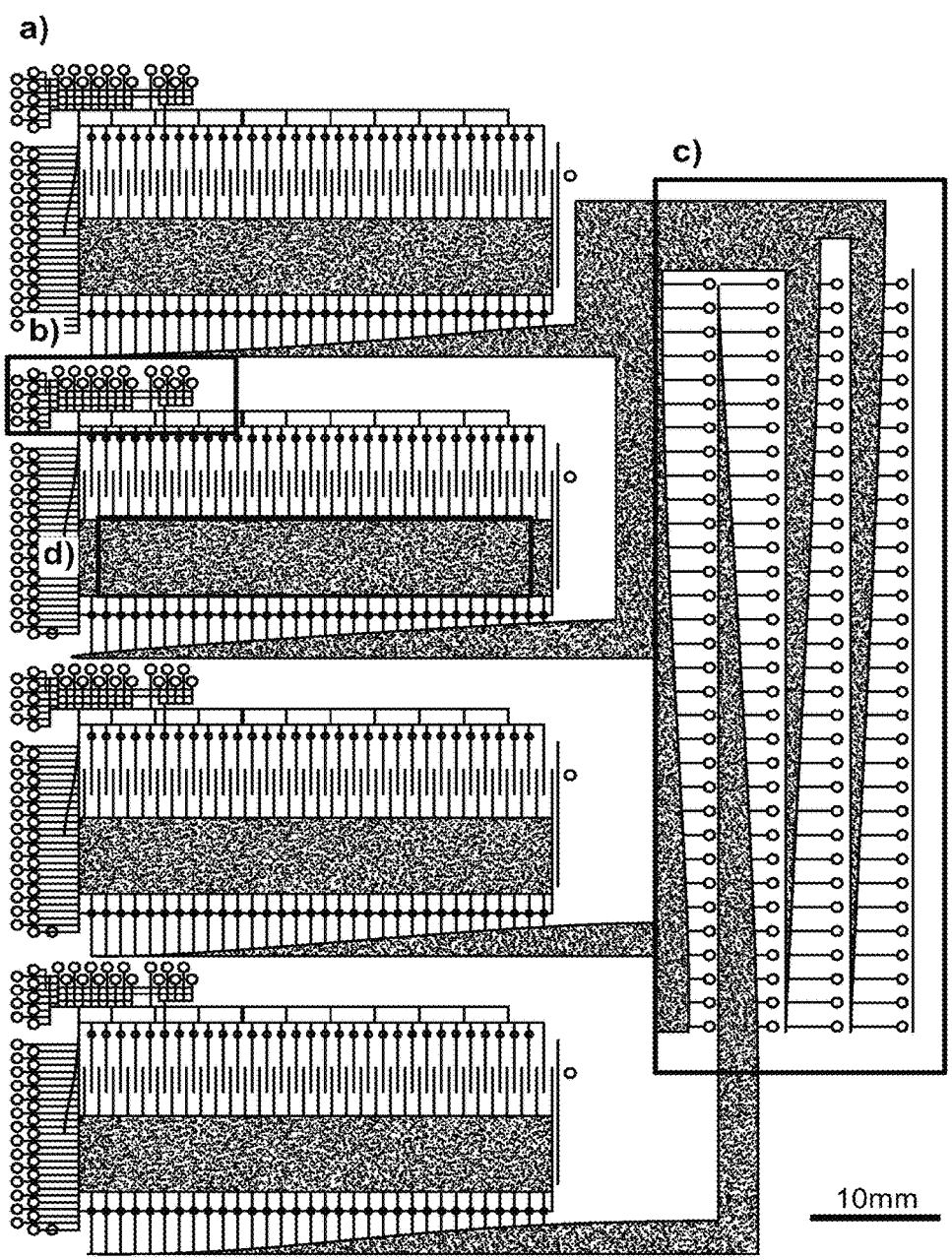
FIGS. 7A-7C show an illustrative diagram of a microfluidic device and the associated input and output ports of the device, in accordance with an embodiment of the disclosure.
Figure 7B:
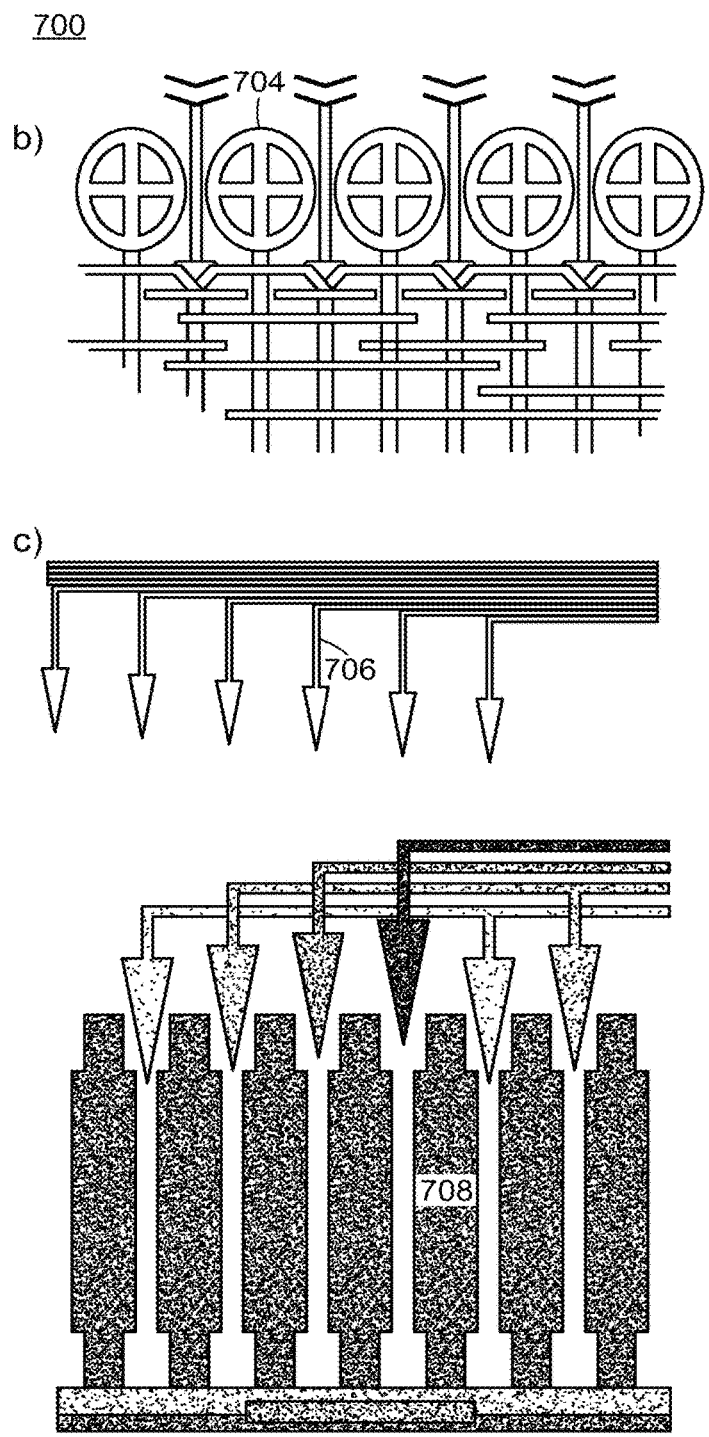
Figure 7C:
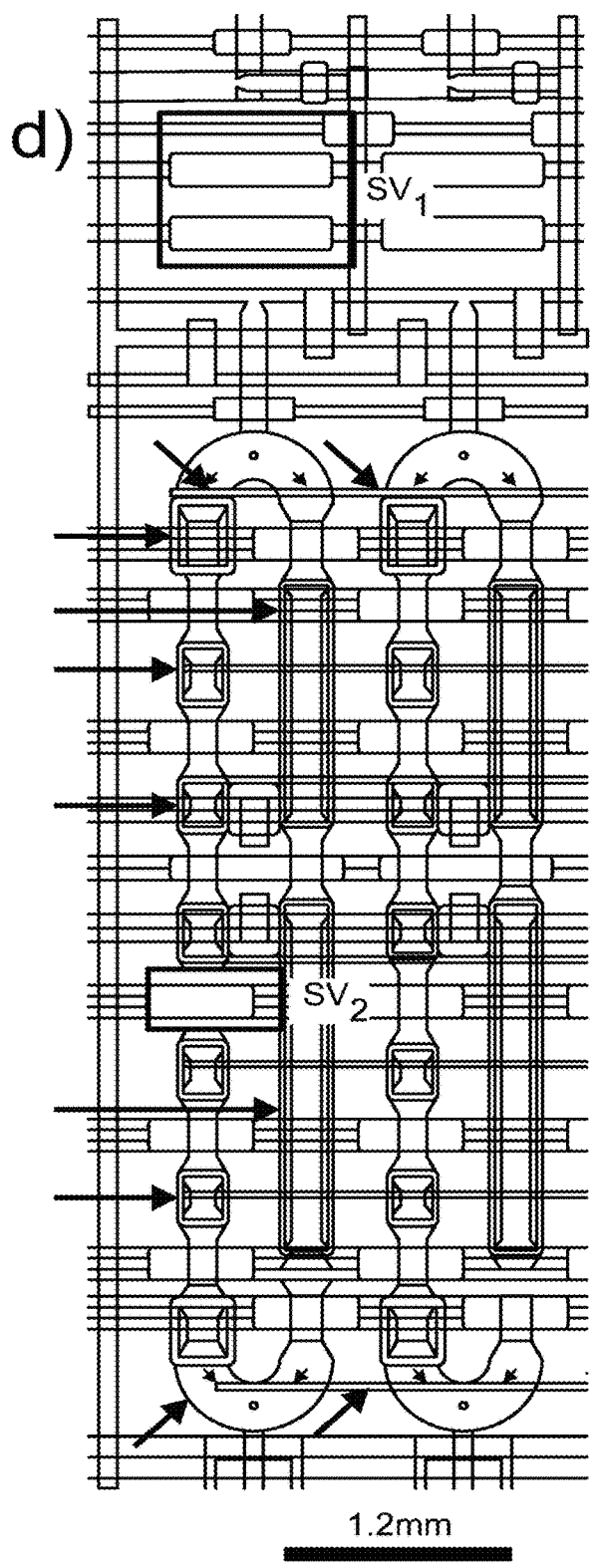

FIGS. 7A-7C show an illustrative diagram of a microfluidic device 700 and the associated input ports and output ports of the device, in accordance with an embodiment of the disclosure. Input port array 702 includes input ports, such as input port 704, and may function as inputs for any of the chemicals, enzymes, cells, capture substrates, components of a cell, or fluid described herein. Output ports, such as output port 706, may function as output for the components of the cell (processed or unprocessed) or for a sequence library. Alternatively, the output ports may function as input ports for chemicals, enzymes, cells, capture substrates, components of a cell, or fluid described herein. For example, the output port 706 may receive a barcode primer. Each input port 704 or output port 706 can be configured in a specific shape to couple with laboratory equipment such as a pipette or tubing.

Figure 8:
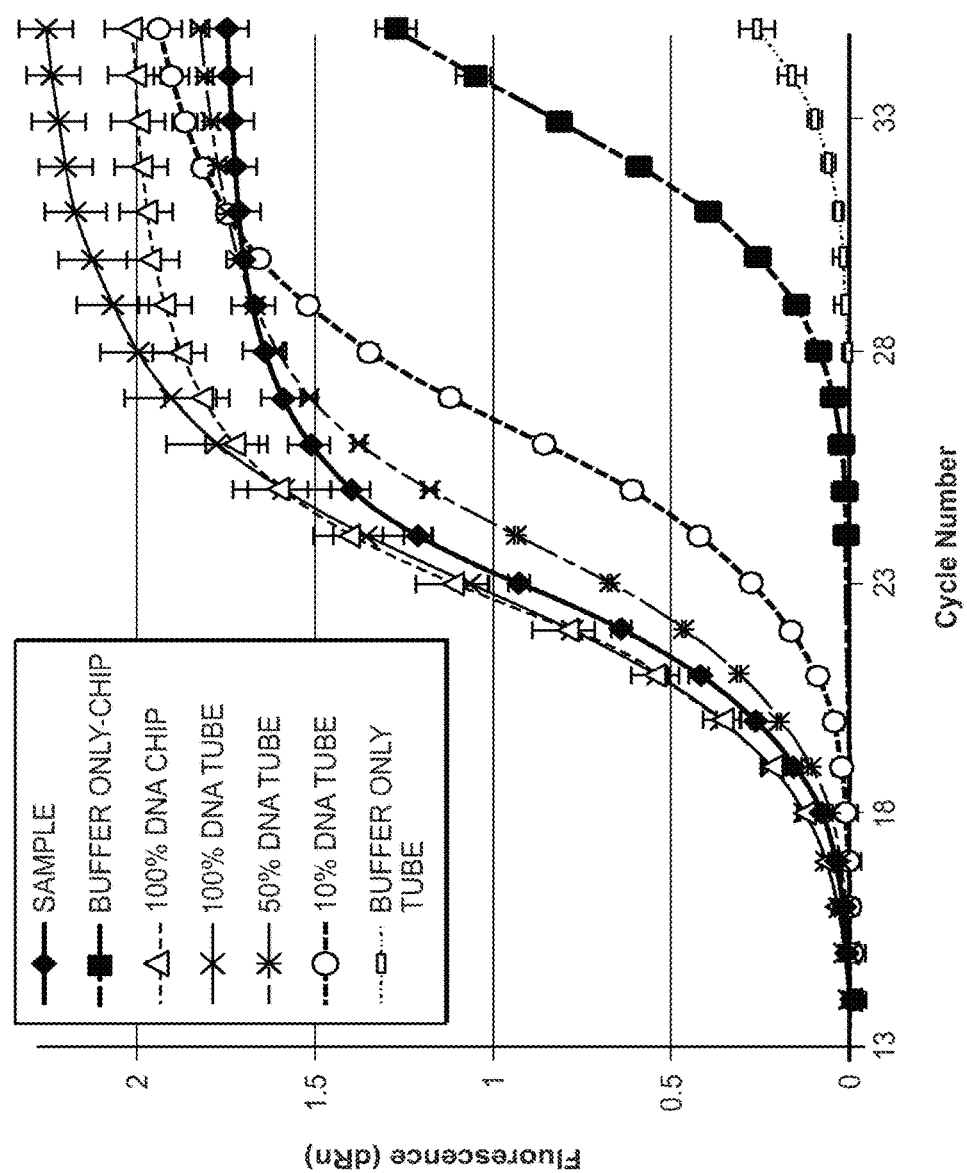
FIG. 8 shows a plot of data for concentrating DNA using a microfluidic device for capturing components of a cell, in accordance with an embodiment of the disclosure.

FIG. 8 shows a plot 800 of data for concentrating DNA using a microfluidic device for capturing components of a cell, in accordance with an embodiment of the disclosure. In this plot, the x-axis represents the amplification cycle (or PCR thermo cycle) and the y-axis represents the brightness of the DNA sample. This experiment was performed using a quantitative PCR technique. As can be seen from plot 800, the fluorescence of each DNA sample increases with each PCR amplification cycle. Specifically, samples of DNA that are concentrated outside of the microfluidic device and samples of DNA that are concentrated inside the device begin to fluoresce after a substantially similar number of PCR cycles (e.g., within 5 cycles of each other). Plot 800 also shows that a higher DNA starting quantity results in a fluorescence signal occurring at an earlier cycle. The negative control experiment, using a microfluidic chip and no DNA, begins to fluoresce at a later cycle, providing data that the microfluidic chip is capable of purifying DNA.

Figure 9:
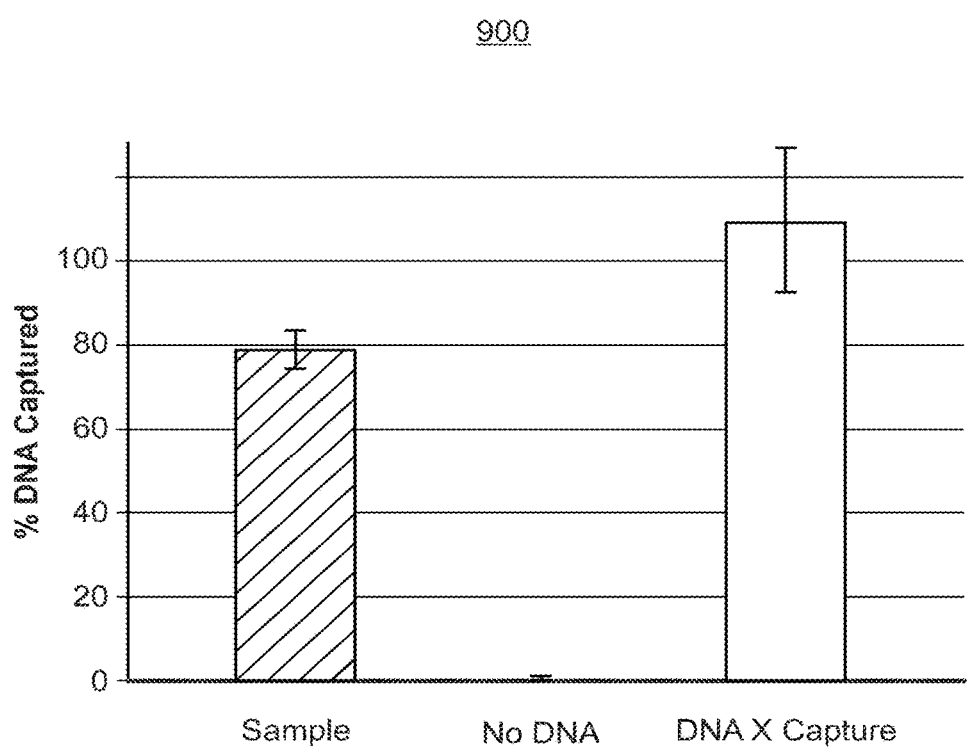
FIG. 9 shows a plot of preliminary data for DNA capture efficiency using a microfluidic device for capturing components of a cell, in accordance with an embodiment of the disclosure.

FIG. 9 shows a plot 900 of preliminary data for DNA capture efficiency using a microfluidic device for capturing components of a cell, in accordance with an embodiment of the disclosure. This preliminary data demonstrates that capture and elution efficiencies of 80-100% can be achieved using the microfluidic device and methods described herein to capture components of a cell, such as DNA. In the test experiments that provided the data for the plot 900, *E. coli* genomic DNA was used as a proxy for microbial genomic DNA. The capture efficiency was measured using a quantitative PCR technique.

Figure 10:
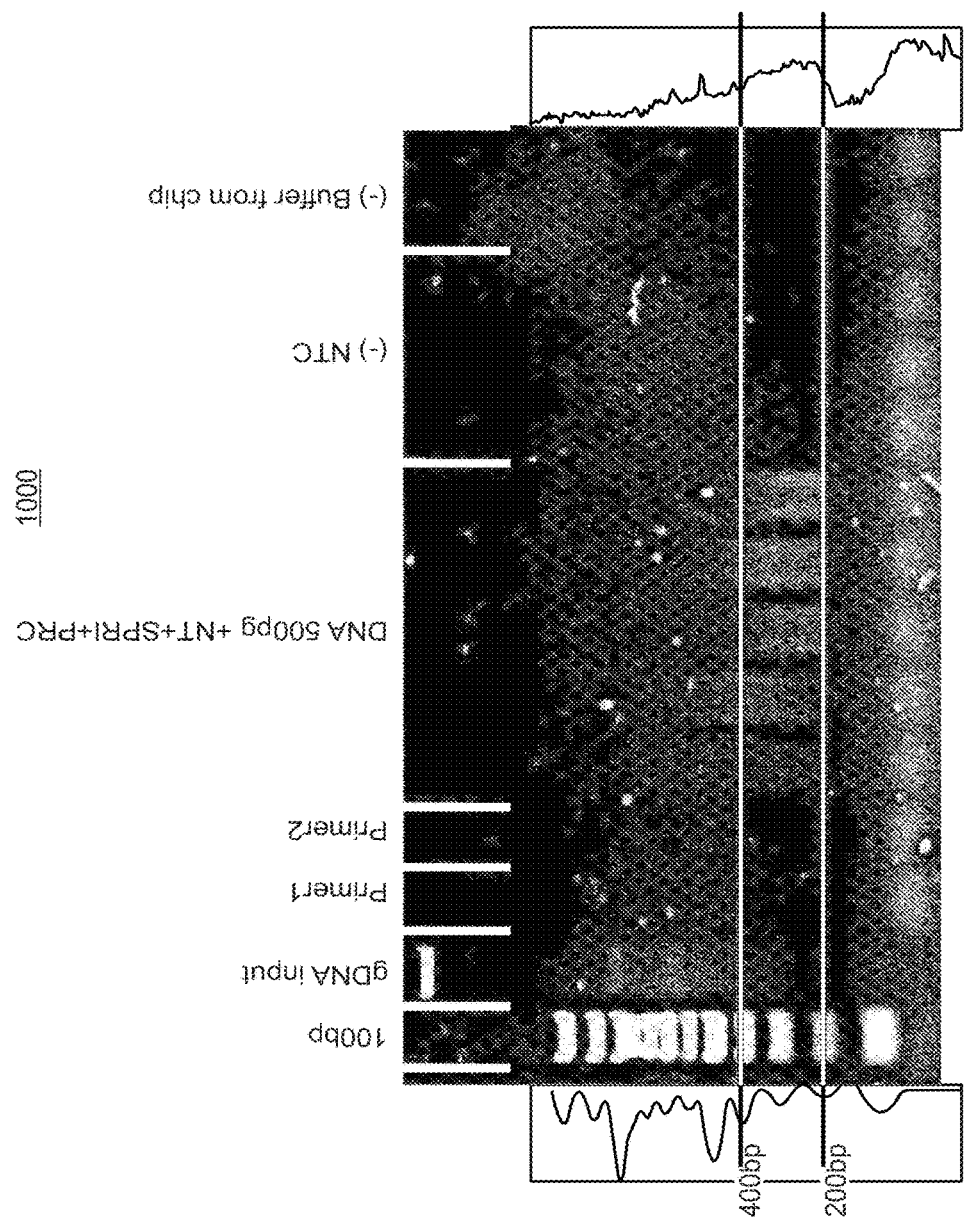
FIG. 10 shows a plot of DNA fragment sizes after processing genomic DNA in a microfluidic device, in accordance with an embodiment of the disclosure.

FIG. 10 shows a plot 1000 of DNA fragment sizes after processing genomic DNA in a microfluidic device. Plot 1000 shows five repeated bands in the segment labeled "DNA 500 pg+NT+SPRI+PCR" that are between approximately 200 base pairs and approximately 400 base pairs when compared to a 100 base pair reference ladder. Each of the five bands corresponds to a respective reactor on a microfluidic device. Each reactor may correspond to a microfluidic device 100 as described above with respect to FIG. 1. Plot 1000 also shows that no residual DNA fragments were detected in the negative controls: no-template control (NTC) and buffer flow-through from the device. Three reactors were used to test the no-template control and two reactors were used to test the buffer flow-through. This data demonstrates that the microfluidic device can effectively fragment genomic DNA to a predetermined size or range of sizes, in addition to demonstrating the ability to clean out the device for reuse. The size of the DNA fragments can be altered by changing the ratio of capture substrate to activation chemical. The capture substrate can bind a specific size or range of sizes of fragmented DNA while the rest of the uncaptured DNA fragments are washed out of the microfluidic device.

Figure 11:
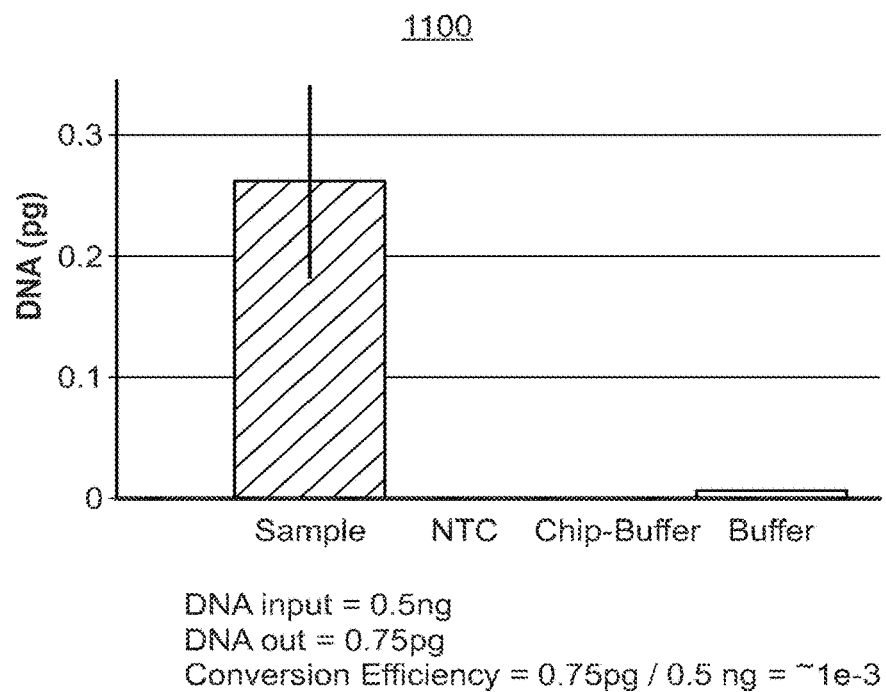
FIG. 11 shows a plot of library conversion efficiency of the NEXTERA® process in a microfluidic device, in accordance with an embodiment of the disclosure.

FIG. 11 shows a plot 1100 of library conversion efficiency of the NEXTERA® process in a microfluidic device, in accordance with an embodiment of the disclosure. In this experiment, approximately 500 pg of genomic DNA was used as input DNA to a microfluidic device. After processing the genomic DNA using any of the methods described herein, approximately 0.7 pg of fragmented and adaptor tagged DNA was collected. To quantify the amount of fragmented and adaptor tagged DNA, quantitative PCR was used. The resulting conversion efficiency in a microfluidic device was calculated to be approximately $10^{-3}$.

Figure 12:
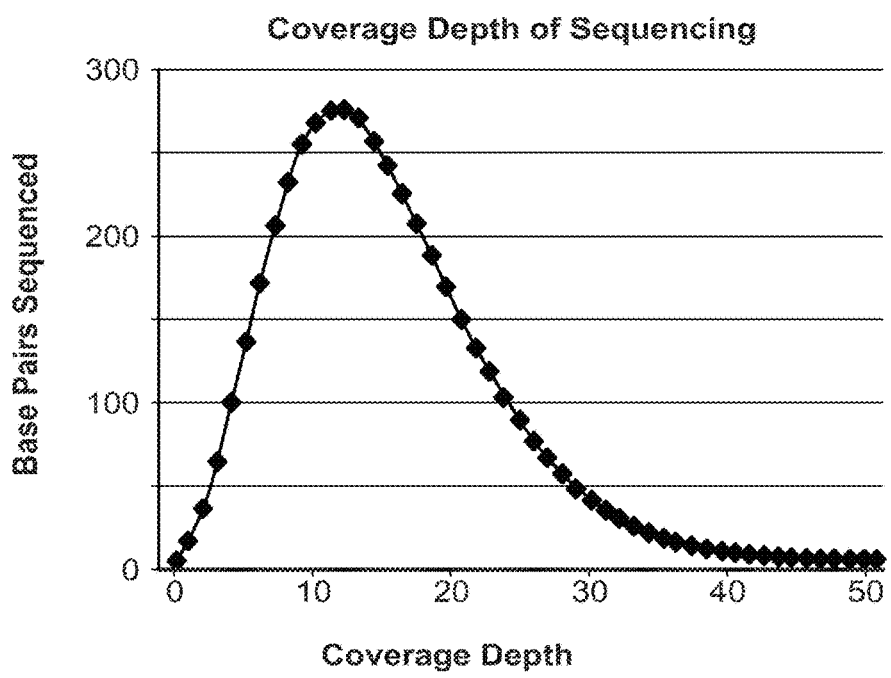
FIG. 12 shows a plot of coverage depth of a sequenced DNA library that was prepared in a microfluidic device, in accordance with an embodiment of the disclosure.

FIG. 12 shows a plot 1200 of coverage depth of a sequenced DNA library that was prepared in a microfluidic device, in accordance with an embodiment of the disclosure. In this experiment, a DNA library of an *E. coli* MG1655 genome was prepared in a microfluidic device and sequenced using a MiSeq sequencer. A 2×25 read length and 1.3 million reads were used as parameters for this experiment. A 99.9% genome coverage was achieved with a mean coverage depth of 14.6× and 98.5% of the fragments aligned with a reference MG1655 *E. coli* genome. After sequencing a DNA library that was prepared using a microfluidic device or any of the methods as described herein, the resulting coverage depth was within an acceptable range having a mean coverage depth of approximately 14.6×. A higher coverage depth may provide greater certainty of the base pairs comprising the genomic DNA.

Figure 13:
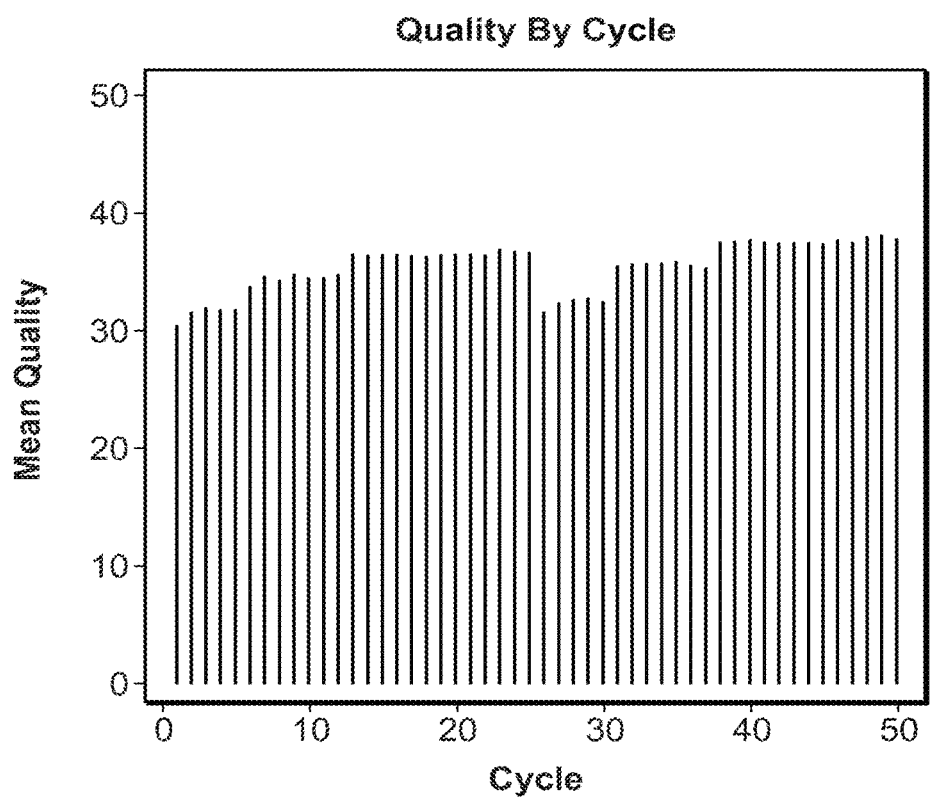
FIG. 13 shows a plot of a quality score of each sequencing cycle for a sequenced DNA library that was prepared in a microfluidic device, in accordance with an embodiment of the disclosure.

FIG. 13 shows a plot 1300 of a quality score of each sequencing cycle for a sequenced DNA library that was prepared in a microfluidic device, in accordance with an embodiment of the disclosure. Plot 1300 may correspond to a Phred quality score, although any suitable quality score can be used as a metric to measure accuracy of sequencing results. Plot 1300 demonstrates that an acceptable quality (e.g., a score above 20) can be achieved for each sequencing cycle performed on a DNA library prepared using a microfluidic device and/or any of the methods as described herein. The quality scores shown in FIG. 13 are greater than or equal to 30, which corresponds to a base call accuracy of greater than or equal to 99.9% in a Phred quality score.

Figure 14:
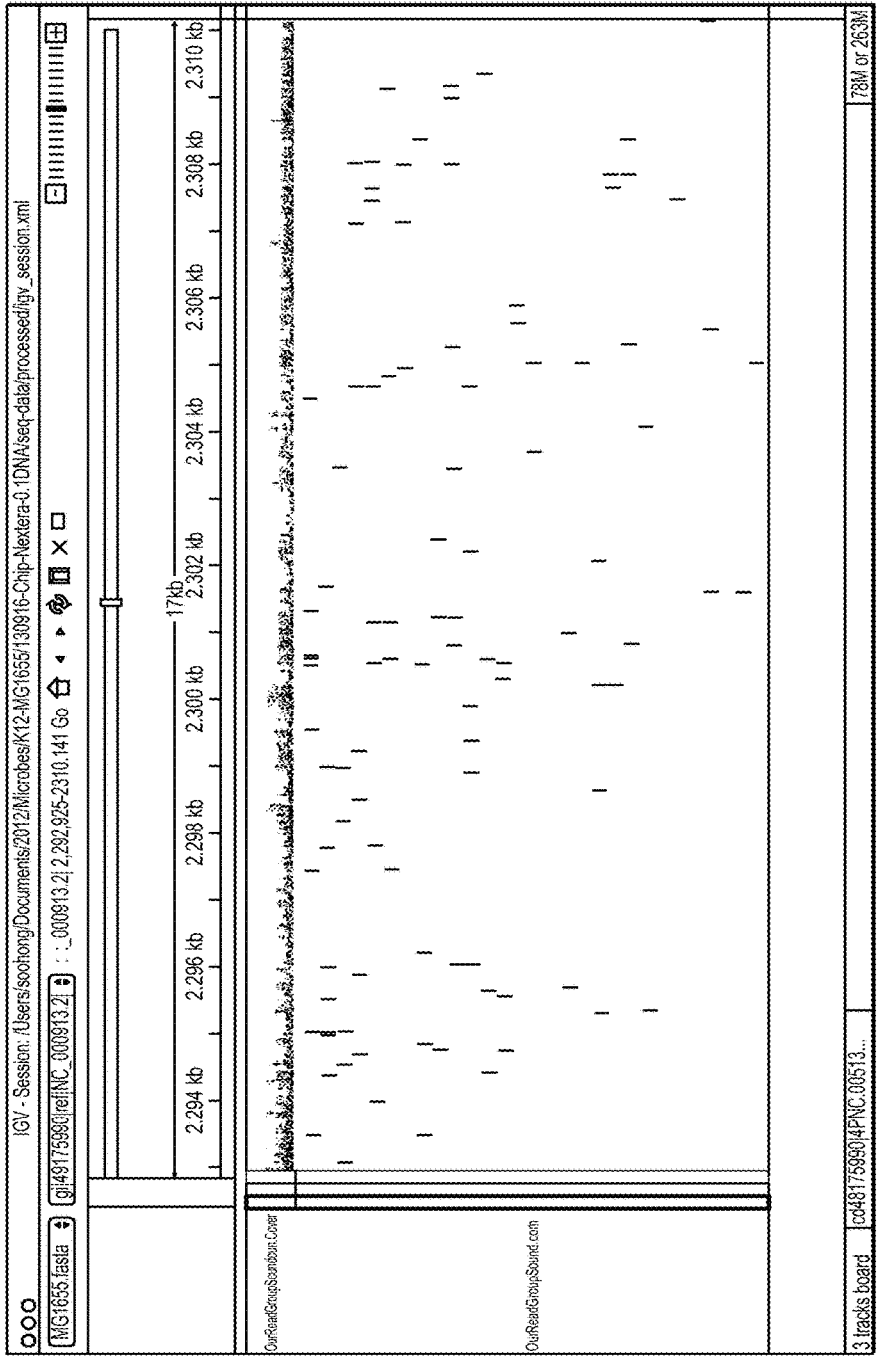
FIG. 14 shows a plot of genome position and sequencing depth for a sequenced DNA library that was prepared in a microfluidic device, in accordance with an embodiment of the disclosure.

FIG. 14 shows a plot 1400 of genome position and sequencing depth for a sequenced DNA library that was prepared in a microfluidic device, in accordance with an embodiment of the disclosure. Plot 1400 demonstrates resulting data obtained from a sequencing device for a DNA library that was prepared using a microfluidic device or any of the methods as described herein. The mean sequencing depth for this experiment was approximately 14.6×.

The microfluidic device generally disclosed herein can be used to capture or separate an analyte using any suitable capture or separation means. For example, the device may capture an analyte using a process including filtering, the use of optical tweezers, chemical processes, or a capture substrate that binds the analyte. In some embodiments, multiple microfluidic devices can be used in parallel to prepare samples of target components or for therapeutic applications such as dialysis. Increasing the number of microfluidic devices can be preferable to increasing the size of the microfluidic device for cheaper manufacturing costs. Accordingly, the present disclosure contemplates systems that comprise multiple microfluidic devices as disclosed herein. In some embodiments, the microfluidic device can be used to select or detect specific types of cells, such as circulating tumor cells (CTCs) rather than components of cells. Alternatively, the microfluidic device can be used for sample preparation or other handling or processing of blood or prenatal fluid.

Referring now to FIGS. 51A-D, an exemplary geometry for a sieve valve 5100 is depicted. As seen most clearly in FIG. 51A, sieve valves 5100 can be efficiently constructed using a crossing geometry in which valves 5100 are formed where control channels 5114 and fluid channels 5104 cross over each other in separate planes, separated by flexible membrane 5106. Such an approach confines the actuation of the flexible membrane 5106 to the area of overlap between the control channel 5114 and fluid channel 5104. Although a right angle is depicted, other angles could be used and the control channel 5114 can run parallel to and underneath the fluid channel 5104. In such a parallel embodiment, it may be desirable to reinforce or otherwise inhibit deflection of the flexible membrane 5106 in certain locations where actuation is not desired.

In order to trap, filter, collect, or otherwise retain one or more objects of interest within a fluid, embodiments of the invention can include a geometry that prevents or inhibits passage of one or more solid components when the valve 5100 is actuated to deflect the flexible membrane 5106 into the fluid channel 5104, while still allowing the fluid to pass through the valve 5100. Such a geometry can be described with reference to one or more protrusions 5108 and/or recesses 5112 opposite the flexible membrane 5106 so that the flexible membrane 5106 presses against the one or more protrusions 5108 to substantially restrict flow through the fluid channel 5104 except for where the flexible membrane 5106 does not press against the walls of the channel 5104 (e.g., within the recesses 5112).

Advantageously, the objects of interest are trapped within the fluid flow channel 5106 instead of being pushed into one or more lateral traps. The proposed geometry avoids the need to have sufficient trap space for a desired volume of objects of interest and can be more easily scale by extending the length of the fluid channel 5106 upstream from a sieve valve 5100. Additionally, the proposed geometry does not press the objects of interest laterally into a trap, which can damage fragile objects of interest such a cell. Moreover, liquids can more freely flow through the trapped objects of interest in the present invention than in systems using lateral traps that can introduce eddy currents or pockets of limited or no fluid flow.

In some embodiments, the protrusions 5108 or recesses 5112 extend beyond the intersection of the control channel 5114 and the fluid channel 5104. The protrusions 5108 or recesses 5112 can extend beyond the intersection on one side of the intersection (preferably, the upstream side from which fluid is anticipated to flow) or on both sides of the intersection (advantageously facilitating flow across the valve 5100 in either direction). For example, the protrusions 5108 or recesses 5112 can extend between about 10 µm and about 500 µm (e.g., greater than about 50 µm, greater than about 100 µm, greater than about 250 µm, and the like) beyond the intersection. Extension of the protrusions 5108 or recesses 5112 advantageously extends the interface between the protrusions 5108 or recesses 5112 and the fluid channel 5106 so that fluid can enter the recesses 5112 upstream from the intersection. Such an architecture enables higher flow rates, is less prone to premature clogging, and places less shear pressure on the objects of interest (e.g., cells) because the larger interface area will result in a lower pressure gradient across the valve 5100. As can be seen most clearly in FIG. 51C, at least some fluid moves through the three recesses 5112 as objects of interest are trapped upstream from the actuated valve 5100 instead of through the trapped objects of interest.

Figure 53A:
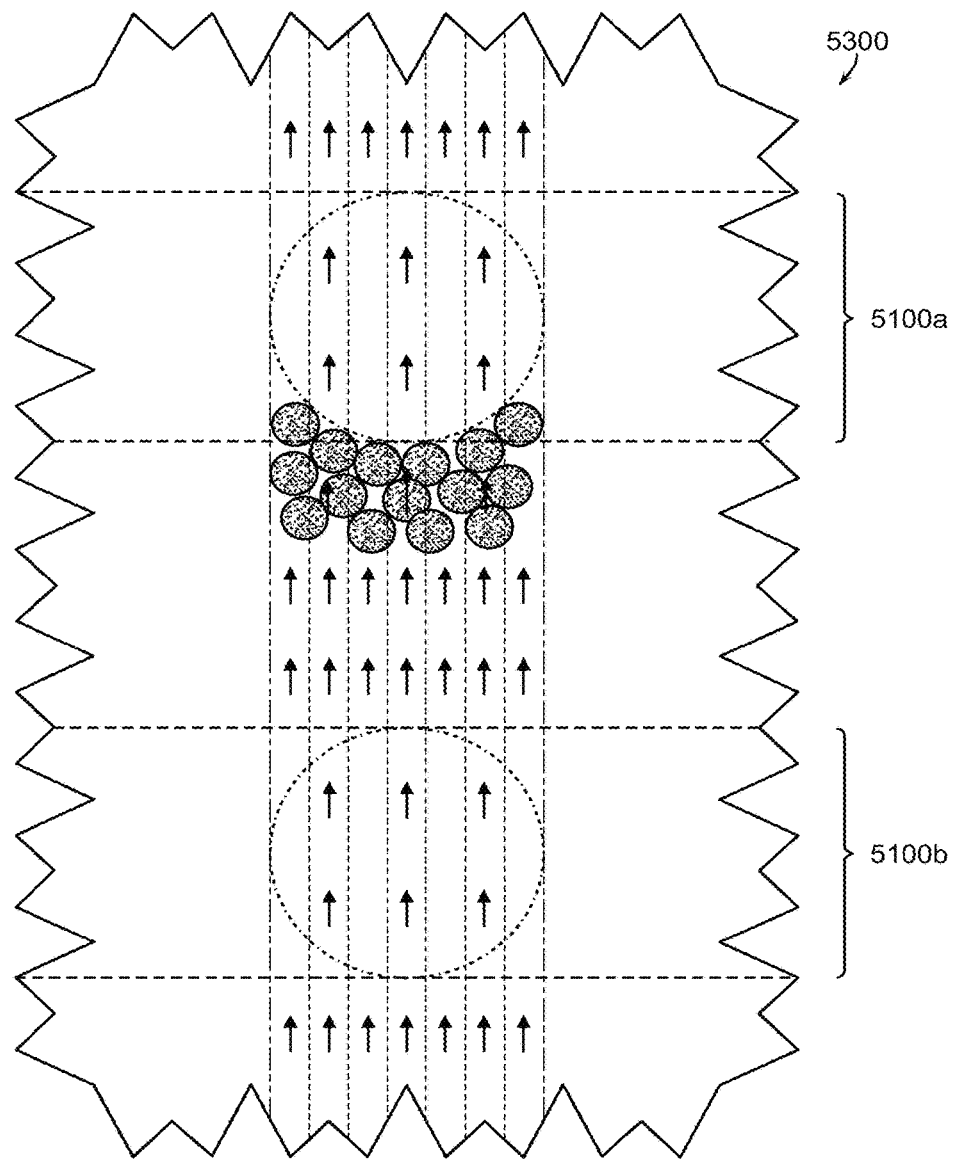
FIGS. 53A-53D depict a plurality of sieve valves positioned in series on a fluidic circuit according to an embodiment of the invention.
Figure 53B:
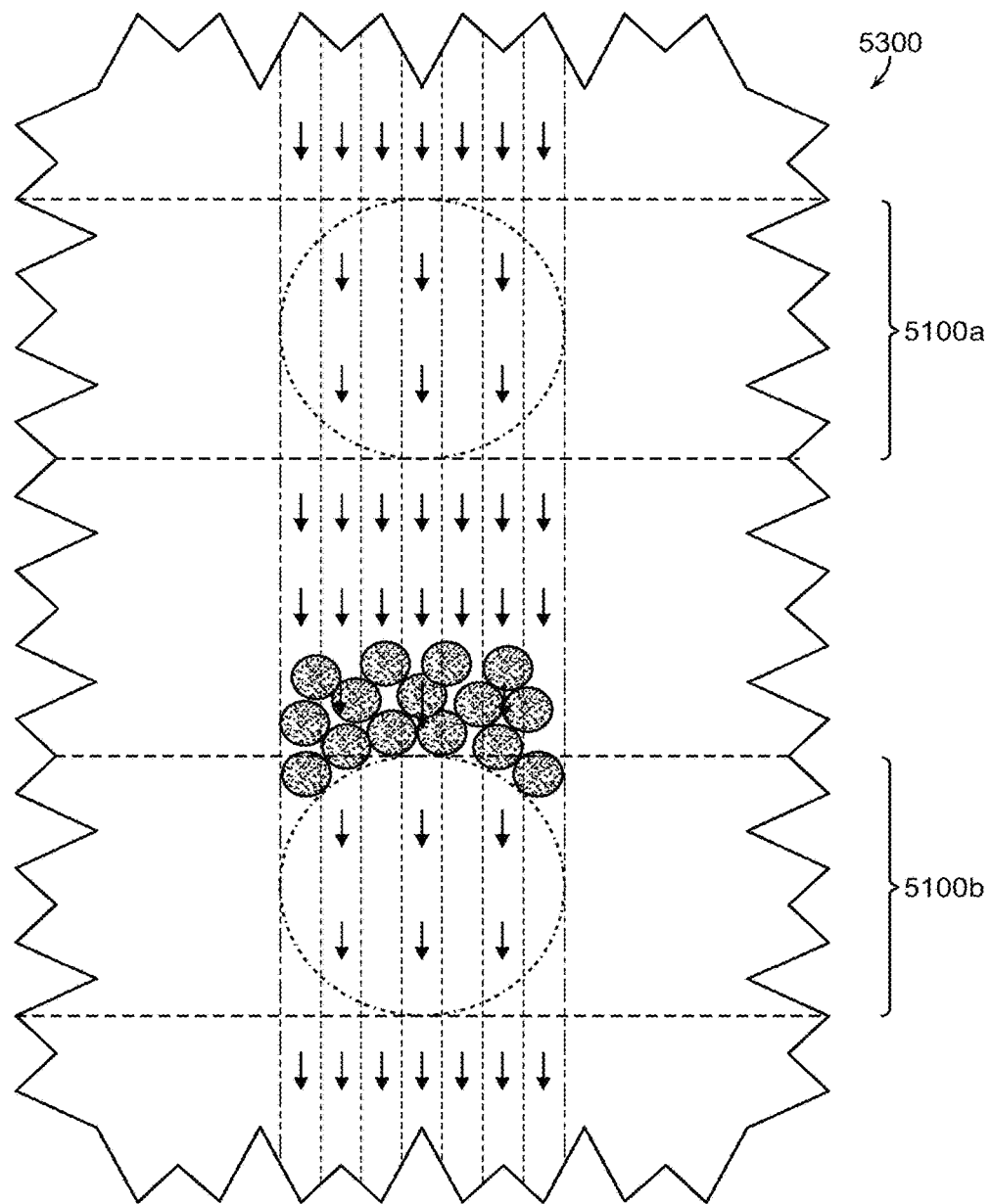

Referring now to FIGS. 53A and 53B, a plurality (e.g., 2) sieve valves 5100a, 5100b can be positioned in series on a fluidic circuit 5300. After objects of interest are trapped using the first sieve valve 5100a, the second sieve valve 5100b can be actuated to trap the objects of interest between the two sieve valves 5100a, 5100b. The fluid flow direction can then be reversed as depicted in FIG. 53B to flow fluid over the trapped objects of interest. The flow direction can be reversed a plurality of times. The fluid flowed over the trapped objects of interest can be the same or can be changed to achieve a desired outcome. For example, the fluid flows can be designed to rinse the objects of interest or expose the objects of interest. In another embodiment, the fluid flows can be designed to lyse the cells to release their contents.

Figure 53C:
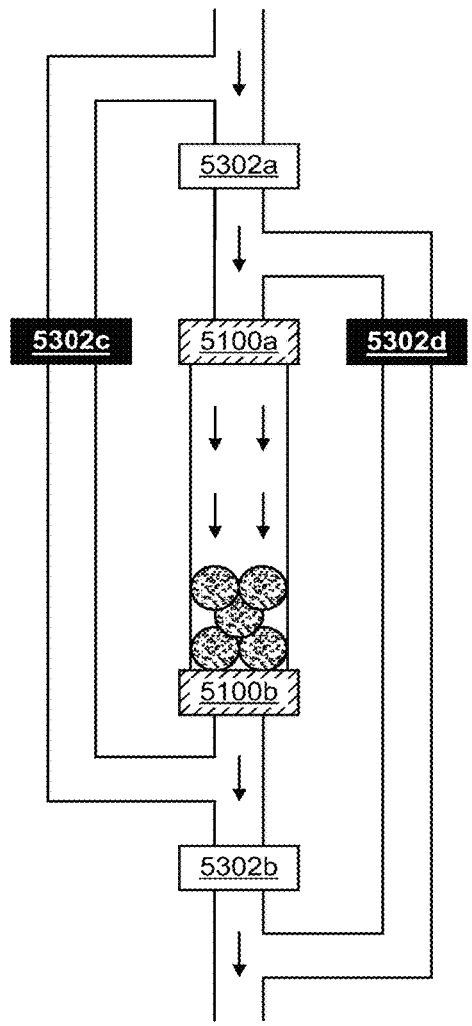
Figure 53D:
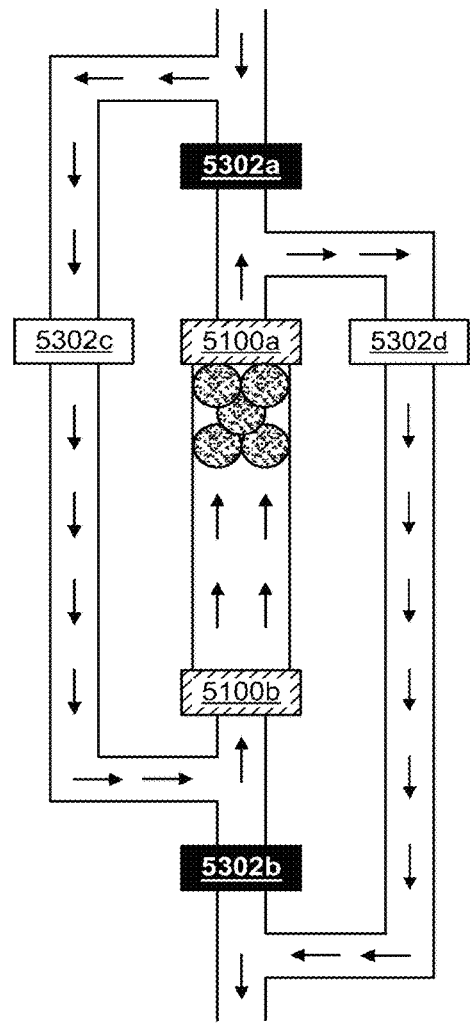

FIGS. 53C and 53D depict one exemplary valving arrangement for facilitating fluid in two directions across a pair of sieve valves 5100a, 5100b. Four on/off valves 5302a, 5302b, 5302c, 5302d that can completely or substantially interrupt fluid flow can be positioned as shown in FIGS. 53C and 53D. Suitable on/off valves are depicted and described in the context of FIG. 1A of U.S. Patent Application Publication No. 2012/0061305. As depicted in FIG. 53C, when valves 5302a and 5302b are actuated to an open position while valves 5302c and 5302d are actuated to a closed position, fluid flows through across the actuated sieve valves 5100a, 5100b in a first direction. As depicted in FIG. 53C, when valves 5302a and 5302b are actuated to a closed position while valves 5302c and 5302d are actuated to an open position, fluid flows through across the actuated sieve valves 5100a, 5100b in a second, opposite direction.

Figure 54:
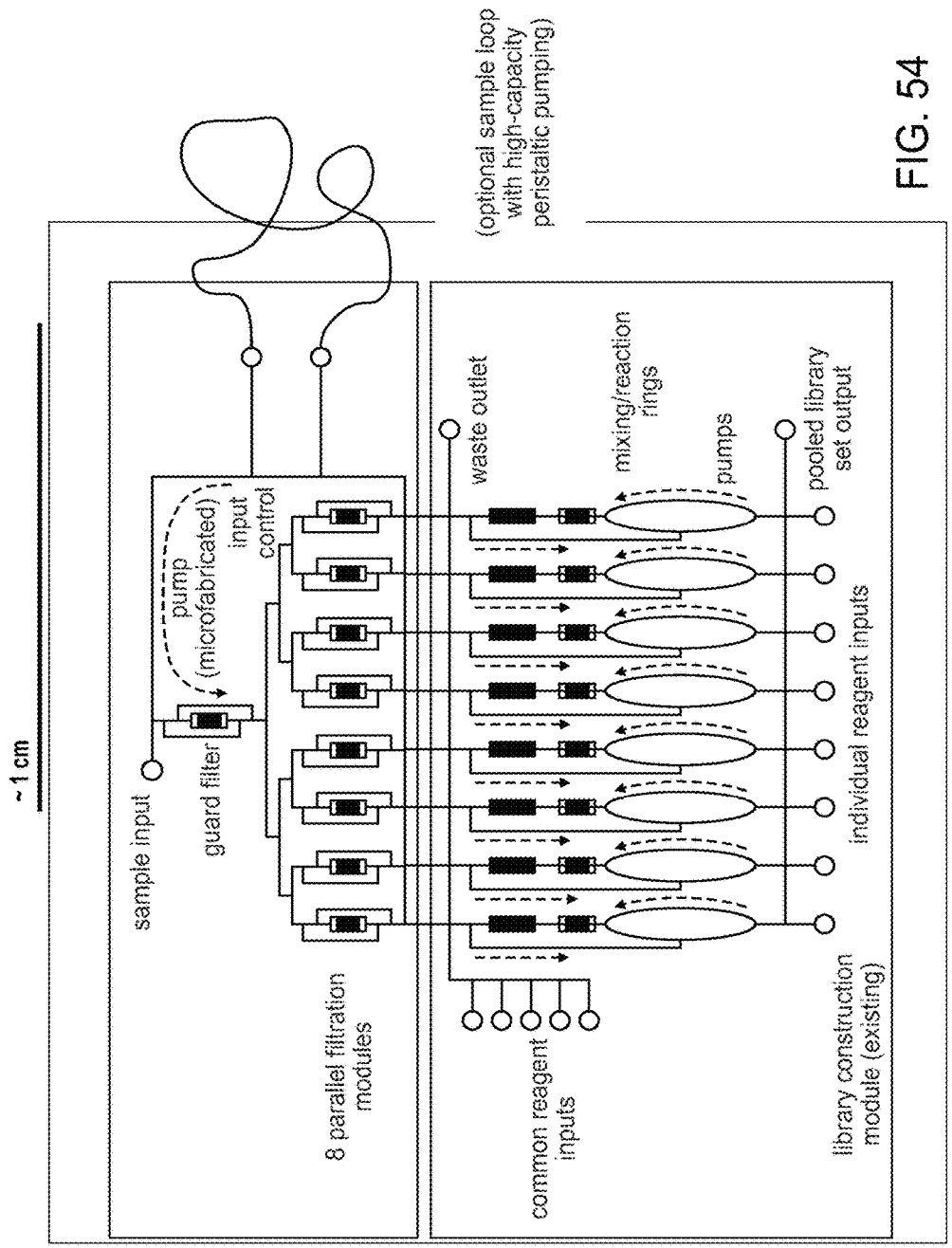
FIG. 54 depicts a chip sequencing device according to an embodiment of the invention.

Referring to FIG. 54, the valving arrangements depicted in FIGS. 53C and 53D can be incorporated within a chip sequencing device for parallel processing of inputs in accordance with the protocols discussed herein.

Figure 51A:
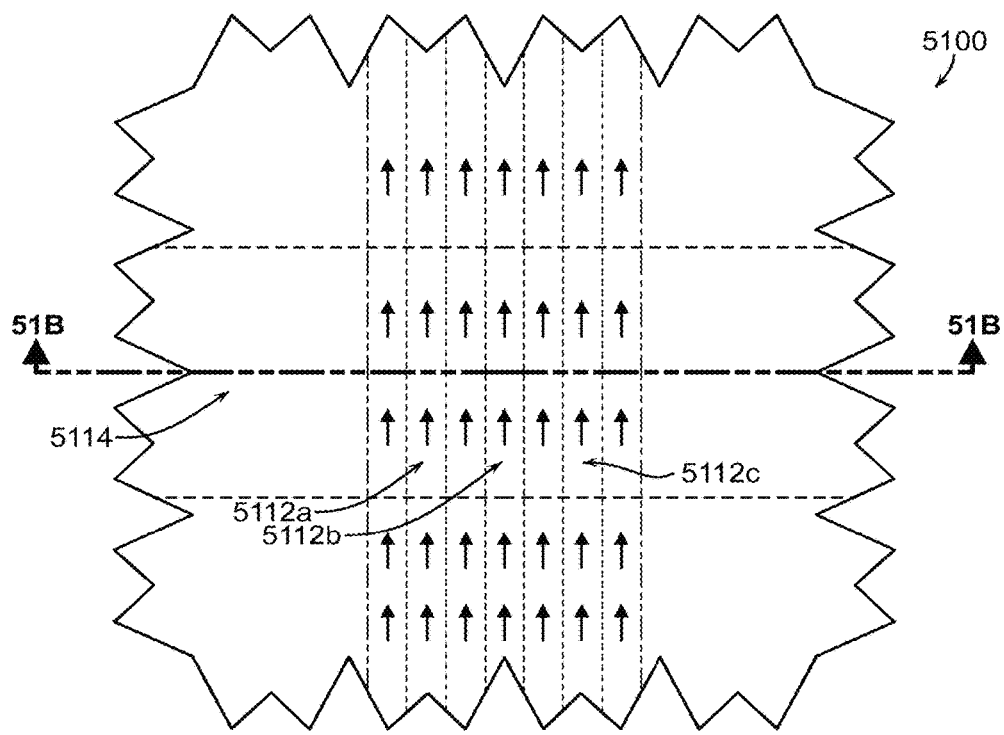
FIGS. 51A-51F depict an exemplary geometry for a sieve valve according to an embodiment of the invention.
Figure 51B:
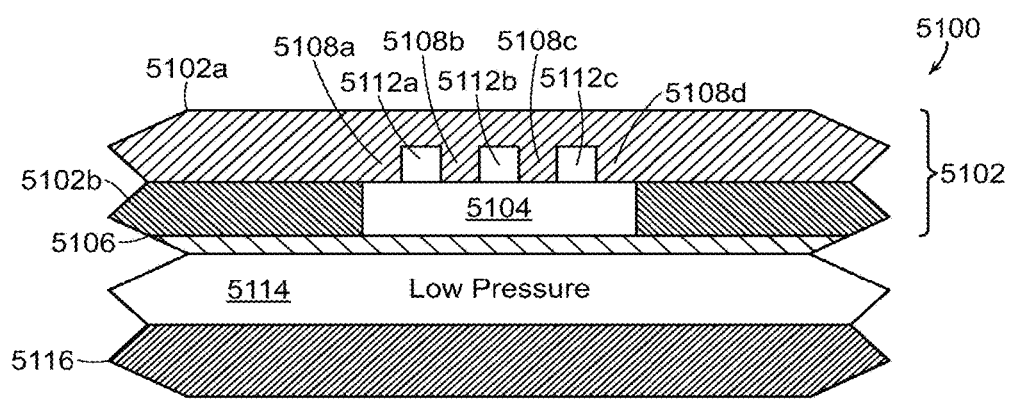
Figure 51C:
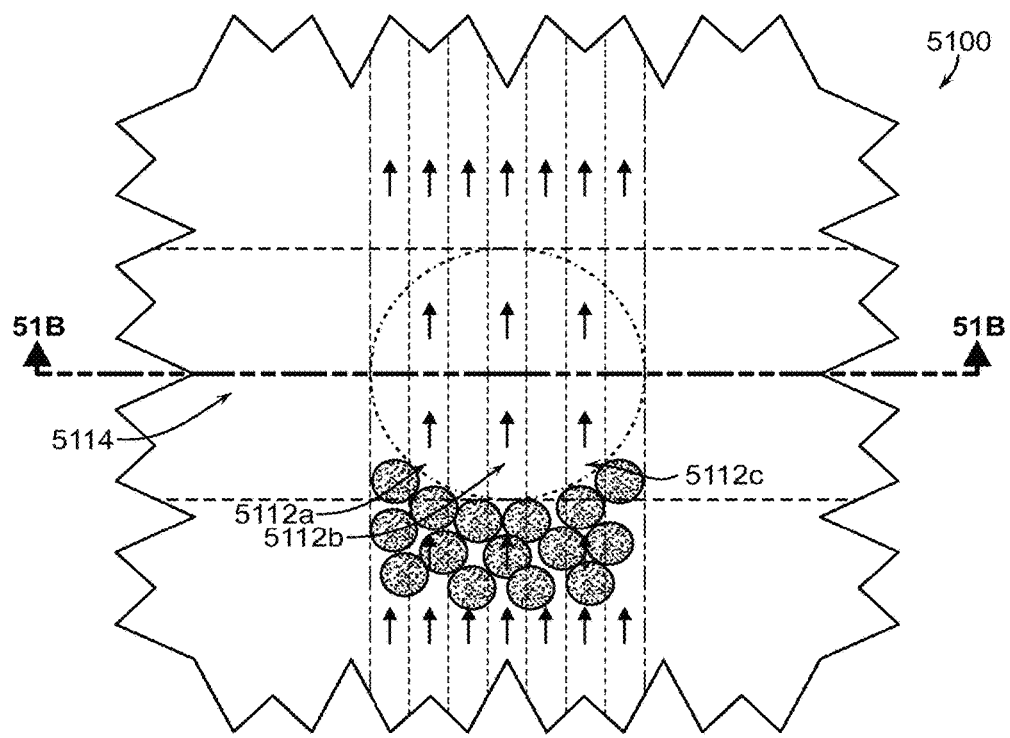
Figure 51D:
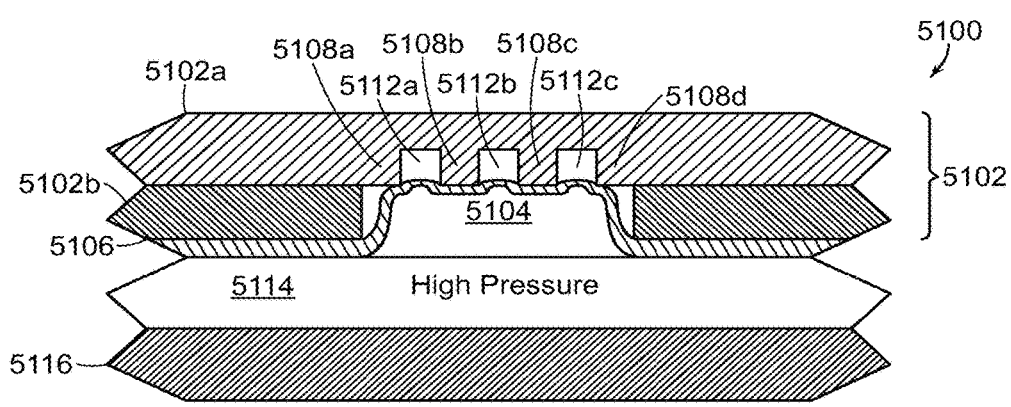
Figure 51E:
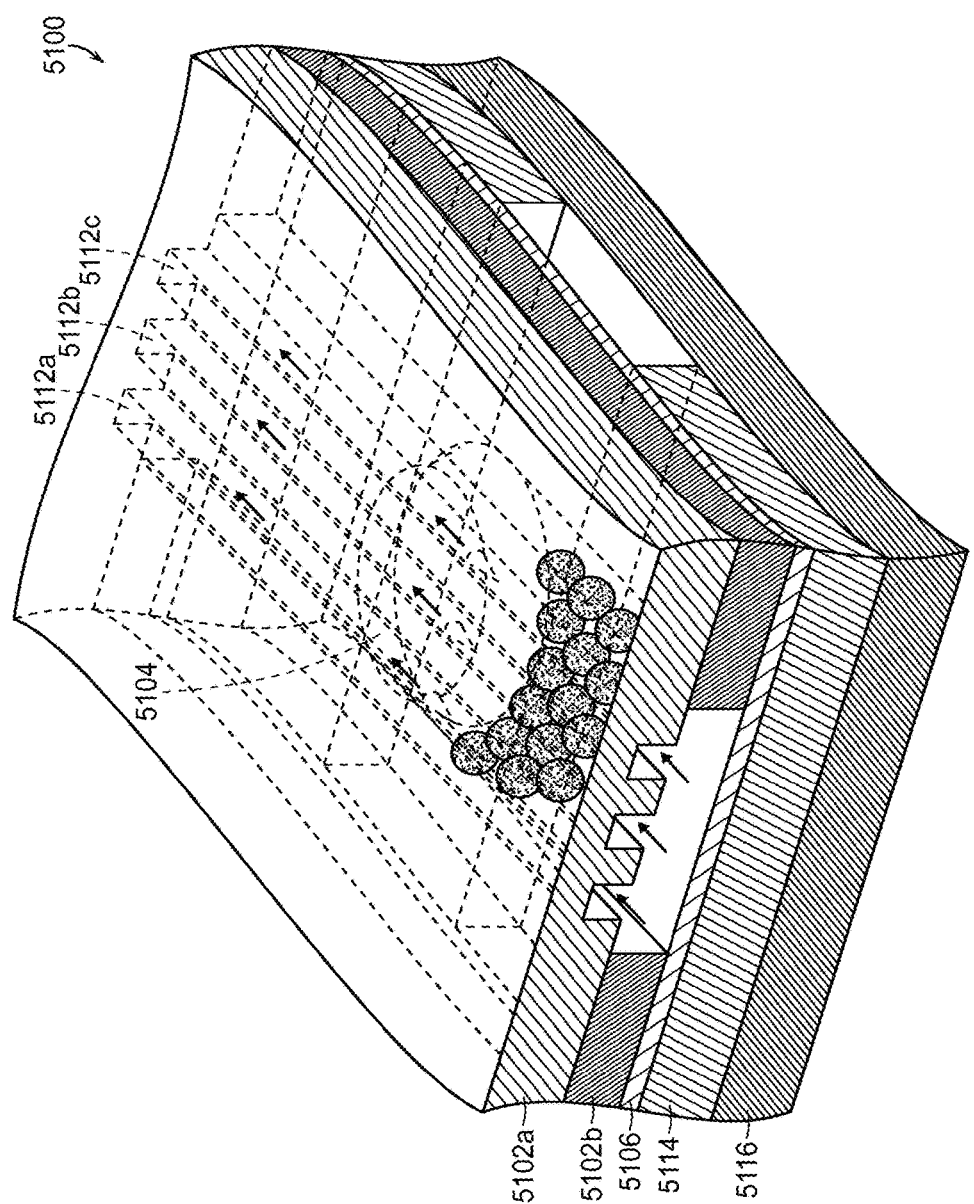
Figure 51F:
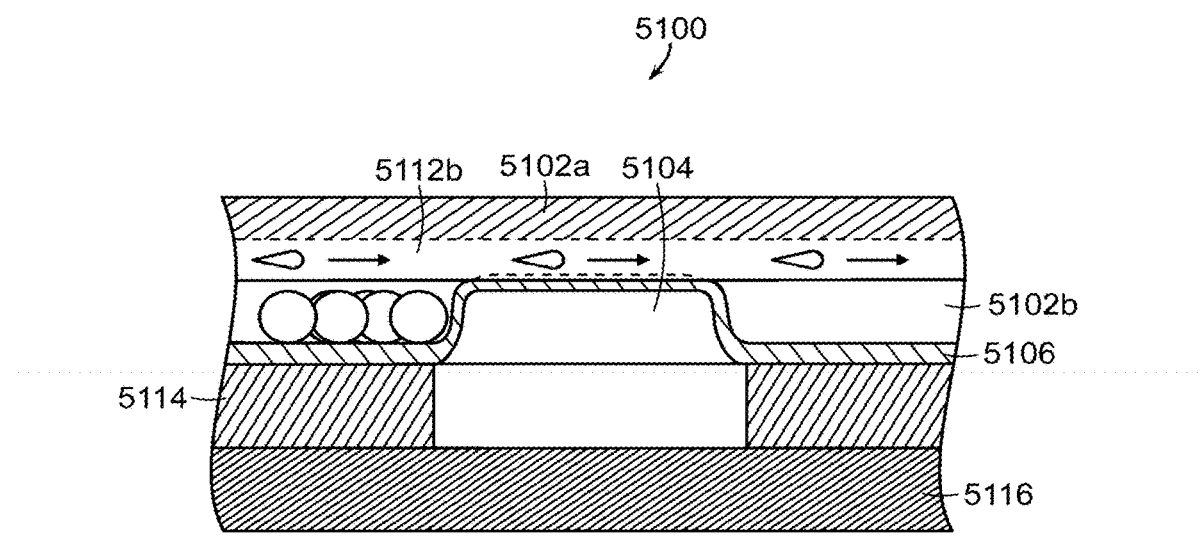

Substrate 5102 can be composed of a plurality (e.g., two) layers 5102a, 5102b as depicted in FIGS. 51E and 51F. Such a construction can facilitate fabrication of the protrusions 5108 and/or recesses 5112 adjacent to the flow channel 5104, as the structures 5108/5112 and 5104 can be fabricated in separate layers.

Figure 52A:
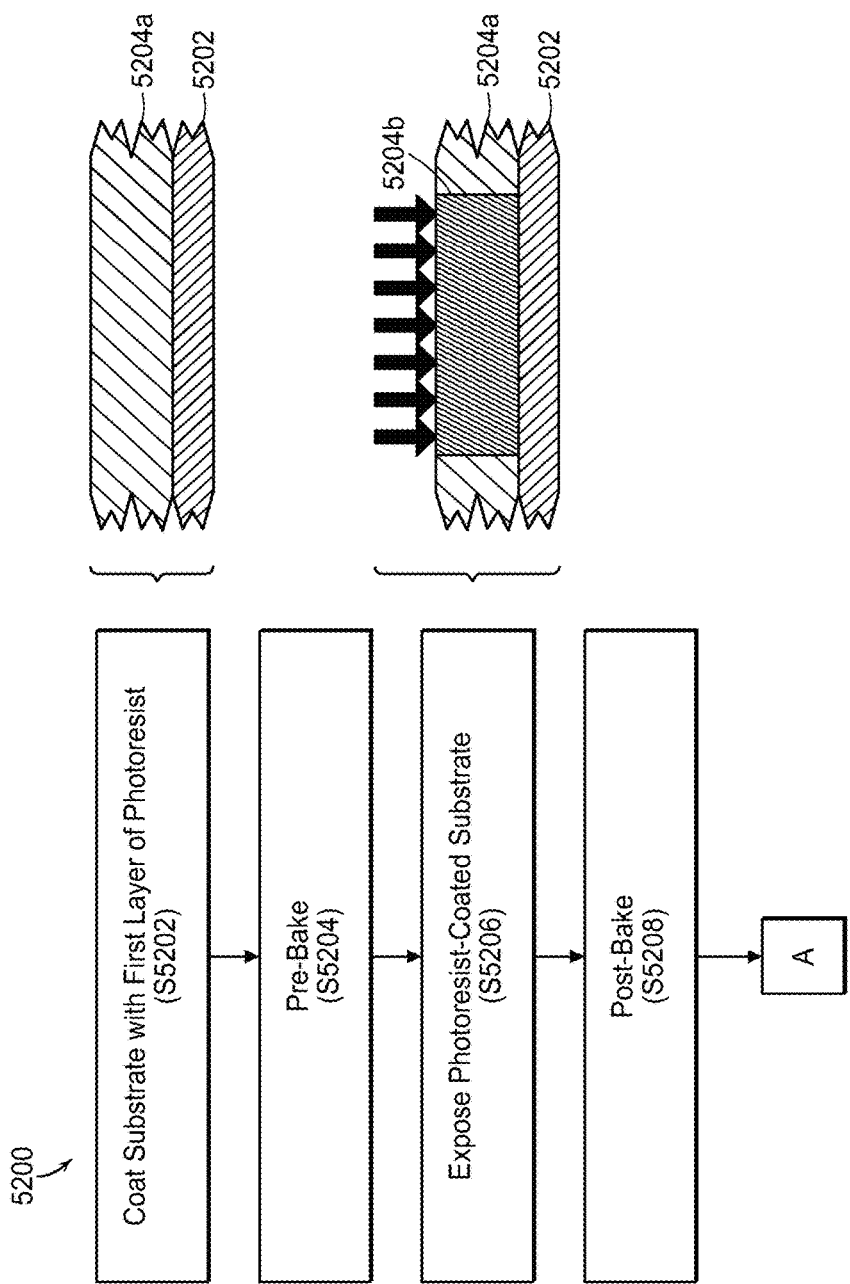
Figure 52B:
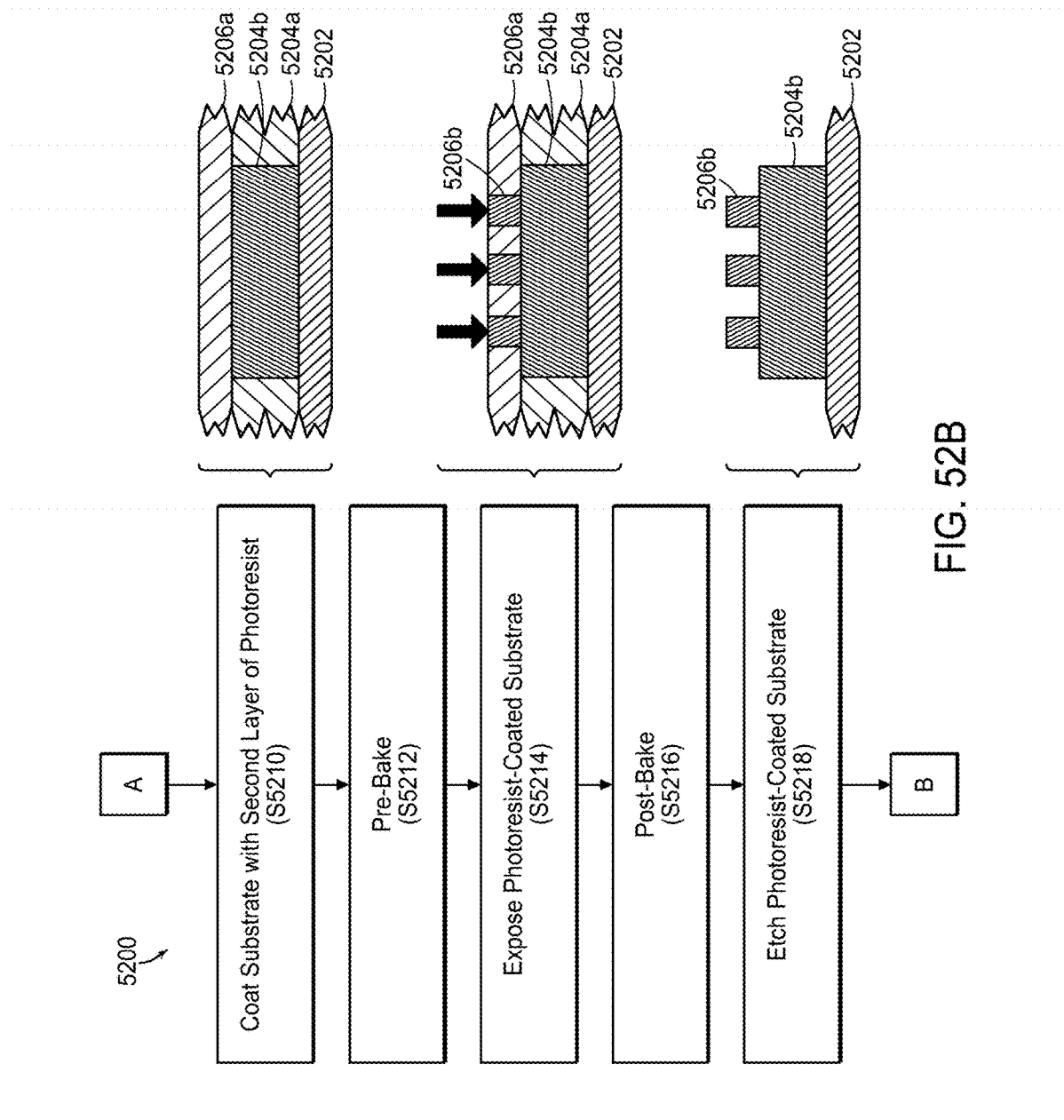

FIGS. 52A-52C depict a method 5200 of fabricating a microfluidic device.

In step S5202, a substrate 5202 is coated with a first layer of photoresist 5204a. Suitable substrates include polymers such as fully-cured polymer thin films, silicon, and the like. Suitable photoresists include SU-8, poly(methyl methacrylate) (PMMA), poly(methyl glutarimide) (PMGI), phenol formaldehyde resin, and the like and are available from a variety of manufacturers including AZ Electronic Materials USA Corp. of Branchburg, N.J. The photoresist can be spun, sprayed, or otherwise deposited onto the substrate using various known techniques.

In step S5204, the photoresist-coated substrate is pre-baked to evaporate the photoresist solvent. Relatively low temperatures (e.g., between about 90° C. to about 100° C.) and durations (e.g., between about 30 seconds to about 60 seconds) can be sufficient depending on the amount of photoresist applied to the substrate.

In step S5206, the photoresist-coated substrate is exposed to light to cross-link desired regions 5204b of the first layer of photoresist 5204a. For example, a mask can be used to protect regions of the first layer of photoresist 5204a to be removed from cross-linking.

In step S5208, the photoresist-coated substrate can be post-baked (also called hard-baking) according to the manufacturer's specification to solidify the remaining photoresist. For example, the photoresist-coated substrate can be baked at between 120° C. to about 180° C. for between about 20 minutes to about 30 minutes.

Steps S5202, S5204, S5206, and S5208 can be repeated one or more times as depicted in steps S5210, S5212, S5214, and S5216 to add and pattern additional layers of photoresist (e.g., a second layer 5206a). The additional layers of photoresist can be the same as or similar to the first layer of photoresist 5204a. For example, different viscosities of photoresist can be used for each layer in order to achieve the desired thicknesses in conjunction with selection of an appropriate spin rate. For example, SU-8 2015 can be used to produce a first layer 5204a having a thickness of about 15 µm and SU-8 2001 can be used to produce a second layer 5206a having a thickness of about 3 µm to about 5 µm.

In step S5218, the photoresist-coated substrate can be etched. In some embodiments, the etching removes an equal thickness of the photoresist and the substrate. A variety of etching techniques are available including "wet" etches that utilize liquid and "dry" etches that utilize plasma. The etching techniques can be isotropic or anisotropic. In one embodiment, deep reactive-ion etching (DRIE) is used.

In step S5220, the etched photoresist is used as a mold for casting a substrate for use in a sieve valve. Suitable casting materials include polymers such as silicones (e.g., polydimethylsiloxane or PDMS).

In step S5222, the cast substrate 5208 is removed from the mold. In step S5224, the cast substrate 5208 can be affixed to a layer 5210 of a sieve valve or a microfluidic device (e.g., flexible membrane 5106).

Figure 15A:
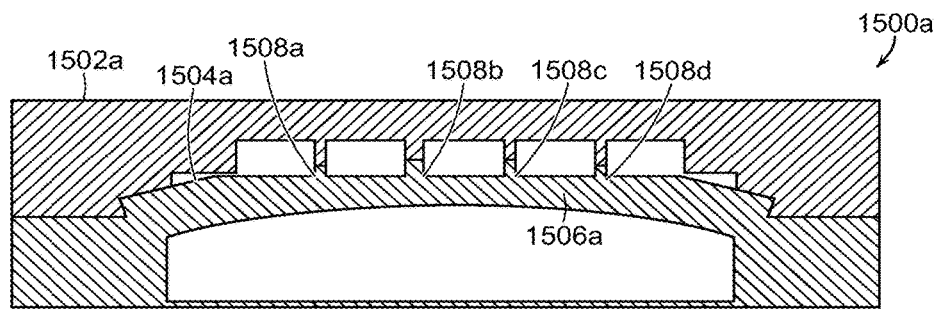
FIGS. 15A and 15B depict toothed sieve valves in accordance with an embodiment of the disclosure.

Referring now to FIG. 15A, another aspect of the invention provides a toothed sieve valve 1500a (a cross-section of which is shown in an actuated state). Sieve valve 1500a includes a substrate 1502a defining a channel 1504a and a flexible membrane 1506a. One or more protrusions 1508a extend from the substrate into the channel 1504a.

Figure 15B:
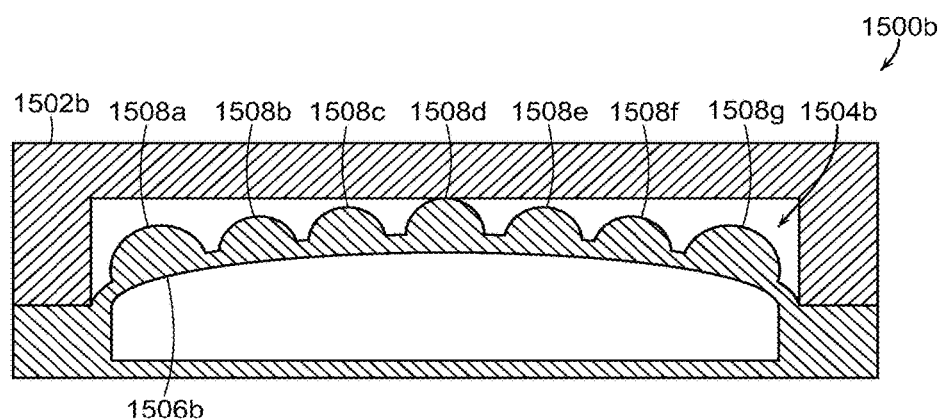

FIG. 15B depicts an alternative embodiment of a toothed sieve valve 1500b (a cross-section of which is shown in an actuated state). Protrusions 1508 extend from flexible membrane 1506b instead of channel 1504b. In some embodiments, protrusions 1508 can extend from both channel 1504 and flexible membrane 1506.

Substrate 1502 can be formed by photolithography. Negative master molds can be fabricated from photoresist and patterned using masks.

Protrusions 1508 can have a variety of profiles. Preferably, protrusions 1508 lie within the same plane with respect to a cross-section of channel 1504 and/or flexible membrane 1506.

Sieve valve 1500 can have any number of protrusions. For example, the number of protrusions can be selected based on the dimensions of the channel, the objects to be retained by the sieve valve, and the manufacturing capabilities of a particular device. For example, if manufacturing permits the construction of materials at a 5 µm resolution and the channel is 45 µm wide, 5 protrusions having a width of 5 µm can be provided with 5 µm inter-protrusion-spacing.

Protrusion size and spacing can be further optimized based on the desired fluids, samples, capture substrates, pressures, and other parameters affecting flow rates.

Toothed sieve valves 1500 can be fabricated from the same materials and actuated in the same manner as sieve valve 200 discussed herein.

Figure 16A:
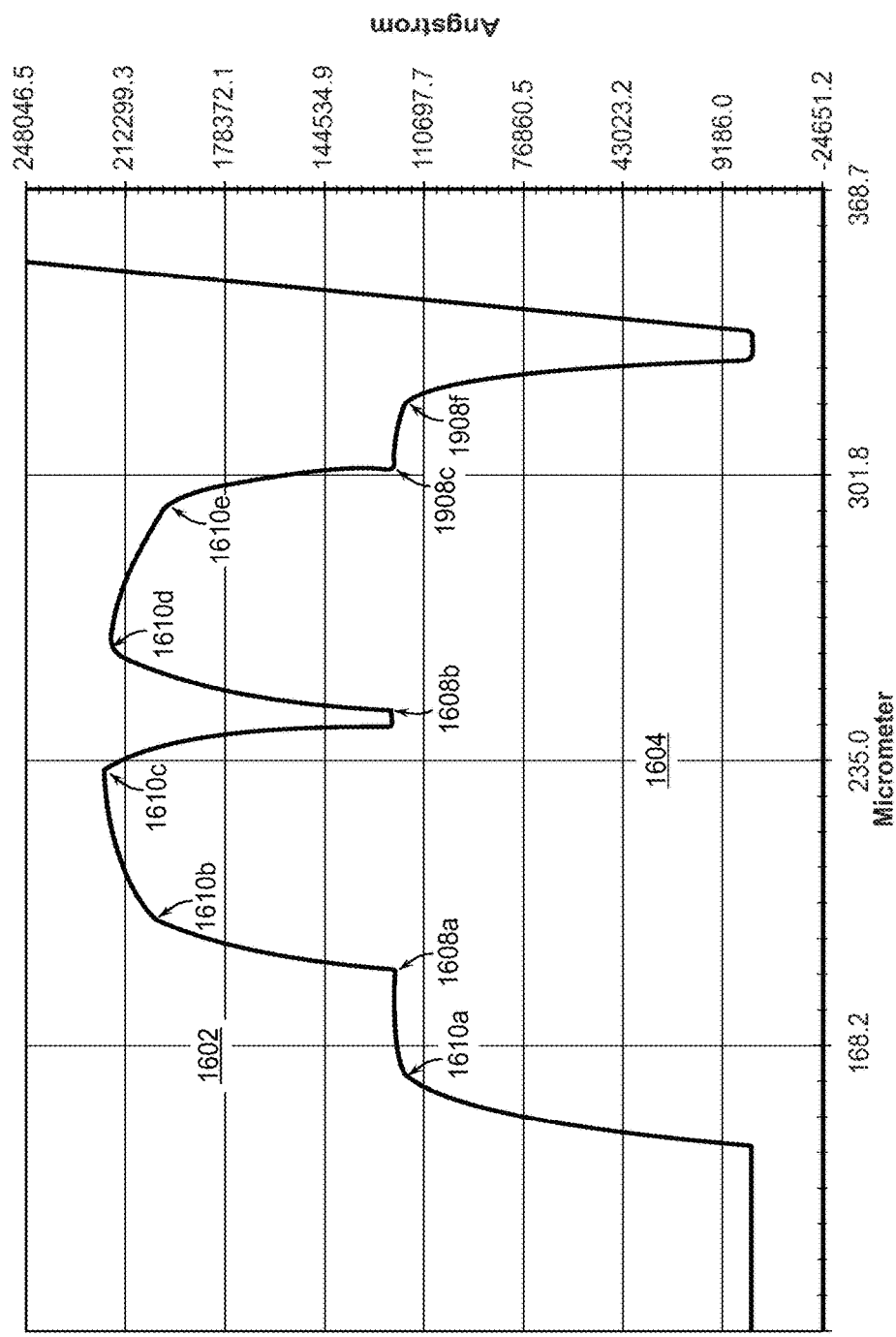
FIG. 16A depicts the cross-section of a channel in accordance with an embodiment of the disclosure.

Referring now to FIG. 16A, a cross-section of a channel 1604 formed within a substrate 1602 is illustrated. Ridges 1508a-c produce a plurality of corners 1510 that will not be occluded when a flexible membrane is deployed.

Figure 16C:
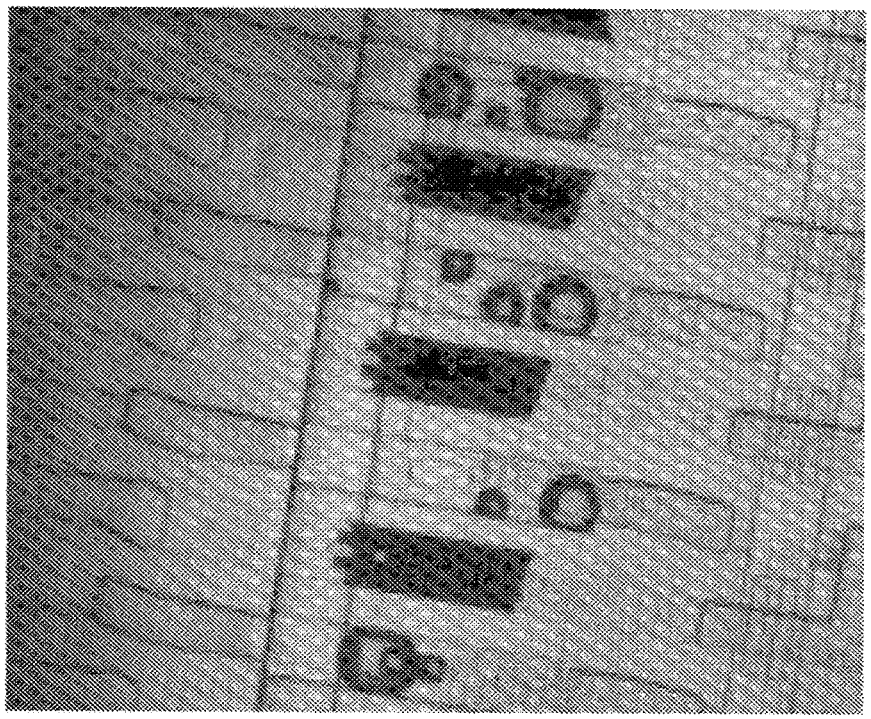
FIGS. 16B and 16C depict the performance of three pairs of sequential sieve valves valve in accordance with an embodiment of the disclosure.
Figure 16B:
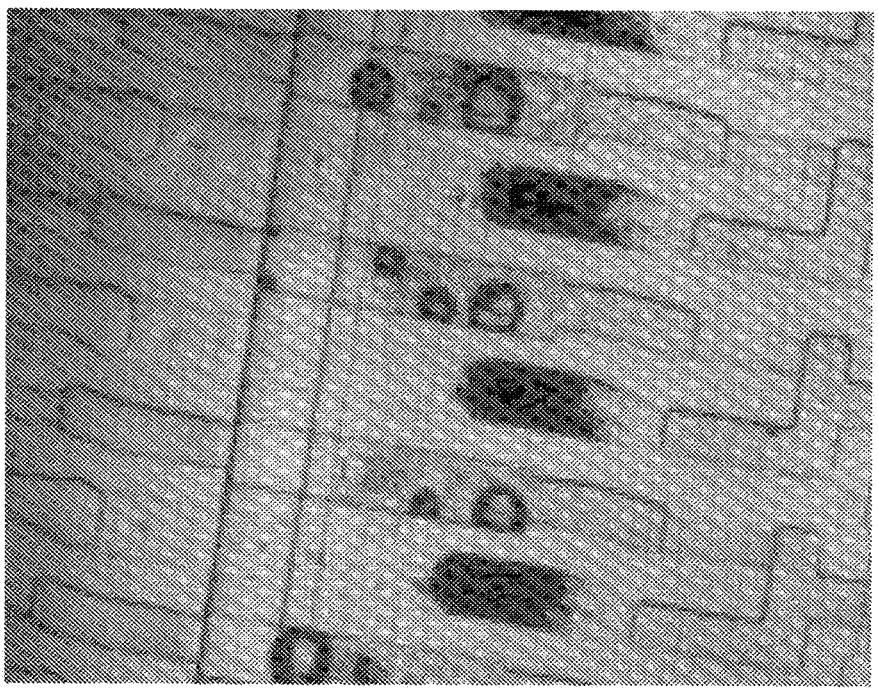

The performance of three pairs of sequential sieve valves having the channel geometry depicted in FIG. 16A is illustrated in FIGS. 16B and 16C. In FIG. 16B, the first sieve valves in each pair are actuated to retain a plurality of beads as fluid flows through the respective channels. The accumulation of beads can be clearly seen with a clear concentrated packing of beads adjacent to the valve and additional beads accumulating at the tail of each channel. In FIG. 16C, the first sieve valves are opened and the second sieve valves are closed. Well-defined linear sealing profiles are seen that reflect the channel profile in FIG. 16A.

Figure 16F:
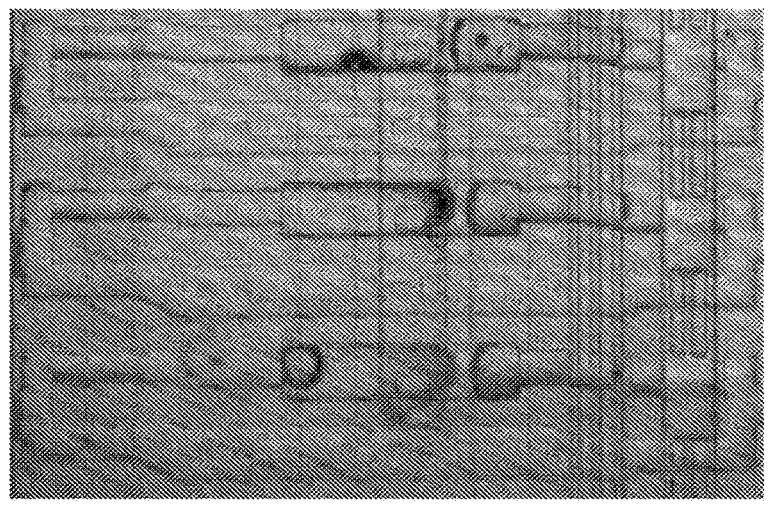
FIGS. 16D-16F depict the washability of the toothed sieve valve in accordance with an embodiment of the disclosure.
Figure 16E:
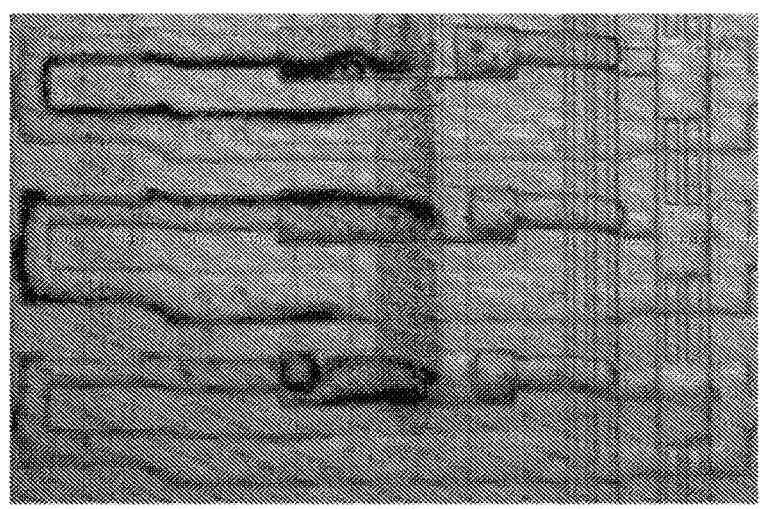
Figure 16D:
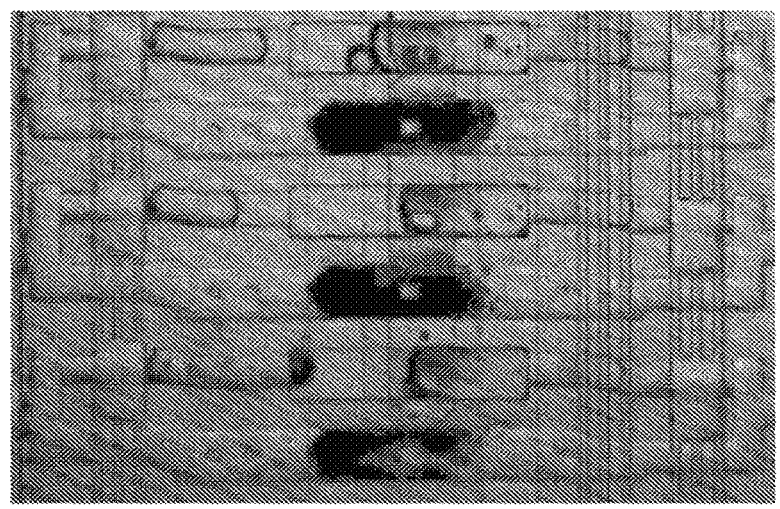

Referring now to FIGS. 16D-16F, the washability of the toothed sieve valve is illustrated. In FIG. 16D, the sieve valves are actuated to retain a plurality of beads in each flow channel. In FIG. 16E, the sieve valve is actuated to release the retained beads. The beads can be seen flowing past the sieve valve. In FIG. 16F, the beads are largely removed from the sieve valve.

Figure 17A:
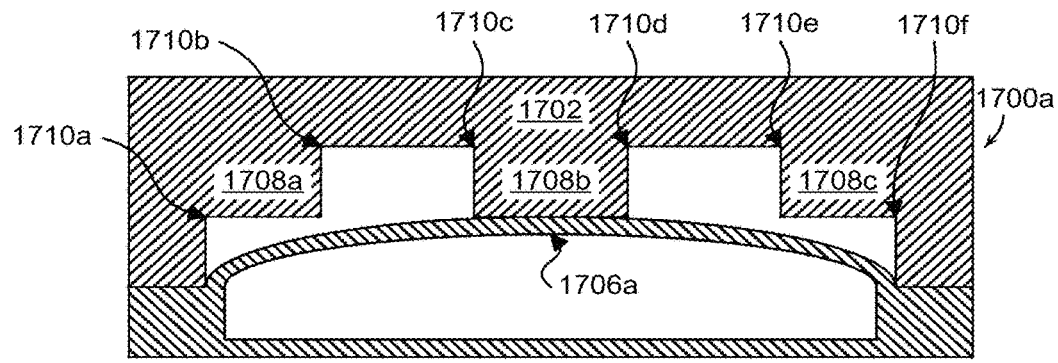
FIGS. 17A and 17B depict various configurations of sieve valves in accordance with an embodiment of the disclosure.
Figure 17B:
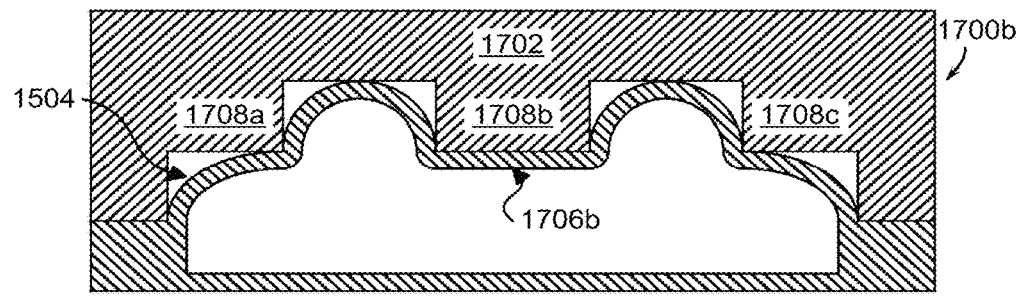

Referring now to FIGS. 17A and 17B, various configurations of sieve valves 1700a, 1700b are depicted with identical substrates 1702, channels 1704, protrusions 1708, and corners 1710. Depending on the pressure applied to flexible membrane 1706, the membrane's thickness and/or elasticity, and the dimensions of substrate channel 1704, protrusions 1708, and corners 1710, flexible membrane 1706 may deform with a substantially circular, oval, or ellipsoidal cross-section as depicted in FIG. 17A. In other embodiments, protrusions 1708 may contact and affect the cross-sectional shape of flexible membrane 1706 as depicted in FIG. 17B.

Figure 18:
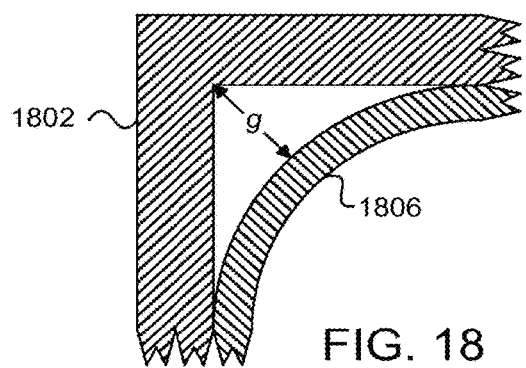
FIG. 18 depicts a gap dimension g between a membrane and a channel wall in accordance with an embodiment of the disclosure.

Referring now to FIG. 18, the sieve valves provided herein are adapted and configured for actuation to partially occlude a flow channel in order to retain certain materials while allowing other materials such as fluids to flow through the sieve valve. This is achieved by gaps between the deployed flexible membrane 1806 and the walls of the substrate 1802. In general, the widest gaps (and therefore, the greatest opportunity for flow) will occur at the corners of the channel. For example, a gap of less than 1 µm can be preferred in some embodiments in order to retain DYNABEADS® substrate having a diameter of 1.0 µm. Smaller sieve valves can also retain larger beads or sieve valves can be built to a lower tolerance. For example, sieve valves can be built to retain substrates having diameters of about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, and the like.

Figure 19:
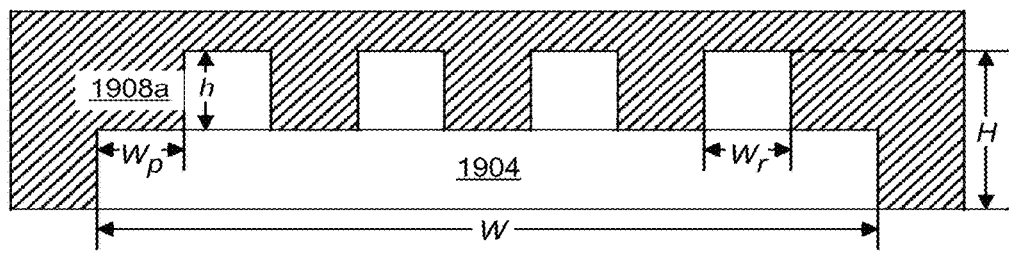
FIG. 19 depicts channel and protrusion cross-sections in accordance with an embodiment of the disclosure.

Referring now to FIG. 19A, the channel 1904a can have a generally rectangular cross-sectional profile. For example, the channel 1904a can have a defined width W and a defined height H. In some embodiments, width W can be between about 1 µm and about 5 µm, between about 5 µm and about 25 µm, between about 25 µm and about 50 µm, between about 50 µm and about 100 µm, between about 100 µm and about 125 µm, between about 125 µm and about 150 µm, between about 150 µm and about 175 µm, between about 175 µm and about 200 µm, between about 200 µm and about 225 µm, between about 225 µm and about 250 µm, between about 250 µm and about 275 µm, and between about 275 µm and about 300 µm. In some embodiments, height H can be between about 5 µm and about 10 µm, between about 10 µm and about 15 µm, between about 15 µm and about 20 µm, between about 20 µm and about 25 µm, between about 25 µm and about 30 µm, between about 30 µm and about 35 µm, between about 35 µm and about 40 µm, between about 40 µm and about 45 µm, between about 45 µm and about 50 µm, and between about 50 µm and about 55 µm.

Referring now to FIG. 19B, channel 1904b can also be described as a cross-section from which additional recesses extend.

Different flow channels in a particular microfluidic device can have different dimensions, depending on the function of the particular channel. In some embodiments of the invention the flow channel has a low aspect ratio (e.g., a height to width ratio of less than about 1:2, less than about 1:5, less than about 1:10, or less than about 1:15).

Protrusions 1908 and/or recesses 1912 can also have a number of cross-sections, such as a rectangle, a square, a triangle, a semi-circle, a semi-oval, a semi-ellipse, a triangle, an n-gon, and the like. Protrusions 1908 and/or recesses 1912 can have a defined width $w_p$, $w_h$ and a defined height h. These widths and heights can be uniform across protrusions or can vary among protrusions 1908 and/or recesses 1912 (e.g., to achieve a desired gap dimension g from a deployed flexible membrane). For example, the widths $w_p$, $w_h$ can be between about 0.1 µm and about 1 µm, between about 1 µm and about 5 µm, between about 5 µm and about 10 µm, between about 10 µm and about 15 µm, between about 15 µm and about 20 µm, and between about 20 µm and about 25 µm. The height h can be between about 0.1 µm and about 0.5 µm, between about 0.5 µm and about 3 µm, between about 3 µm and about 5 µm, between about 5 µm and about 10 µm, between about 10 µm and about 15 µm, between about 15 µm and about 20 µm, and between about 20 µm and about 25 µm.

The dimensions of protrusions 1908 can be sized to trap a capture substrate having a specified dimension. Generally speaking, protrusions 1908 and inter-protrusion spacing should be smaller than the capture substrate diameter (or minimum dimension). Preferably, protrusions and inter-protrusion spacing will be 20% less than the capture substrate diameter (or minimum dimension). For example, protrusion and inter-protrusion spacing dimensions of 3 μm may be preferred in order to retain beads having a diameter of 5 μm.

Although the channel 1904 and protrusions 1908 are depicted as having well-defined, square walls and corners, such edges may have a rounded, chamfered, eased, or smoothed geometry (e.g., due to fabrication through photolithography). In such situations, the measurements and ratios described herein can be measured from the widest point in the channel or protrusion cross-section.

Figure 20:
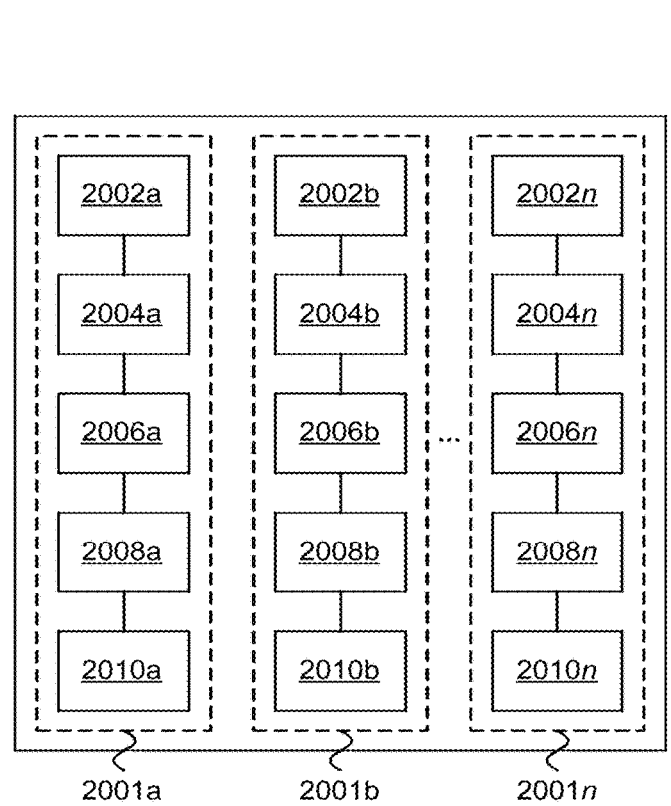
FIG. 20 depicts a microfluidic device in accordance with an embodiment of the disclosure.

Referring now to FIG. 20, a microfluidic device 2000 is provided including one or more plurality of microfluidic circuits 2001a-n. The microfluidic circuits 2001 can each include one or more input valves 2002, holding chambers 2004, sieve valves 2006, mixing circuits 2008, and output valves 2010. For example, the microfluidic device 2000 can include a plurality of microfluidic circuits such as 2, 4, 6, 8, 10, 12, 16, 18, 20, 24, 28, 32, 48, 64, 96, 128, 132, 256, 264, 512, 528, and the like.

In some embodiments, a single valve can be used for both input and output. The use of separate input and output valves advantageously facilitates loading, by permitting gases to escape when fluid is introduced.

Microfluidic circuits 2001 can lie in separate laminar layers of the microfluidic device. Additionally or alternatively, microfluidic circuits 2001 can span across a plurality of laminar layers of the microfluidic device.

Figure 21:
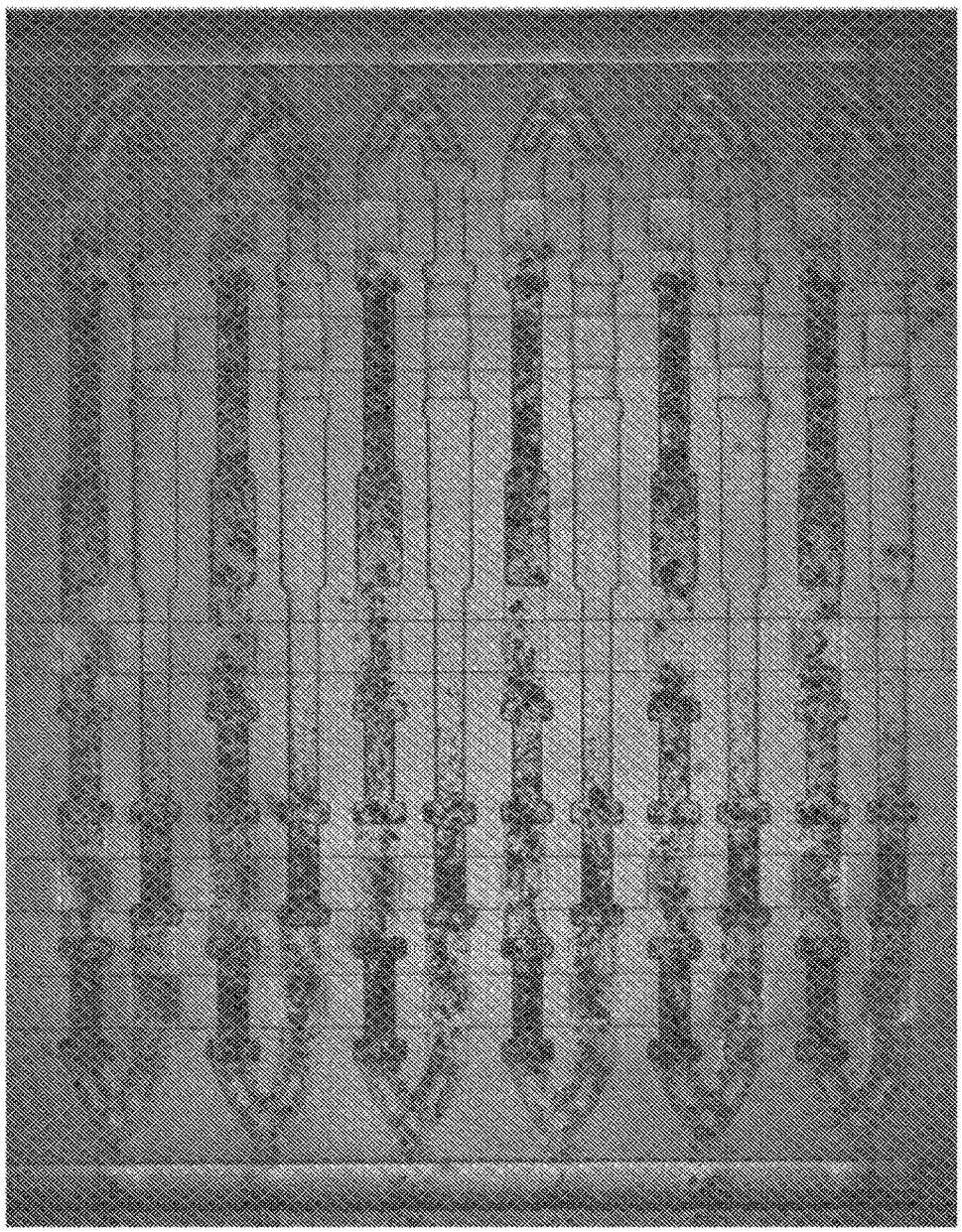
FIG. 21 depicts a microfluidic chip 2100 including a plurality of mixing circuits in accordance with an embodiment of the disclosure.

FIG. 21 depicts a microfluidic chip 2100 including a plurality of mixing circuits. As discussed previously in the context of FIG. 1, the mixing circuits can include one or more sieve valves.

Figure 22A:
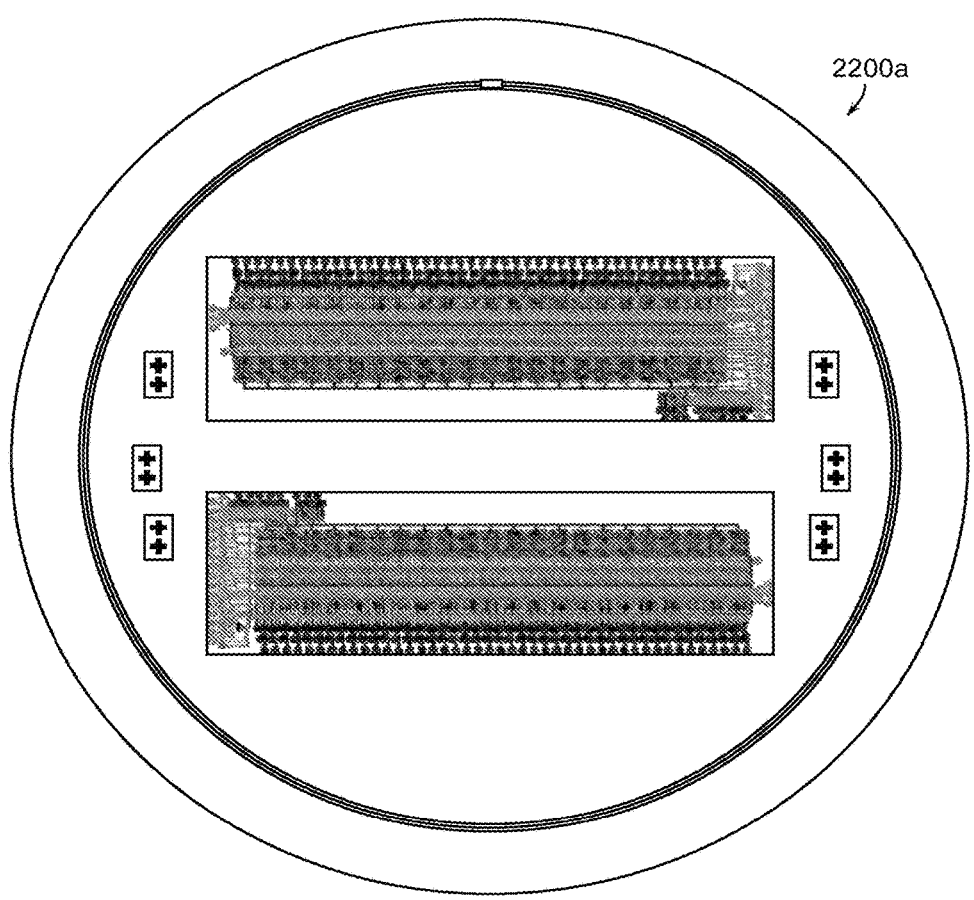
FIGS. 22A and 22B provide schematics of exemplary microfluidic devices in accordance with an embodiment of the disclosure.
Figure 22B:
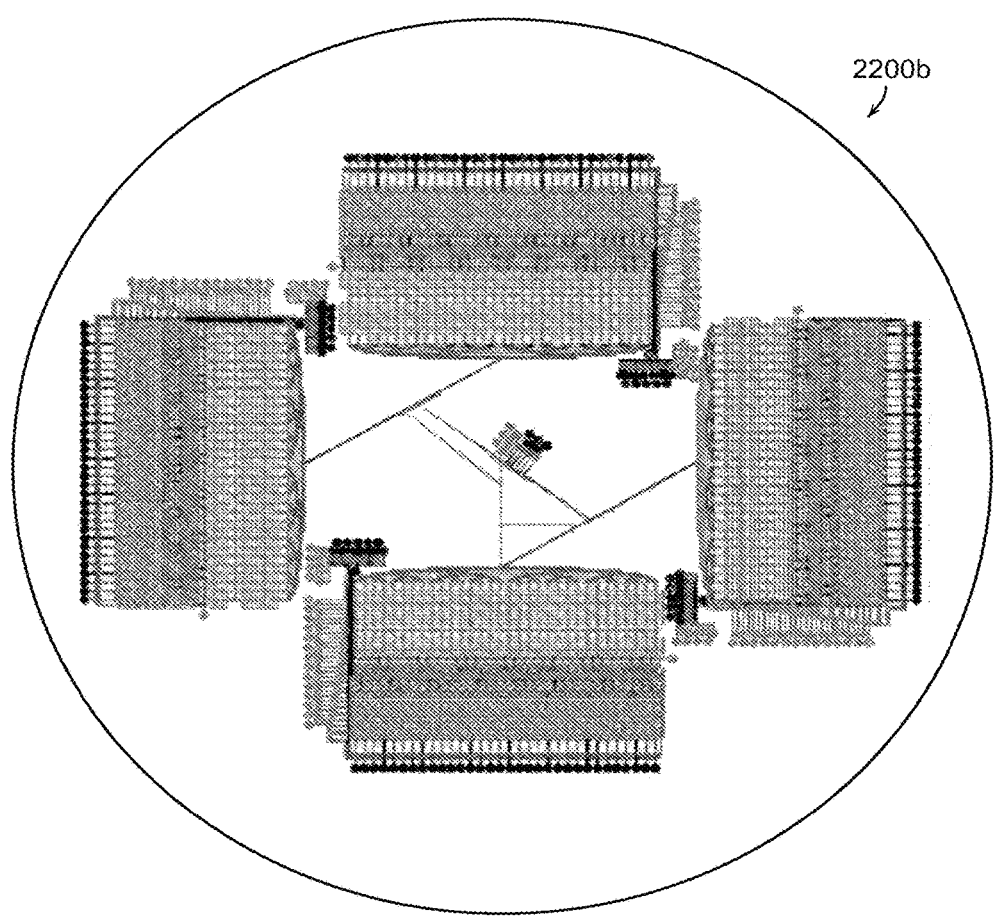

Referring now to FIGS. 22A and 22B, schematics of exemplary microfluidic devices 2200a and 2200b are provided. By utilizing the toothed sieve valves described herein, the size of individual microfluidic circuits can be shrunk relative to a microfluidic circuits having non-toothed sieve valves on microfluidic device 2200b. As a result, more microfluidic circuits were placed within a 4 inch diameter microfluidic device 2200a than an equal size microfluidic device 2200b as discussed below:

|  | Microfluidic Device 2100a with Toothed Sieve Valves | Microfluidic Device 2100b with Non-Toothed Sieve Valves |
|---|---|---|
| Number of Microfluidic Circuits | 2 × 132 = 264 | 4 × 32 = 128 |
| Grown Chamber Volumes | 25 nL | 500 nL |
| Number of Cells Required | 20K | 500K |
| Mixing Circuit Size | 40 nL | 200 nL |

Figure 23:
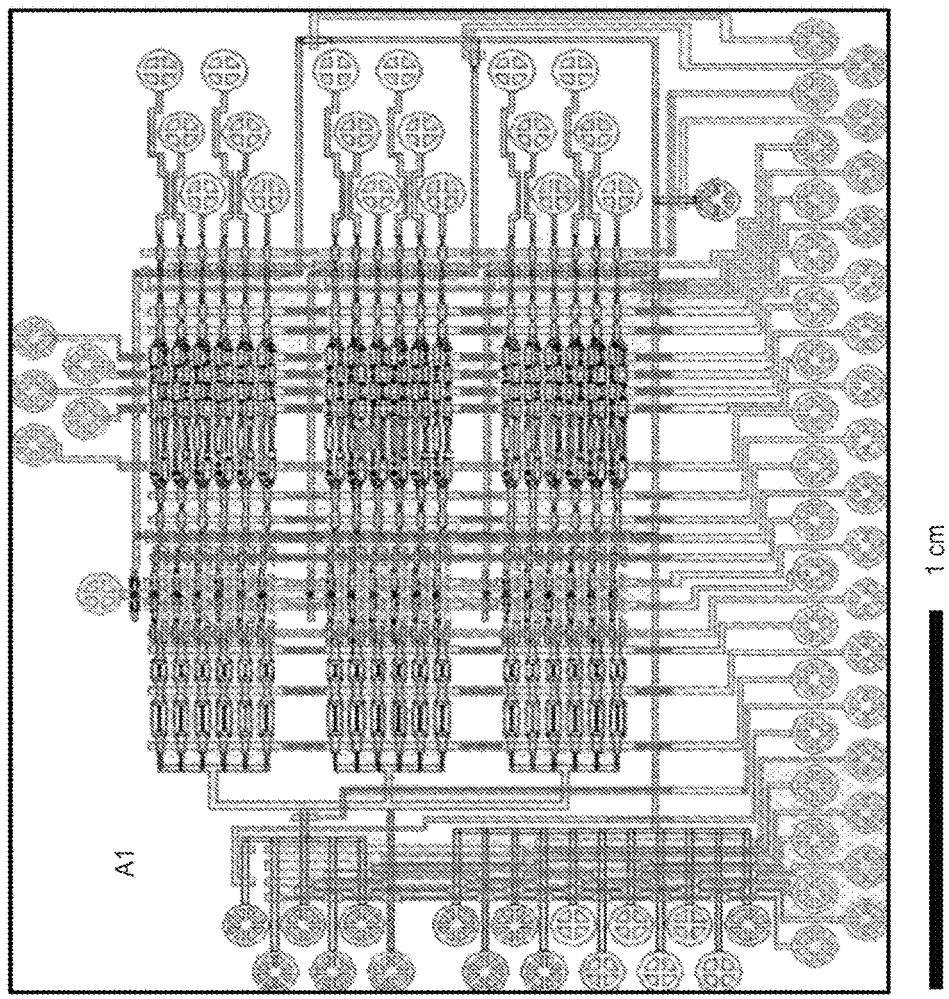
FIG. 23 provides a schematic of a microfluidic device in accordance with an embodiment of the disclosure.

Referring now to FIG. 23, a schematic of a microfluidic device is depicted. The red components represent control layer structures. The other colors (i.e., teal, orange, blue, grey, and green) represent heights of 15 μm, 3 μm, 13 μm, 30 μm, and 50 μm, respectively.

Figure 24:
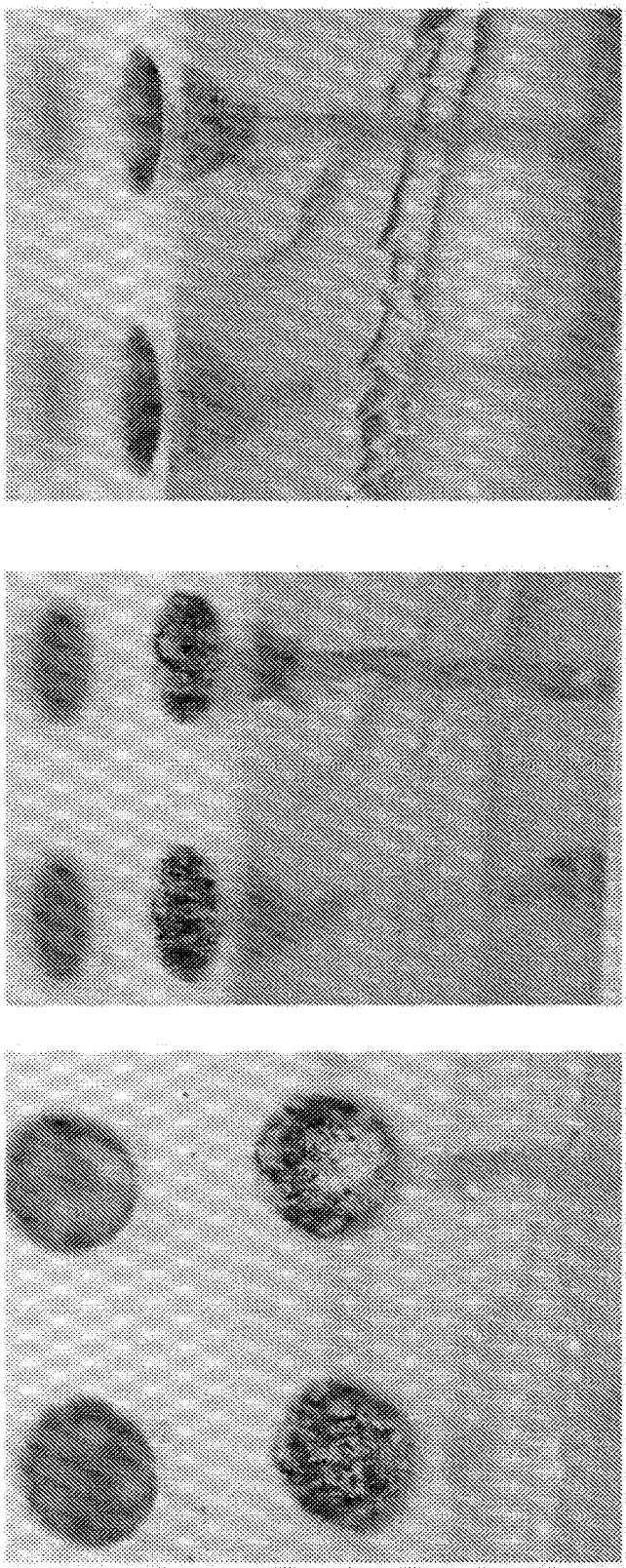
FIG. 24 depicts a microfluidic device including one or more ports adapted and configured to receive or permit retrieval of fluids from the microfluidic device in accordance with an embodiment of the disclosure.

Referring now to FIG. 24, microfluidic device can include one or more ports adapted and configured to receive or permit retrieval of fluids from the microfluidic device. Such ports can, for example, have a reducing diameter such as a cone in order to interface with channels on the microfluidic device. Such ports preferably have a diameter or cross-sectional dimension sufficient to receive a pipette, micropipette, pin, or other fluid transfer device. For example, ports can have a diameter or cross-sectional dimension of between about 0.5 mm and about 1 mm, between about 1 mm and about 5 mm, and the like. Such ports can be formed with a laser using the method described in J. Huft et al., "Three-dimensional large-scale microfluidic integration by laser ablation of interlayer connections," 10 Lab Chip 2358-65 (2010).

Ports can have a spacing corresponding to standard well plates or other laboratory equipment. For example, ports having centers spaced at 2.25 mm will permit simultaneous loading from a 384 well plate (which has centers spaced 4.5 mm apart).

Figure 25:
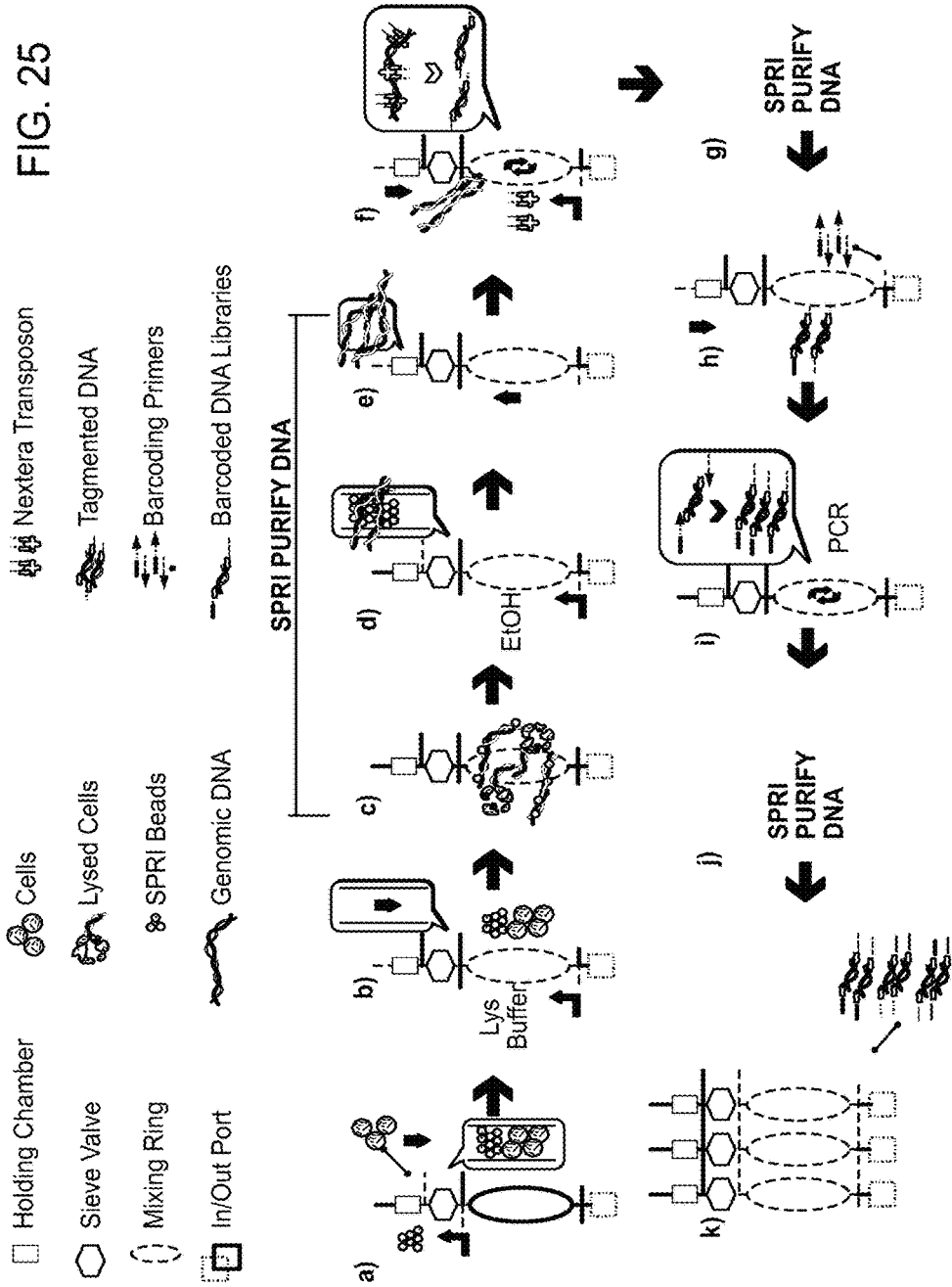
FIG. 25 depicts a protocol for the preparation of a genomic library using the microfluidic device in accordance with an embodiment of the disclosure.

Referring now to FIG. 25, the microfluidic devices described herein can be used to isolate an analyte from a sample and the analyte processed using the microfluidic device, for example, to produce a library of genomic DNA fragments. In one embodiment, a sample comprising cells is loaded into the microfluidic device with beads for Solid-phase reversible immobilization (SPRI). Cell lysis buffer is added to lyse the cells, releasing genomic DNA. The genomic DNA is captured on the SPRI beads and impurities are removed from other sample components (e.g., by washes). The DNA is then processed using transposon based fragmentation (NEXTERA®), which generates DNA fragments and fixes an amplification adaptor, comprising a barcode, to the DNA fragments. Primers hybridizing the amplification adaptors are added and the DNA fragments are amplified (e.g., by PCR) within the microfluidic device. The DNA fragments may then be used for additional purposes, including DNA sequencing.

Figure 26:
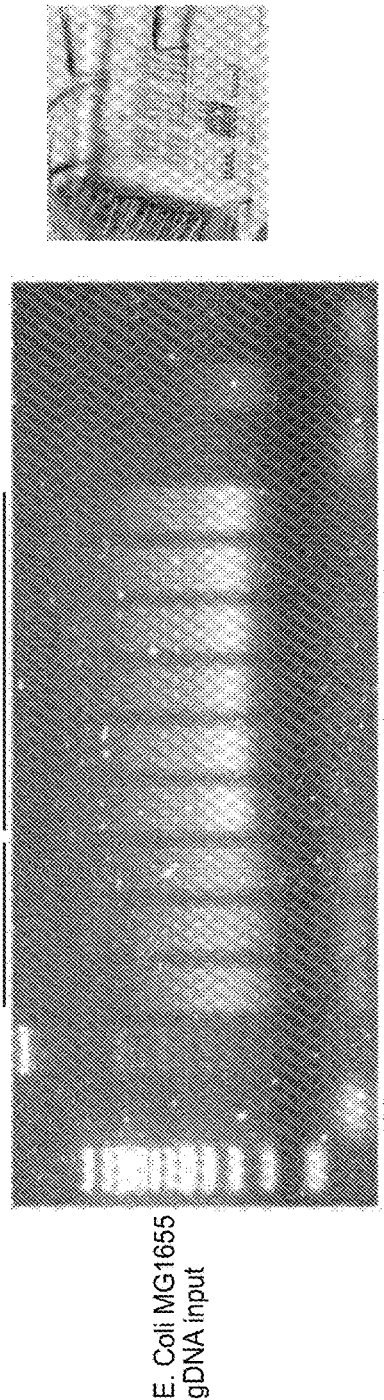
FIG. 26 is an image of an agarose gel with genomic DNA amplification products demonstrating the use of the microfluidic device in accordance with an embodiment of the disclosure for genomic DNA fragmentation and addition of an amplification adapter.

FIG. 26 is an image of an agarose gel with genomic DNA amplification products using the microfluidics device. The quality and amount of input DNA are shown (pg) that was loaded into the microfluidic device. DNA was fragmented and processed by NEXTERA® transposon-based reactions. The DNA fragments were amplified and run on the gel, showing the size distribution of fragments in each lane. This example demonstrates that use the microfluidic device can be used for genomic DNA fragmentation and amplification, which are useful for preparing libraries for DNA sequencing.

Figure 27:
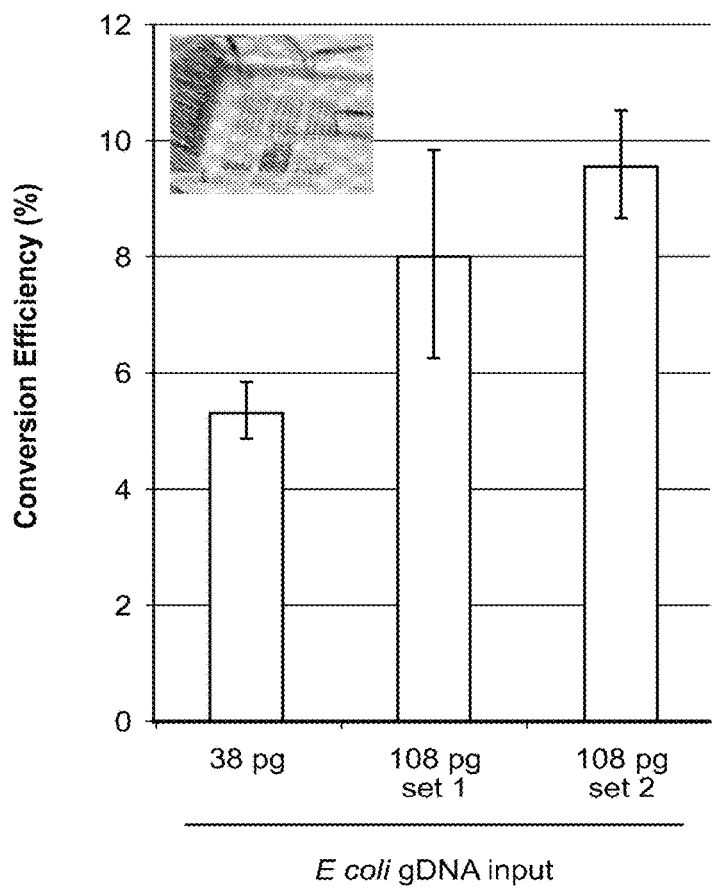
FIG. 27 is a chart showing that libraries produced using the microfluidic device in accordance with an embodiment of the disclosure have high conversion efficiency.

FIG. 27 shows that amplified DNA fragment quantity on the microfluidics device was greater than genomic input DNA quantity, indicating a conversion efficiency between 5-10%. This efficiency indicates that genomic DNA from 50-100 cells or as few as 10-20 cells may be used for high-quality genome sequencing. Additionally, low input capability on the microfluidic device allows reaction volumes to be minimized. It was found that no normalization was required for normalized input, as the coefficient of variation (CV) was determined to be about ~15%. Thus, the preparation showed good representation of DNA fragments from one preparation to the next. These results indicated that the microfluidic device could be used to generate DNA libraries for sequencing with high efficiency.

Figure 28:
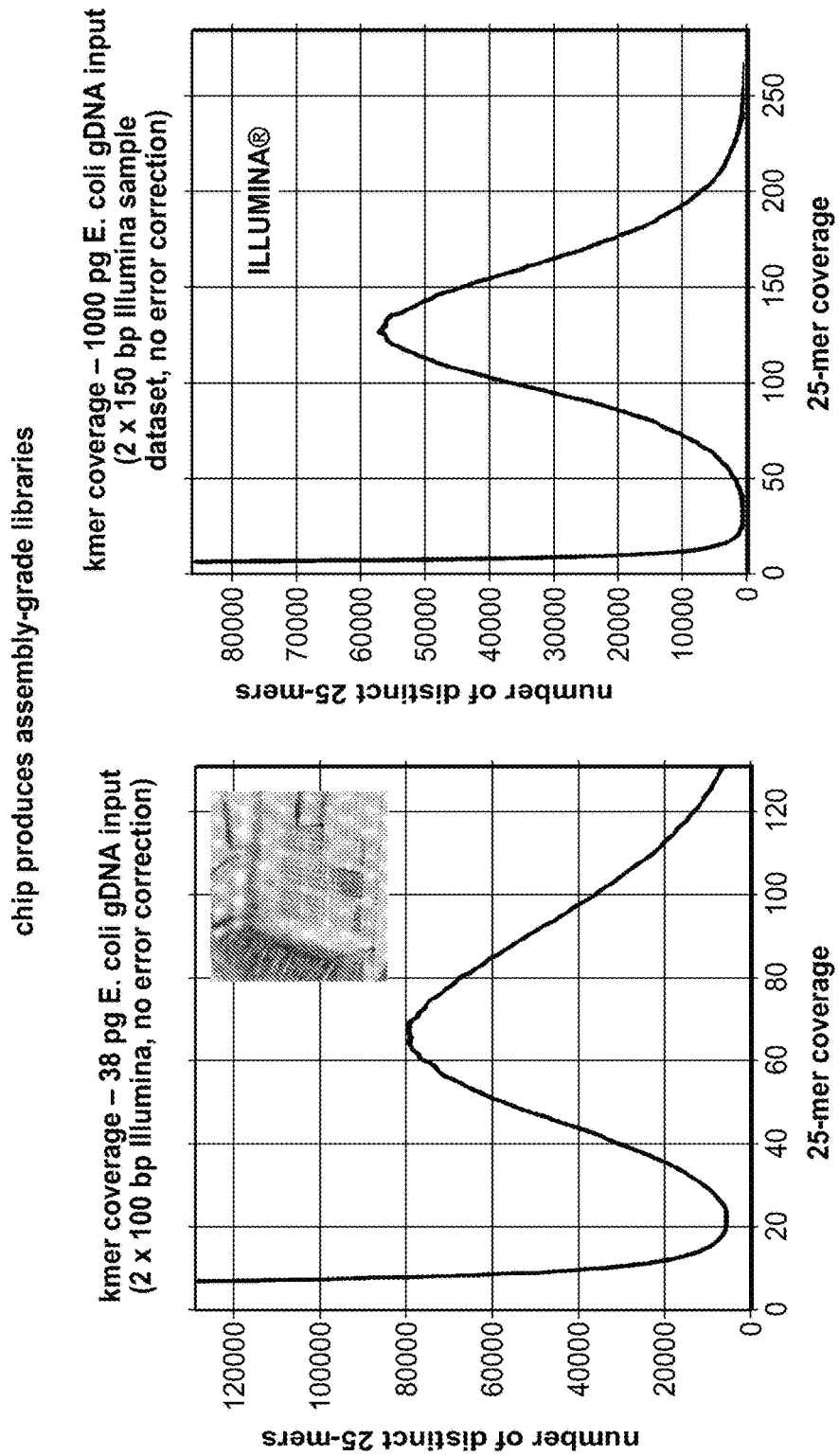
FIG. 28 are graphs showing that assembly-grade libraries were produced using the microfluidic device in accordance with an embodiment of the disclosure (left), compared to reference (right)

FIG. 28 shows that assembly-grade libraries were produced using the microfluidic device. DNA libraries made using the microfluidic device were sequenced. The number of distinct 25-mers was plotted against the coverage or number of times the distinct 25-mer was represented in the sequencing (left). As demonstrated by the plot, most of the 25-mers were read about 60-70 times during sequencing. Additionally, the number of errors was minimized, as indicated by separation of the main peak from the peak on the left. Sequencing errors are rare and account for the low measure of coverage under about 20. By comparison, a sequence reference from Illumina is shown in which a larger input of genomic DNA was used with longer reads (right).

This shows that genomic libraries made using the microfluidic device can yield sequence similar in quality to assembly-grade libraries.

FIG. 29 demonstrates sample barcoding of DNA using the microfluidic device. Amplification adaptors comprising a barcode were added to the ends of nucleic acid molecules in a reaction in the microfluidic device. As seen from the chart, template DNA was amplified, whereas template DNA lacking polymerase was not amplified.

Figure 30:
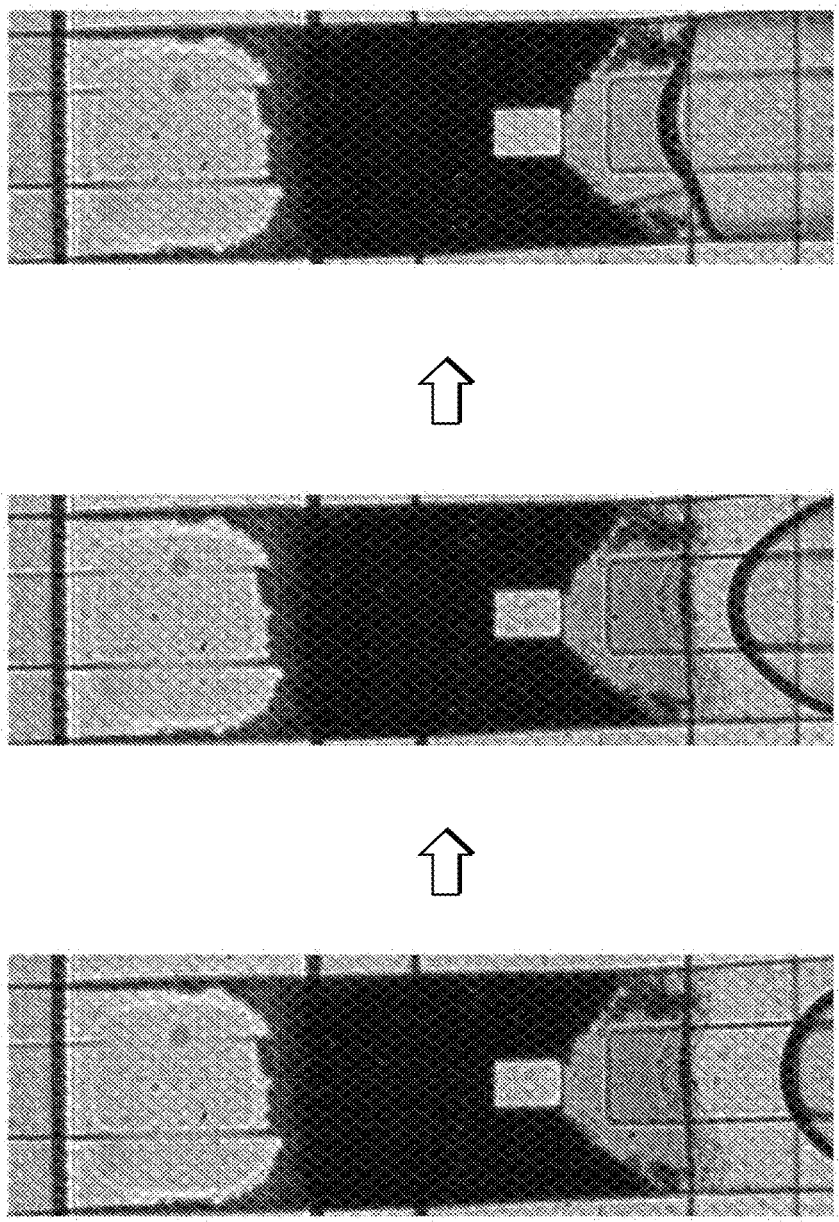
FIG. 30 depicts cell capture by filtering a bacterial solution through a sieve valve containing beads of the microfluidic device in accordance with an embodiment of the disclosure.

FIG. 30 depicts cell capture by filtering a bacterial solution through a sieve valve containing beads of the microfluidic device. A series of microscopic images are shown of a solution of E. coli bacteria cells passing through the sieve valve containing a mixture of 7 μm and 4.5 μm beads, forming a bead column. The beads created pores that were smaller than the diameter of the cells, so that the cells were filtered.

Figure 31:
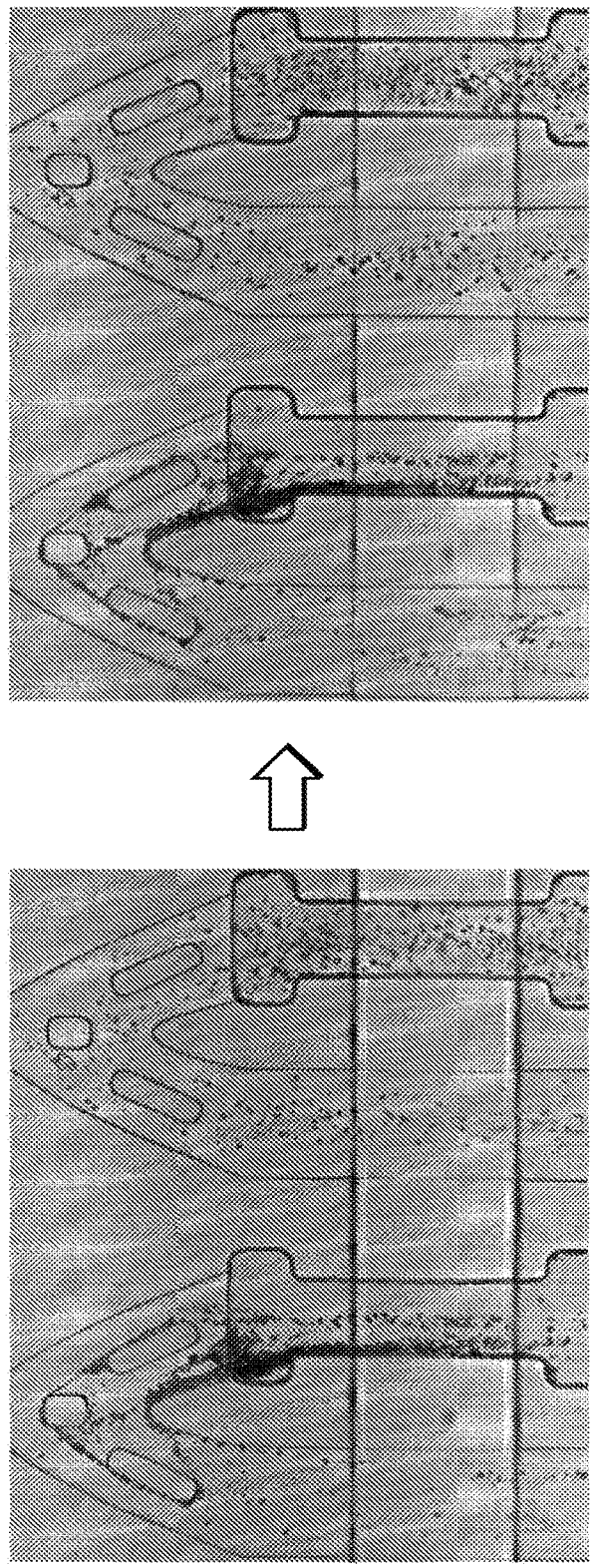
FIG. 31 depicts lysis of bacteria and capture of genomic DNA using the microfluidic device in accordance with an embodiment of the disclosure.

FIG. 31 depicts lysis of bacteria and capture of genomic DNA using the microfluidic device. A series of microscopic images are shown of the reactor containing 4.5 μm COOH beads, binding buffer that binds DNA to the beads, E. coli cells, and lysate buffer (QIAGEN® B1 buffer, 1% SDS, 1 mg/ml Proteinase K, 3 KU/ml mutanolysin, and 2 mg/ml lysozyme). Prior to the addition of binding buffer and mixing, the cell and the lysis buffer were heated to 37° C. for the enzyme to lyse the cells. The reactor on the left contains cells, while the reactor on the right does not. The filament-like feature in the reactor on the left shows that the cells were lysed in the microfluidic device and the capture of DNA by the COOH coated beads.

Figure 32:
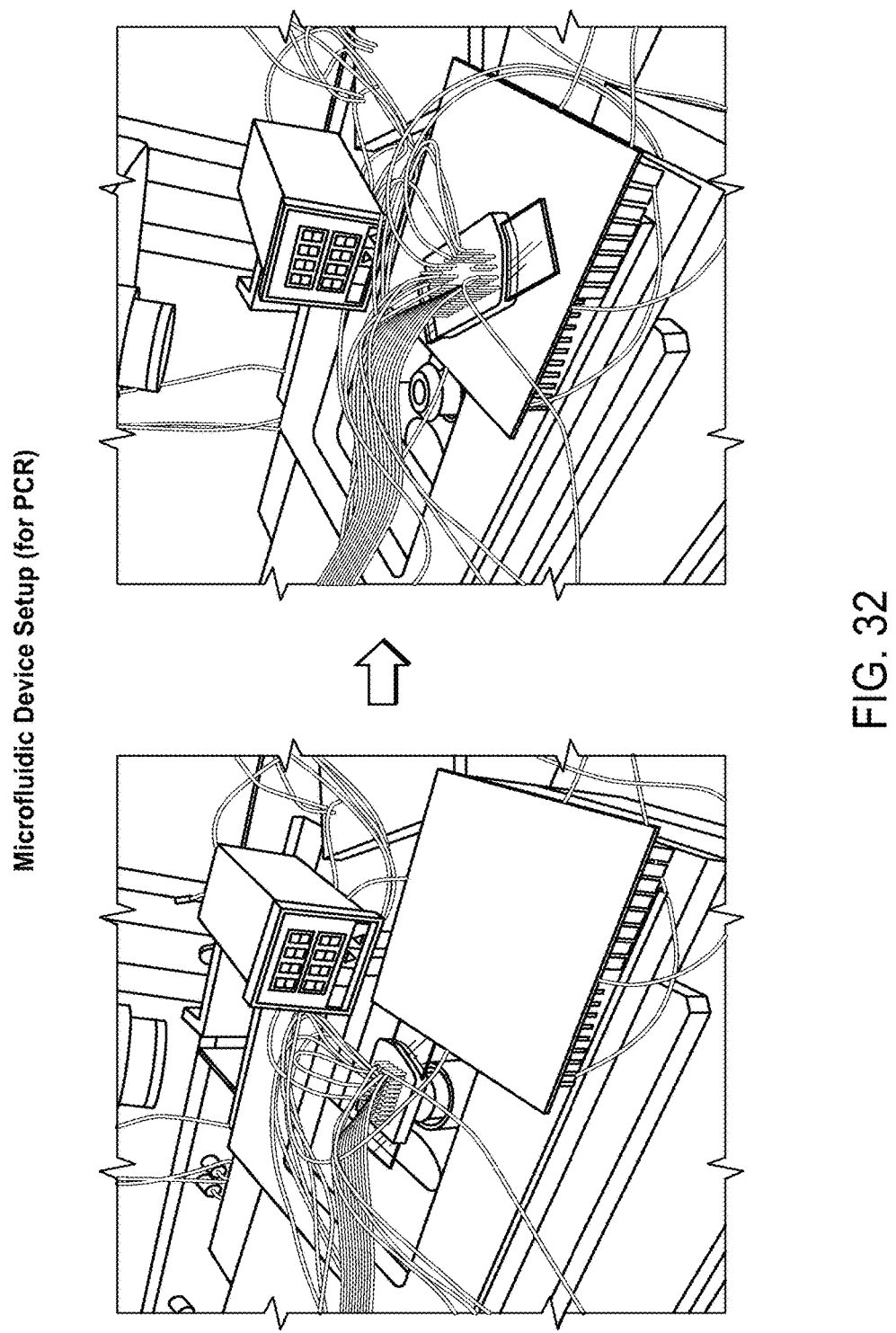
FIG. 32 depicts a setup for performing PCR using the microfluidic device in accordance with an embodiment of the disclosure.

FIG. 32 depicts a setup for performing PCR using the microfluidic device. The runs on the microfluidic chip prior to PCR were imaged on the microscope (left in pictures). To perform PCR, the chip was moved to a custom thermocycler platform that consists of Peltier heating elements and a heat sink underneath a copper plate that is connected to a PID, which is all controlled by the computer (right in pictures).

Figure 33:
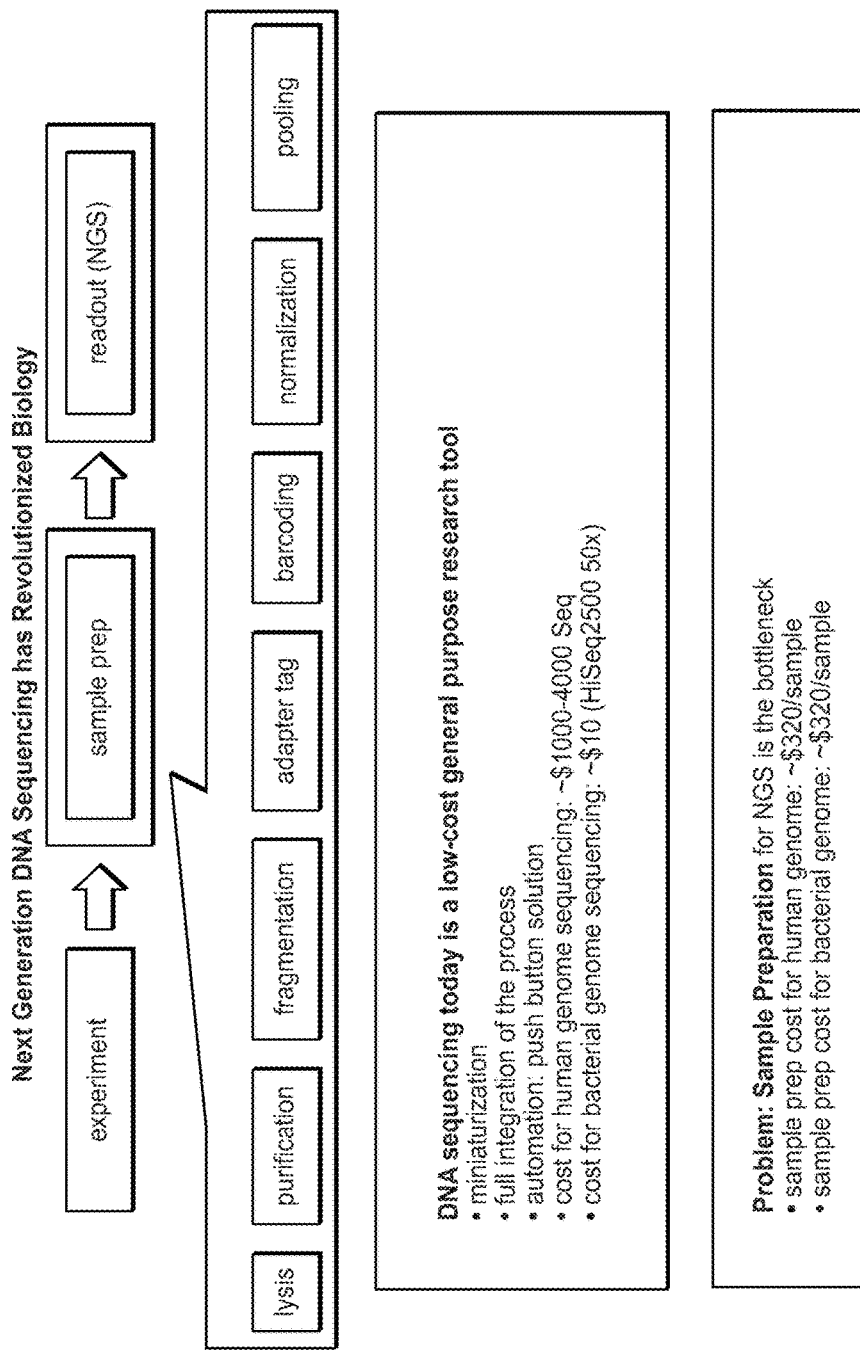
FIG. 33 is a schematic depicting the steps involved in sample preparation and next generation sequencing, and that sample preparation, which includes costly and time-consuming steps, is a bottleneck for next generation DNA sequencing.

FIG. 33 depicts that sample preparation is a bottleneck for next generation DNA sequencing. Next generation sequencing has made DNA sequencing cheap and broadly available for the study of biology. Two steps are involved in genome sequencing: 1) sample preparation and 2) DNA sequencing. Automating and integrating the intricate processes of the steps inside a sequencing machine or device has the potential to facilitate genome sequencing. At present, sequencing a human genome costs $1000-4000, not including the cost of DNA sample preparation, and sequencing a bacterial genome costs $10-50, not including the cost of DNA sample preparation. Sample preparation for genomic DNA sequencing involves multiple steps, including lysis, purification, fragmentation, adapter tagging, barcoding, normalization, and pooling, which are currently done by hand or expensive liquid handlers, thus contributing to the cost of sample preparation. The present invention addresses the problem of sample preparation, including for example, samples for genome-wide association studies (GWAS); clinical studies; single cells studies; multiparametric studies (e.g., microbiome as function of space, time, diet, host genetics, host disease, medical treatment); and/or increasing resolution in population genomics.

Figure 34:
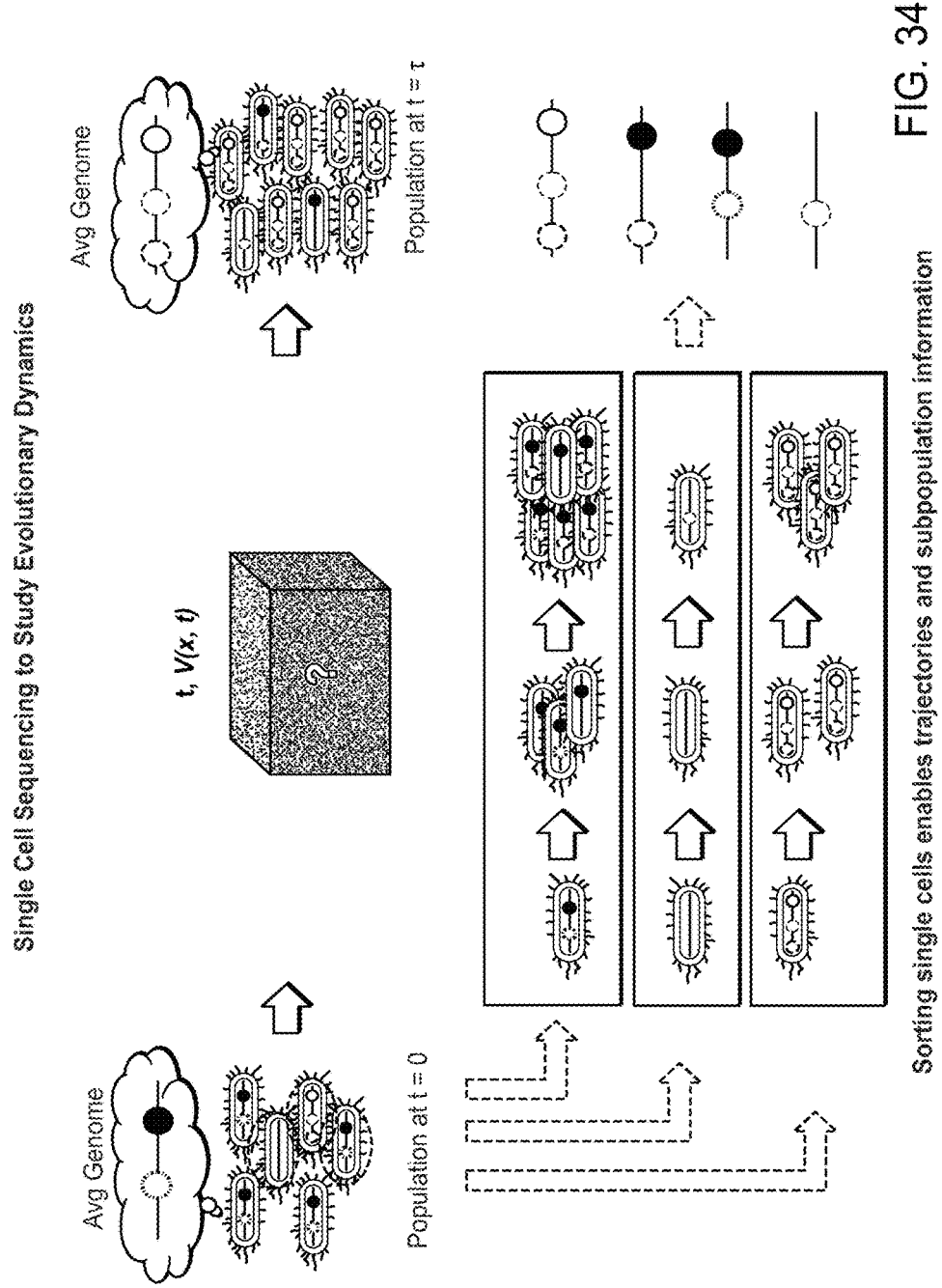
FIG. 34 depicts that single cell sequencing can be used to study evolutionary dynamics.

FIG. 34 depicts that single cell sequencing can be used to study evolutionary dynamics. The field of evolution has benefitted from next generation sequencing. Fundamental questions in microbial evolution can be addressed using DNA sequencing. Traditionally, changes in the genome are tracked in bulk. A population of bacteria is grown for a given time with perturbations, and the average genome of the population before and after the perturbation is compared. In bulk experiments, the events that happen during the perturbation are like a black box where the dynamics cannot be studied because they are averaged out. To study the dynamics of evolution, individual cells of a population are sorted and tracked to retrieve the trajectories and subpopulations that happen during the perturbation. DNA sequencing of individual cells has the potential to be a powerful tool in studying evolution, because genomes change every time a cell divides and these changes can be tracked by sequencing the genomes.

Figure 35:
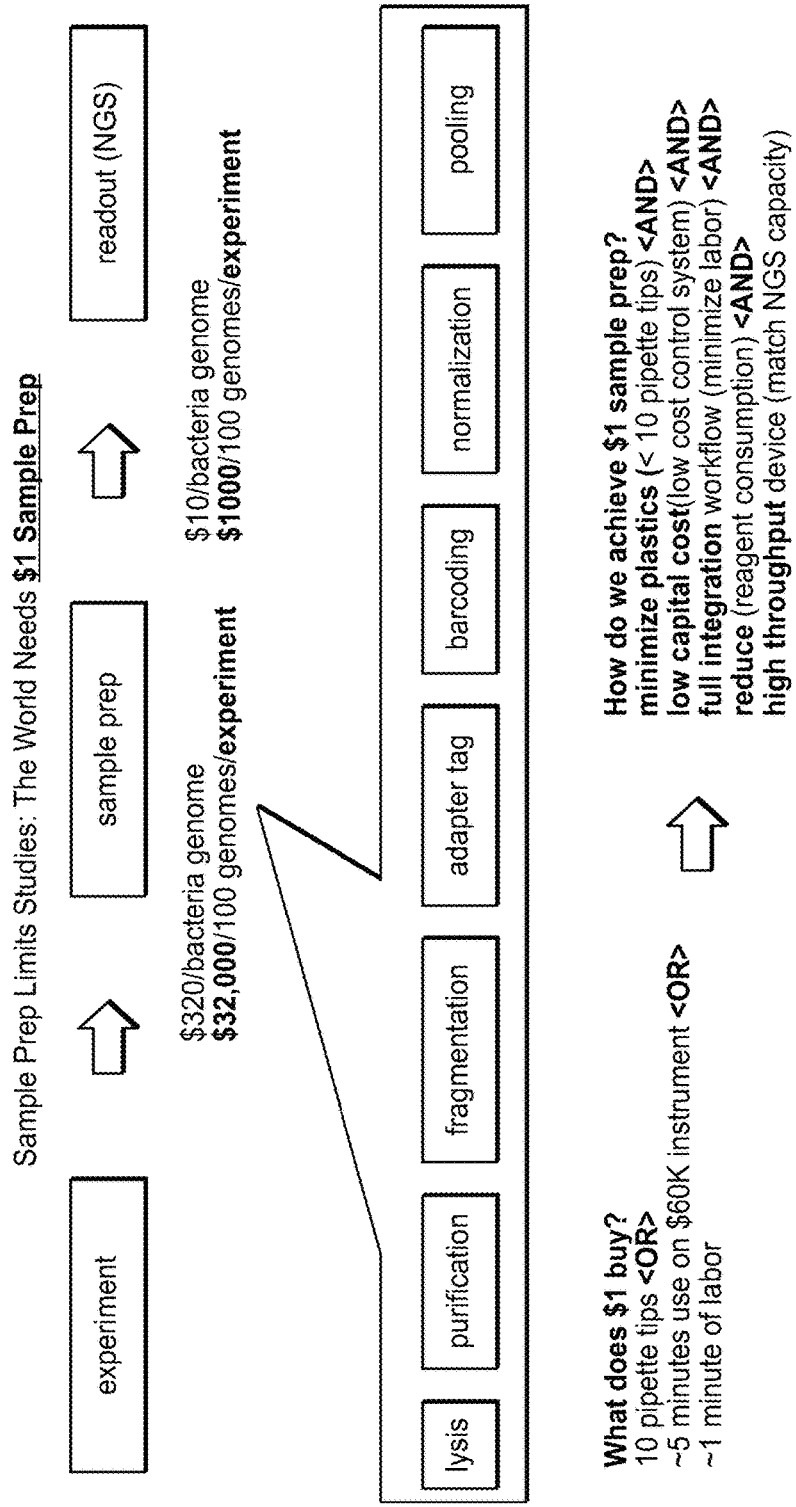
FIG. 35 depicts a proposal for reducing the cost of sample preparation.

FIG. 35 depicts a proposal for reducing the cost of sample preparation. Because the cost of sample preparation remains high, large scale experiments with a plurality of samples are expensive. Despite progress in reducing the cost of DNA sequencing, sample preparation costs dominate sequencing costs. To achieve low-cost sample preparation, one or more of the following strategies can be used: minimizing plastics (<10 pipette tips); low capital cost (low cost control system); full integration workflow (minimize labor); reduce (reagent consumption); and high throughput device (match NGS capacity).

Figure 36:
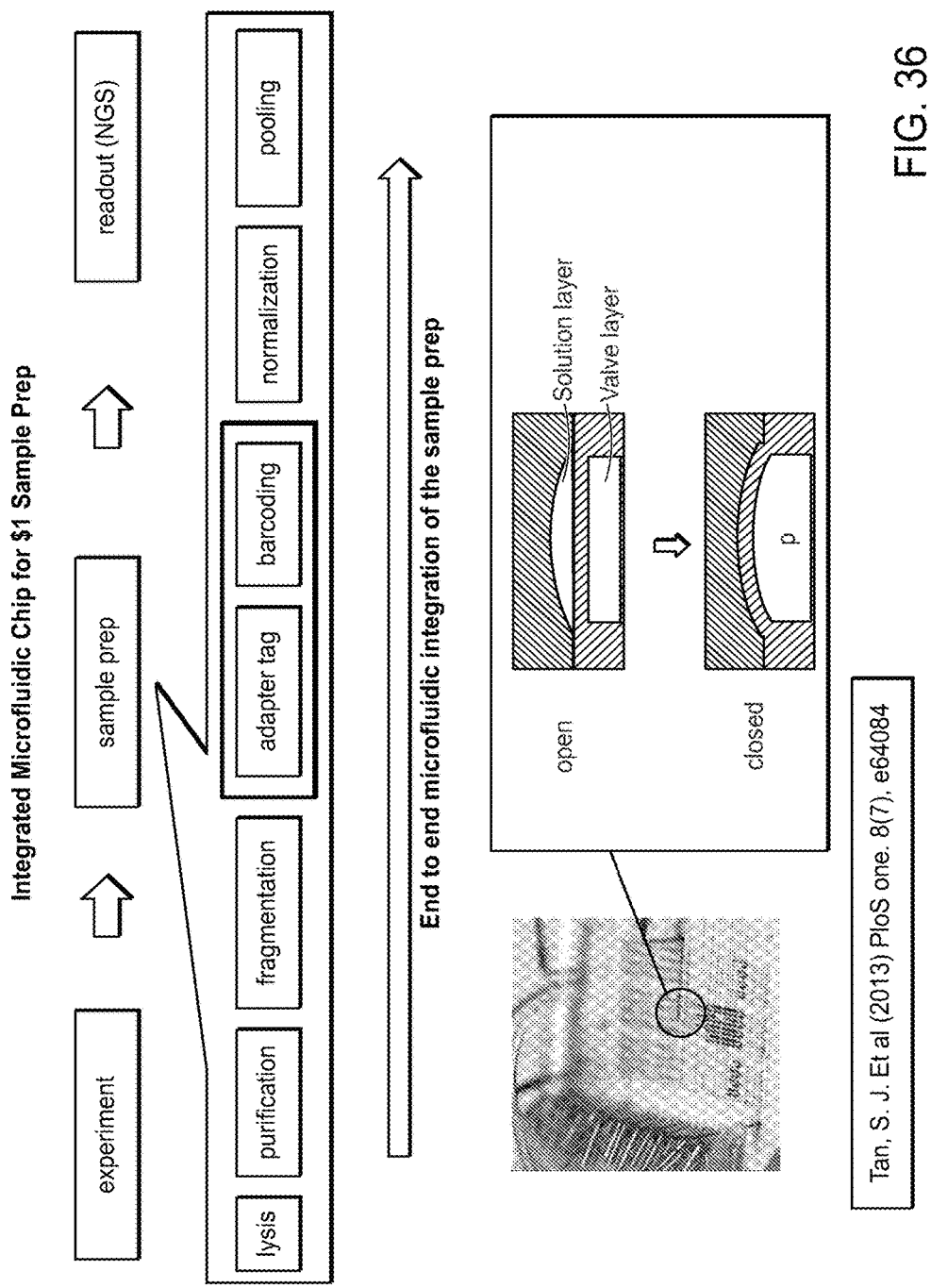
FIG. 36 depicts a fully integrated microfluidic chip that integrates the entire sample preparation process.

FIG. 36 depicts a fully integrated microfluidic chip that integrates the entire sample preparation process.

Figure 37:
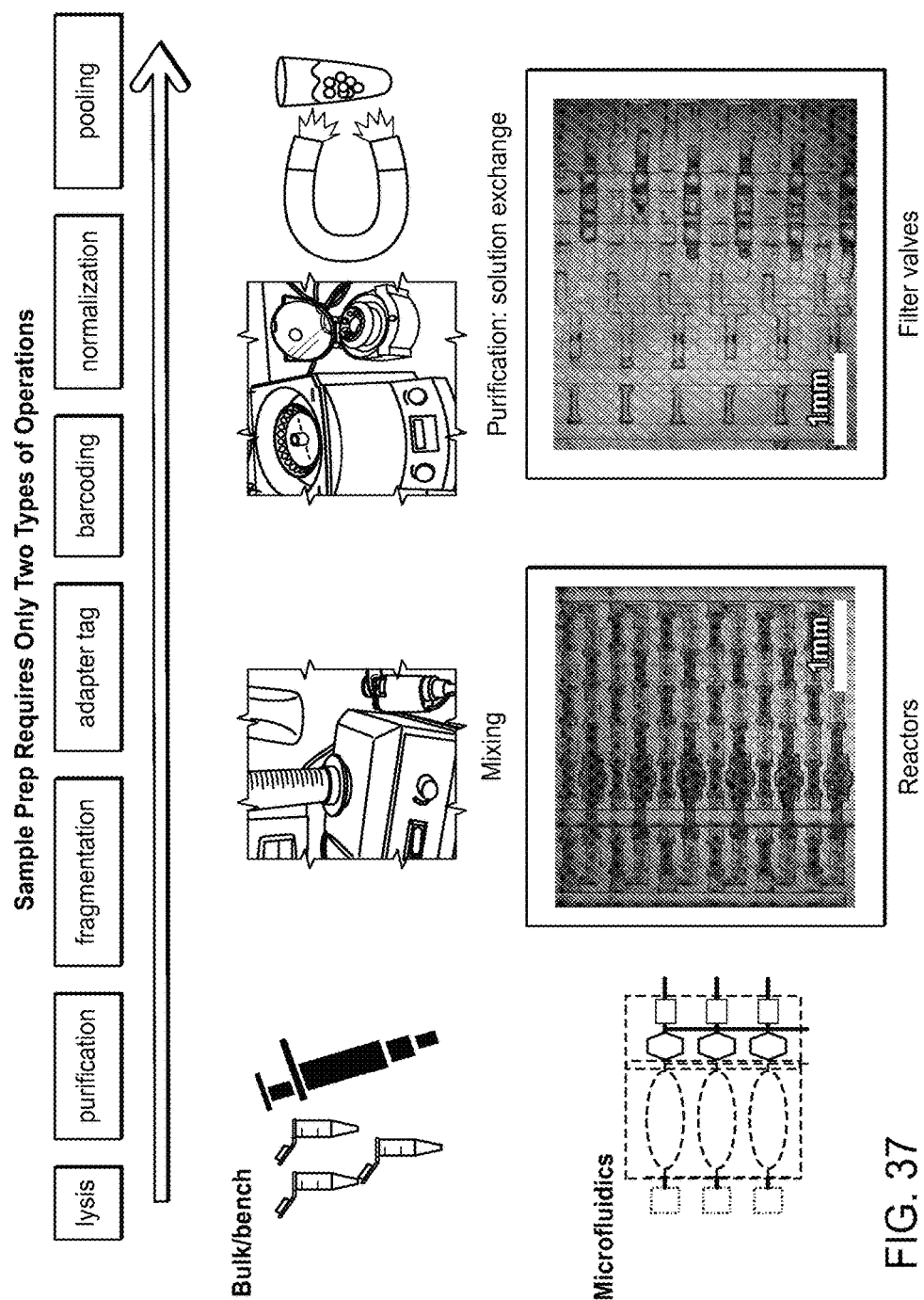
FIG. 37 depicts that sample preparation for genomic DNA can be reduced to two types of operations: mixing and purification/solution exchange.

FIG. 37 depicts that sample preparation involves minimally two types of operations. Despite all the steps in the sample preparation process, there are only two types of operations: (1) mixing and (2) purification by molecular selection and solution exchange. On the bench, mixing is performed, for example, by using a vortex or a pipette, and purification is performed, for example, using a centrifuges and magnet. In the microfluidic chip of the invention, mixing is performed by using a looped flow circuitry with peristaltic pumps ("reactors"), which mechanically move molecules around the loop for homogenization. Depicted are 6 individual reactors that contain beads with DNA, which are moved around the reactors. The purification is achieved by using beads that select cells or nucleic acids. Specially patterned filter valves are used that let solutions pass while holding the beads to wash and elute molecules bound to the beads. Depicted are 6 filter valves in purification operation which filter the beads moving right.

Figure 38:
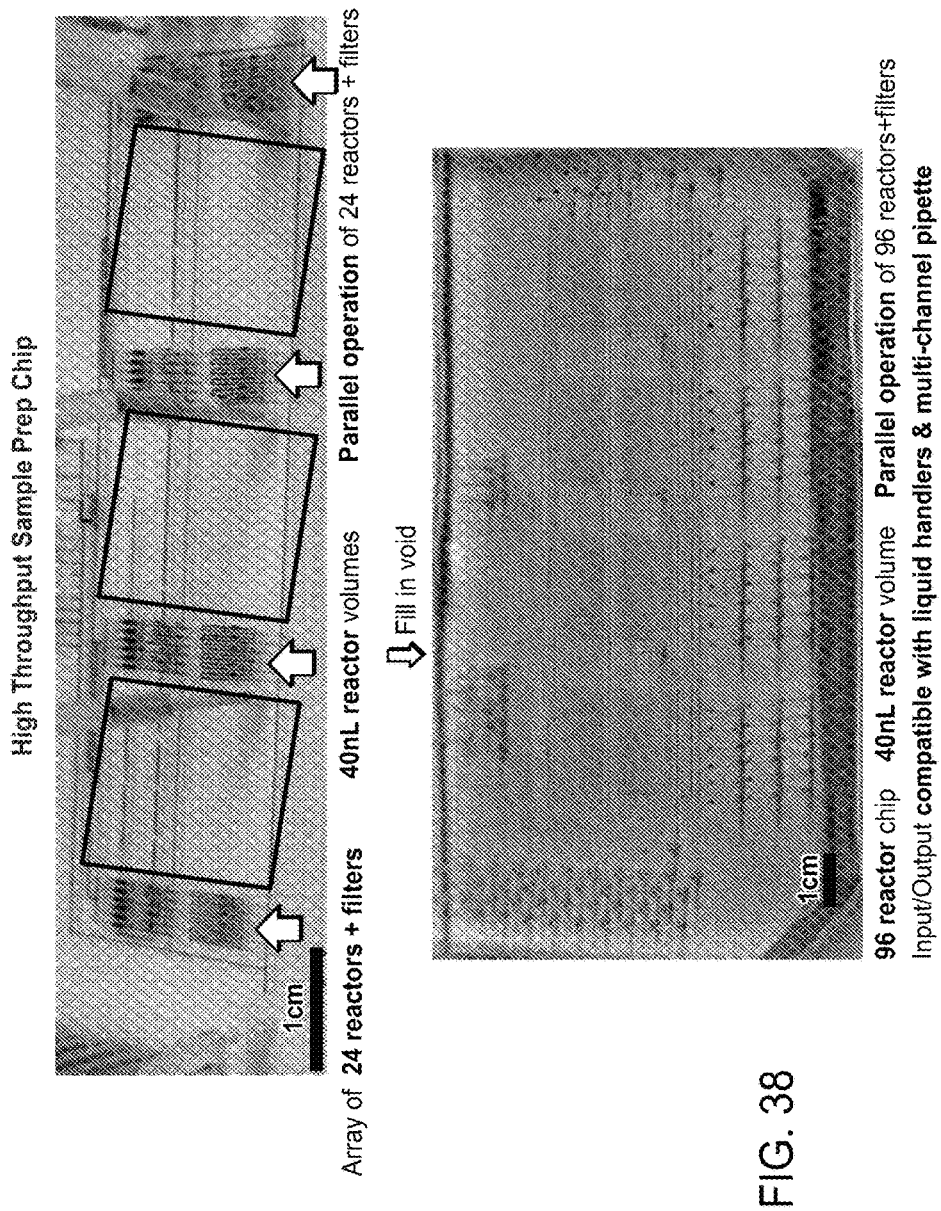
FIG. 38 depicts a high throughput sample preparation chip.

FIG. 38 depicts a high throughput sample preparation chip. A microfluidic chip for sample preparation was designed and fabricated. Depicted is a picture of a sample preparation chip with food coloring to show features. It has an array of 24 reactors with 40 nL volumes that operate in parallel. The chip is configured for transition into a 96 reactor chip, simply by adding more reactors in the empty spaces. It is also designed so that the spacing of the output ports is compatible with a 96 well plate and liquid handlers.

Figure 39:
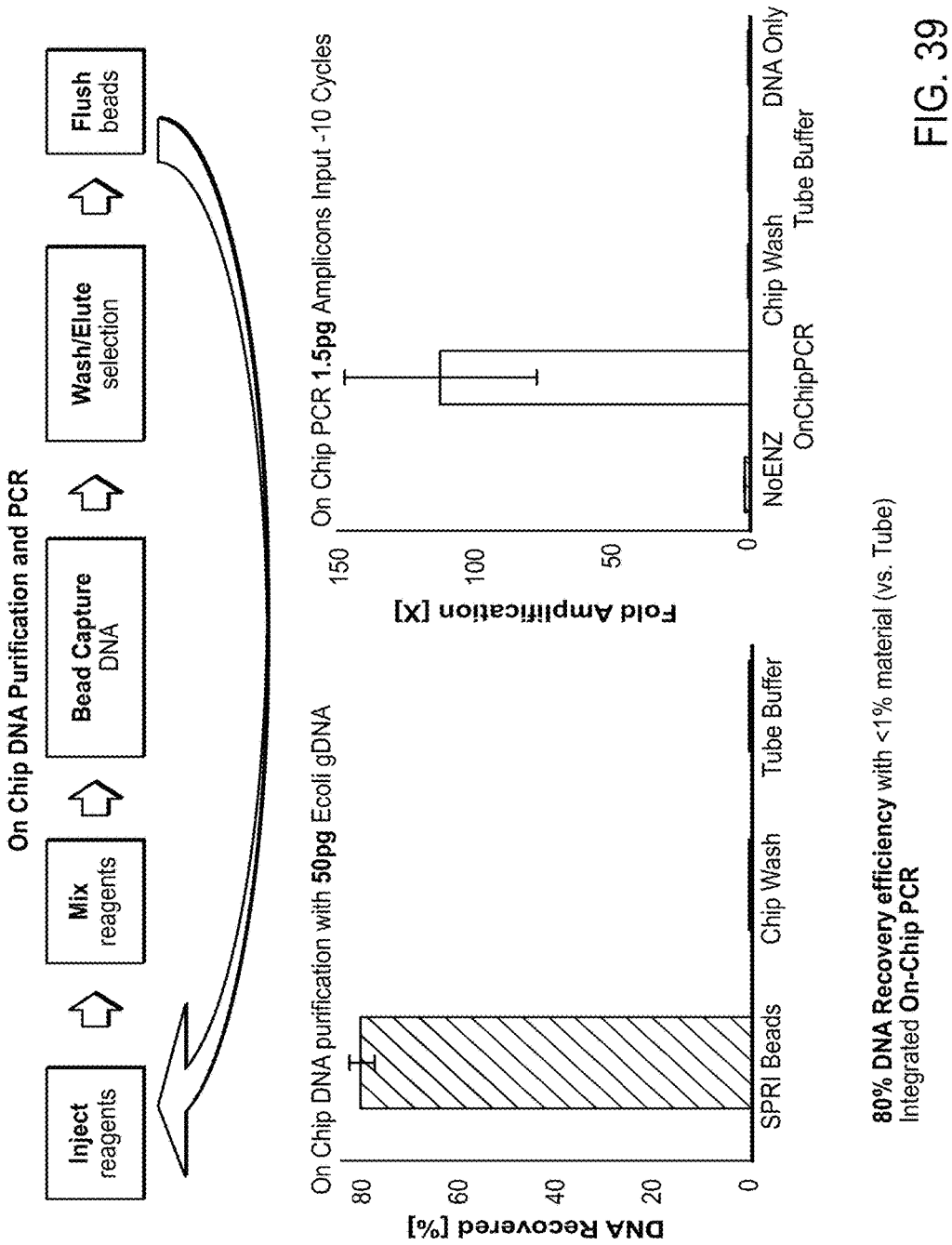
FIG. 39 is a graph depicting analysis of DNA purified on-chip and PCR using the DNA purified on-chip.

FIG. 39 depicts data from DNA purification and PCR performed on a microfluidic chip of the invention, using mixing and filtering operations. DNA purification was performed on the chip using Solid Phase Reversible Immobilization (SPRI) beads. DNA purification using SPRI involves (1) mixing reagents for the reaction, (2) capturing the molecule of interest with beads, (3) washing out the unwanted molecules and eluting the bound molecules for selection, then (4) flushing out the beads so that fresh beads can be used every time for high repeatability. The SPRI process on-chip does exactly this: beads are mixed with DNA, the DNA precipitates on to the surface of the beads, then the beads are filtered through specially patterned valves that hold the beads to wash and elute the DNA off the beads. High DNA purification efficiencies of 80% have been validated in the microfluidic chips, using 1% of the materials or reagents used for DNA purification in tubes.

Figure 40:
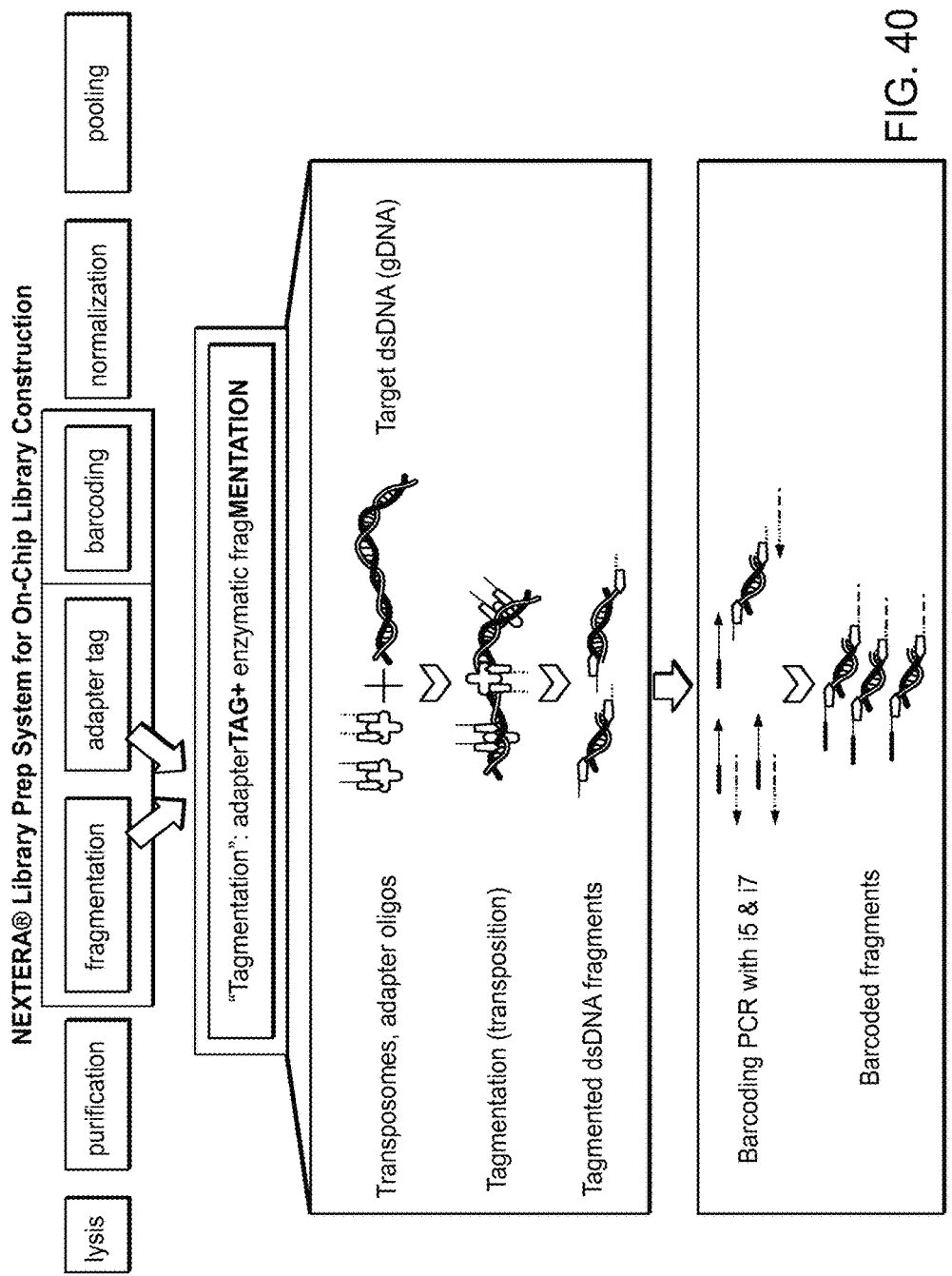
FIG. 40 depicts library construction on-chip using a library preparation system (e.g., NEXTERA®) to fragment and adapter tag the genomes.

FIG. 40 depicts library construction on-chip using a library preparation system (e.g., NEXTERA®) to fragment and adapter tag the genomes. This is an enzymatic fragmentation system that uses engineered Tn5 transposomes with adapter oligo transposons to simultaneously fragment and adapter tag the genomic DNA. The 'tagmented' fragments are barcoded by PCR with barcoding primers and loaded on to the sequencer.

Figure 41:
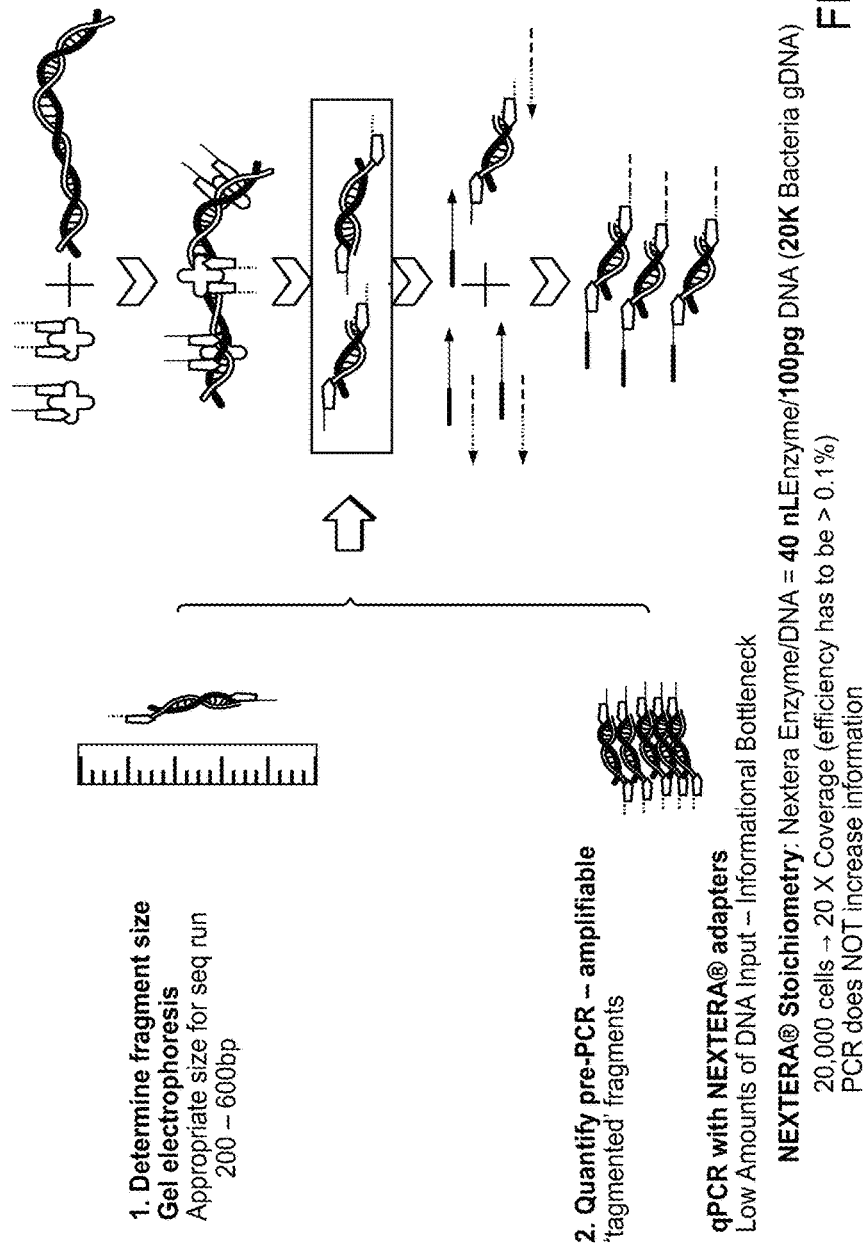
FIG. 41 depicts a protocol for quality check of on-chip library preparation using gel and/or qPCR analysis.

FIG. 41 depicts a protocol for quality check of on-chip library preparation. As mentioned above, the NEXTERA® library preparation process is used to 'tagment' genomic DNA. Before sequencing the DNA, a quality check of the processed libraries is performed before PCR amplification. The next generation sequencers need fragment size distribution between about 200 and about 600 base pairs. Fragment size distribution is verified on an agarose gel. Secondly, the PCR amplifiable fragments are quantified by qPCR using the NEXTERA® adapter sequence which was added during the NEXTERA® reaction. Basically, the conversion efficiency of the genomic DNA to the sequencing libraries is measured. In a tube reaction, this does not matter as much. Because the input DNA is large, there will be sufficient information even if the conversion efficiency is low (e.g., ~0.01%). However, this becomes more important when the reaction volumes are reduced. The NEXTERA® enzyme works only when a certain ratio is maintained. At 40 nL, the input is limited to 100 pg of DNA, which is around 20K bacterial genomes. The conversion efficiency should be at least 0.1% to get 20× coverage for high quality whole genome sequencing. The data shown herein include analysis of sequencing libraries generated from low amounts of purified genomic DNA using the microfluidic chip.

FIG. 42 depicts fragment size distribution for next generation sequencing (e.g., ILLUMINA®). Sequencing libraries were prepared from low amounts of purified genomic DNA using the microfluidic chip. To analyze the size distribution of the generated fragments, the fragments were run on a gel. The bottom image is an image of the gel and the top image is a plot of the fragments run on the gel in comparison to a 100 bp ladder. The samples run on the gel included 40 pg or 100 pg of purified *E. coli* or human gut microbiome genomic DNA that were processed in the microfluidic chip. The fragment sizes fell between about 200 to about 600 bp, which is optimal for loading on to the ILLUMINA® sequencers.

Figure 43:
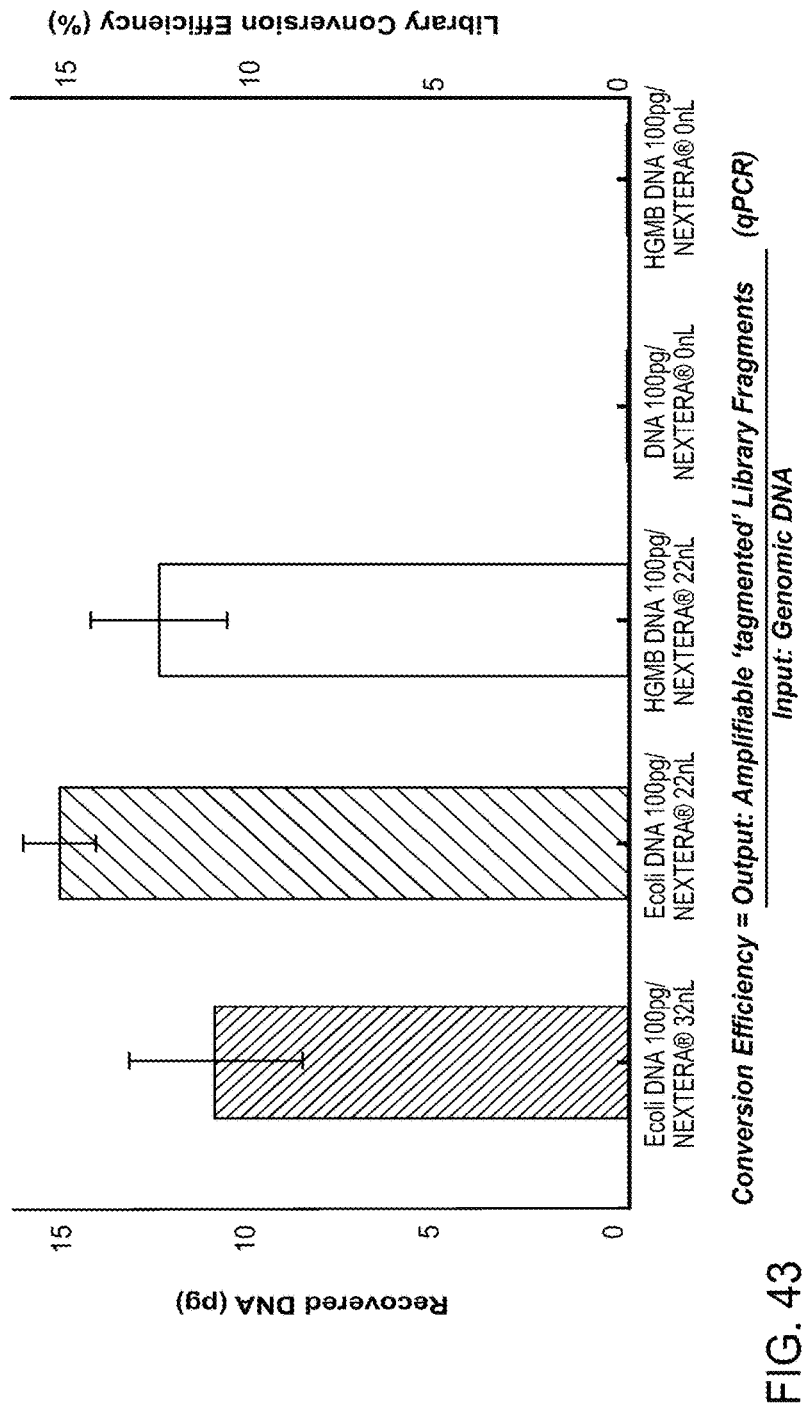
FIG. 43 is a graph depicting efficient library conversion for low input-high quality sequencing.

FIG. 43 depicts efficient library conversion for low input-high quality sequencing. The samples analyzed included the purified *E. coli* and human gut microbiome (HGMB) genomic DNA that were processed in the microfluidic chip. The output of the on-chip library preparation generates about 10 to about 15 pg of DNA. The DNA output is converted to library conversion efficiency by dividing the output, which is the amplifiable 'tagmented' library fragments, by the inputted genomic DNA amount. This yields about 5-15% library conversion efficiency, which shows that the SPRI is efficient with low sample quantity.

Figure 44:
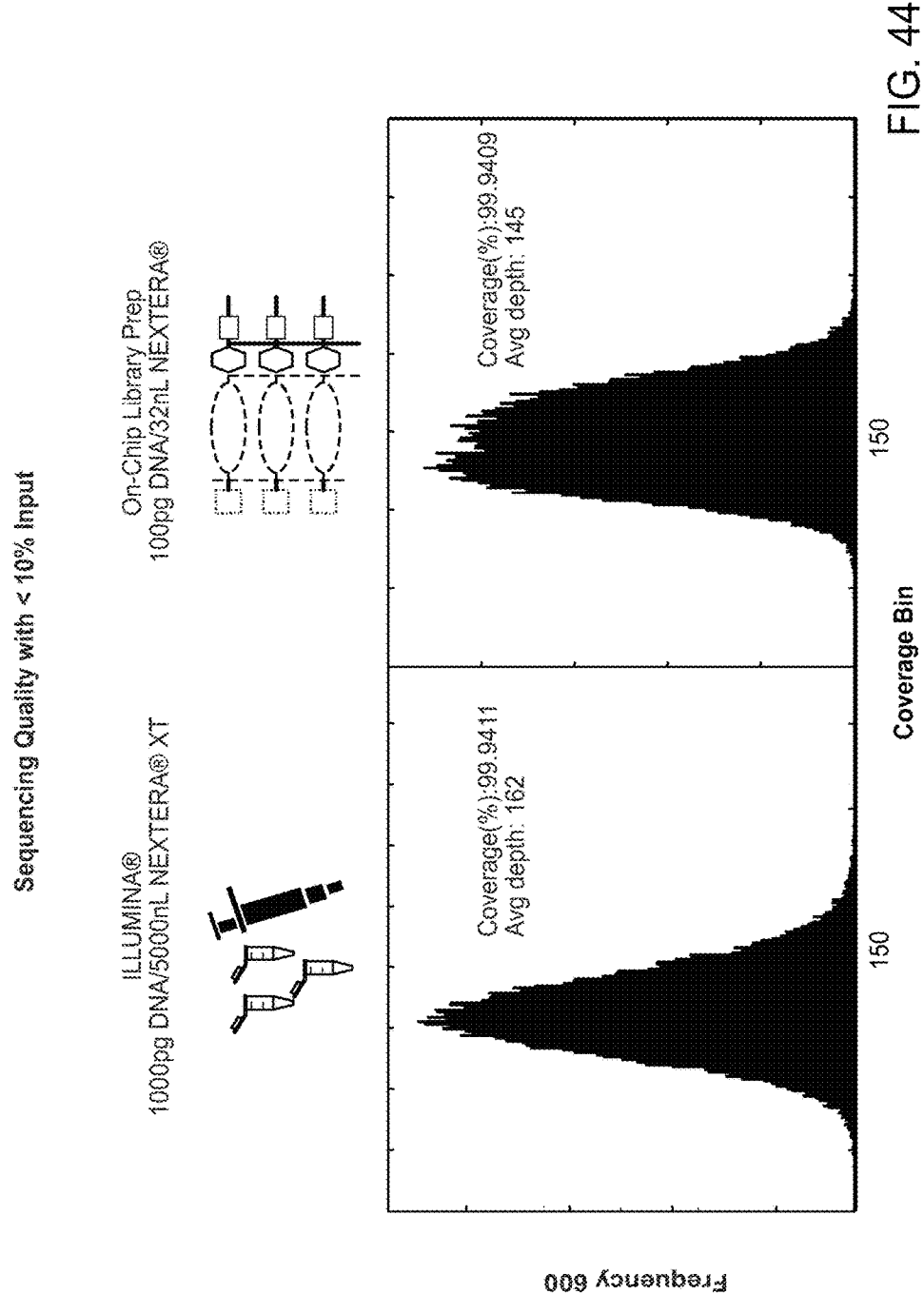
FIG. 44 depicts a comparison of sequencing quality with <10% input.

FIG. 44 depicts high sequencing quality was obtained using low input DNA obtained from on-chip preparation. Samples prepared on-chip were sequenced on a sequencer (MISEQ®) and compared with the published low-input NEXTERA® XT library preparation performed on the bench by Illumina. The ILLUMINA® reactions used 1000 pg of DNA and 5000 nanoliters of enzymes. Only a fraction of the inputs were used in the on-chip prepared samples, and excellent sequencing depth and coverage of the genome were achieved, which shows that the on-chip process is highly efficient.

Figure 45A:
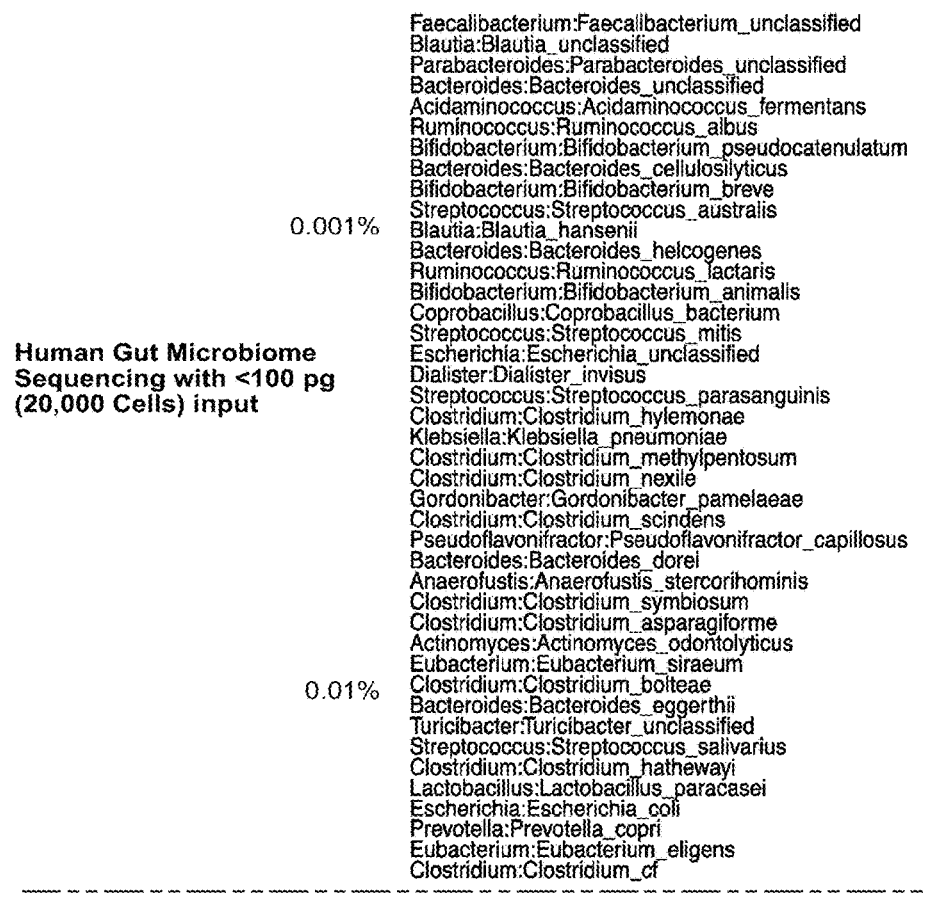

FIGS. 45A and 45B depicts a heat map of human gut microbiome generated from sequencing human gut microbiome sample prepared using the microfluidic chip. A library preparation was prepared from a human gut microbiome sample. This sample was previously analyzed by deep sequencing to determine the organisms in the population and is ordered by their relative abundances. A sample of about 44 to about 126 pg was processed in the microfluidic chip. The heat map represents the relative abundances of each organism obtained from sequencing DNA prepared on-chip in comparison to the known abundance. Darker color indicates over quantification, and lighter indicates under quantification. The data aligned well, up to 0.25%.

Figure 46:
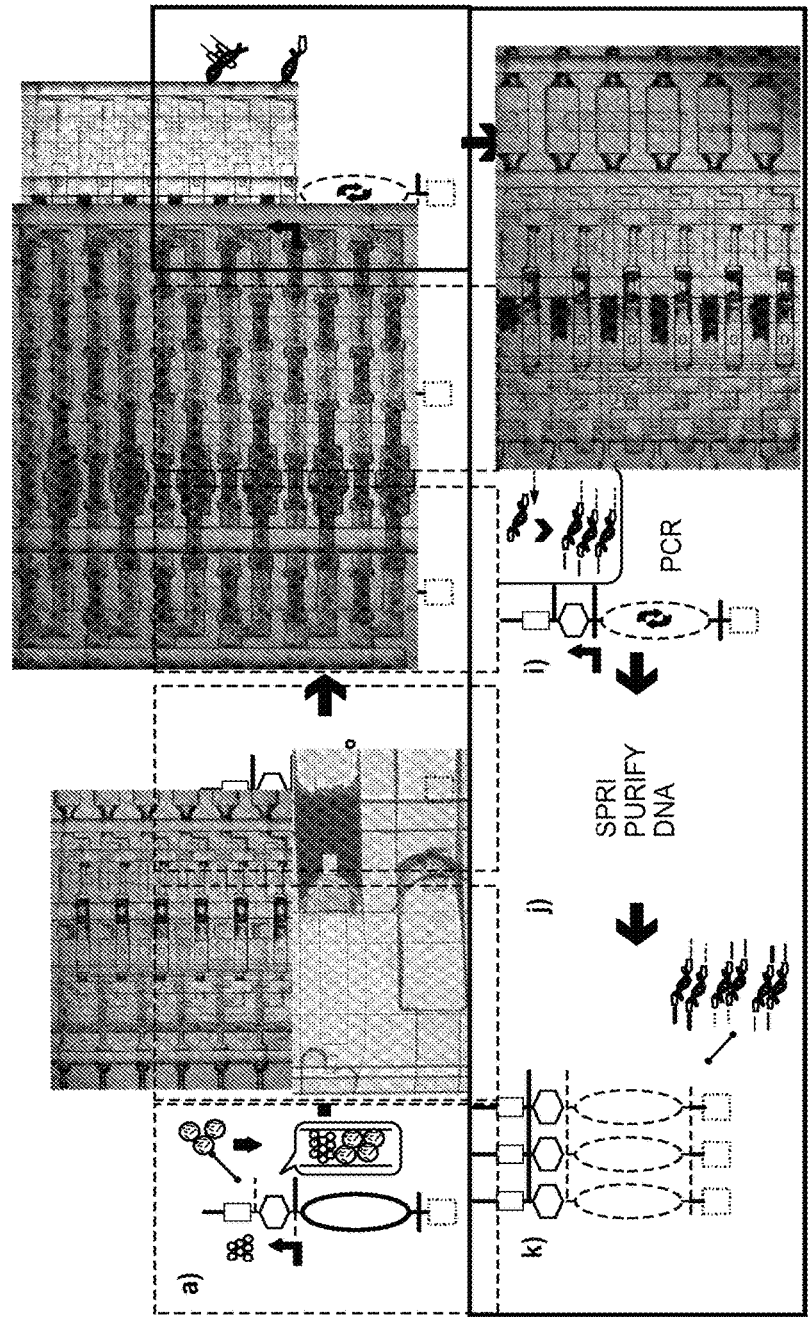
FIG. 46 depicts on-chip sample preparation from bacteria cells to sequencing libraries.

FIG. 46 depicts a schematic for full integration of sequencing sample prep from cells to sequencing library. The entire workflow was integrated on-chip for library preparation with bacteria cell capture, lysis, DNA purification, DNA fragmentation, fragment adapter tagging, and fragment barcoding. Microfluidic chip components are labeled where red indicates the reactor component and blue indicates the filter component. A brief overview of the entire sample prep process is depicted, which converts whole bacteria cells into sequence ready libraries, all in one device. First, a bead column is created by passing beads through filter valves to create the bead column. Then bacteria are passed through this column for capture. A solution of cells passing through the filter shows that the cells create a clear film of cells because they cannot pass. The cells are lysed by flushing the cells into the reactors with lysis buffer. The DNA from the lysed cells is captured by mixing the cell lysate with SPRI beads. The beads are then washed by filtering the DNA bound beads using the filter valves. The DNA bound SPRI beads is efficiently filtered. DNA is eluted into a holding tank by opening the holding tank and passing elution buffer through the DNA/SPRI bead column, which carries the DNA dissolved in it. Sequencing library preparation is prepared with the genomic DNA extracted from the cells. The barcoded libraries are collected to be sequenced.

Figure 47:
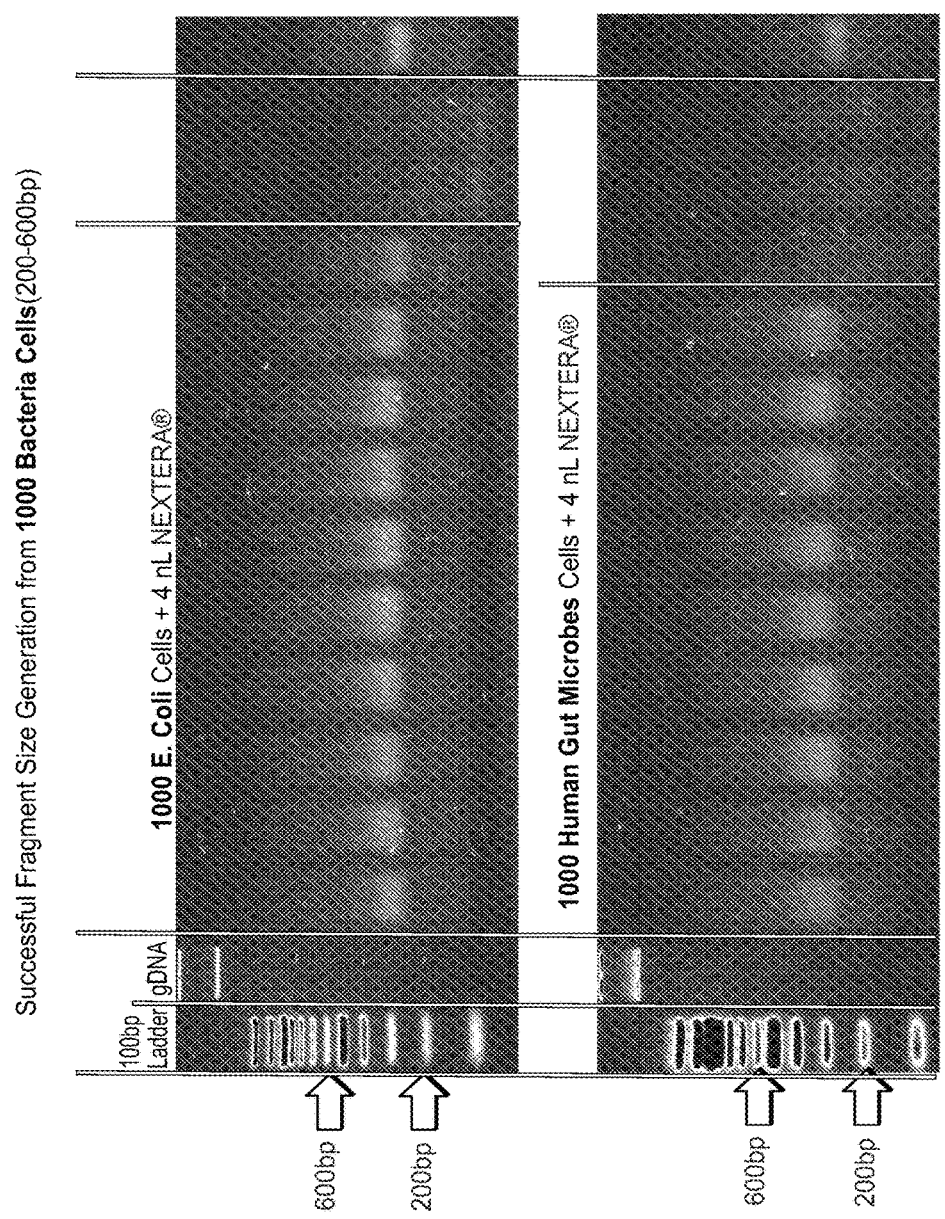
FIG. 47 depicts optimal fragment size generation (~200-~600 bp) using ~1000 E. coli cells.

FIG. 47 depicts a gel for quality checking of libraries made with about 16,000 bacteria cells (*E. coli* and human gut microbes). The sequencing libraries were made from 16,000 cells using 16 nL and 8 nL of NEXTERA® reagents. Note that the size of the fragments is optimal for sequencing (~200-~600 bp).

Figure 48:
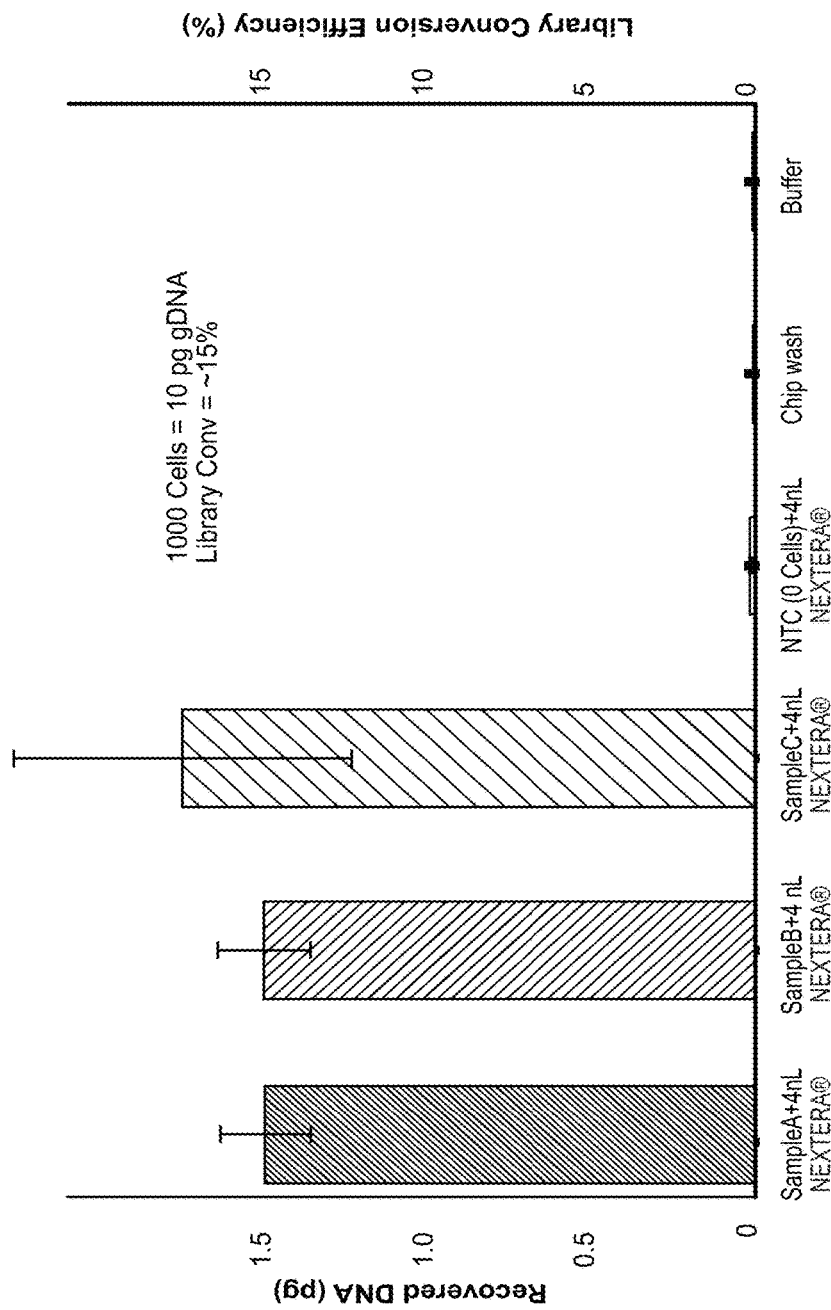
FIG. 48 depicts efficient library conversion using ~1000 E. coli cells.

FIG. 48 depicts quantification of the tagmented fragments using qPCR. Samples included 16,000 cells with 16 nL of NEXTERA® reagents, 8 nL of NEXTERA® reagents, and 0 nL of NEXTERA® reagents, and a no template control with 16 nL of NEXTERA® reagents. Starting from 16,000 cells yielded 10-15 pg of DNA, which indicates about a 15% library conversion efficiency at the end of the entire sample prep process in the microfluidic device.

Figure 49A:
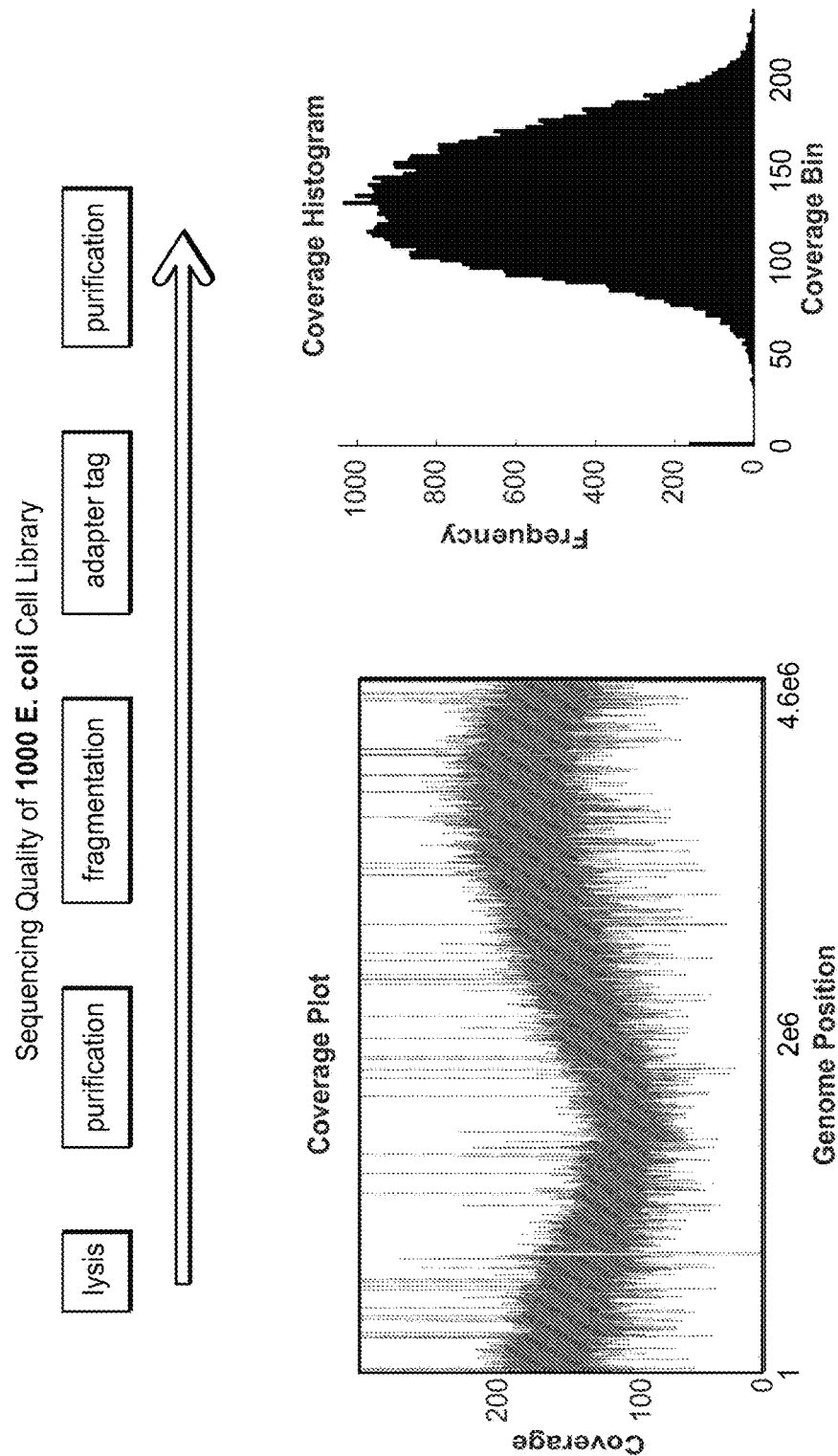
FIGS. 49A and 49B show sequencing quality of sample preparation using ~1000 E. coli cells.
Figure 49B:
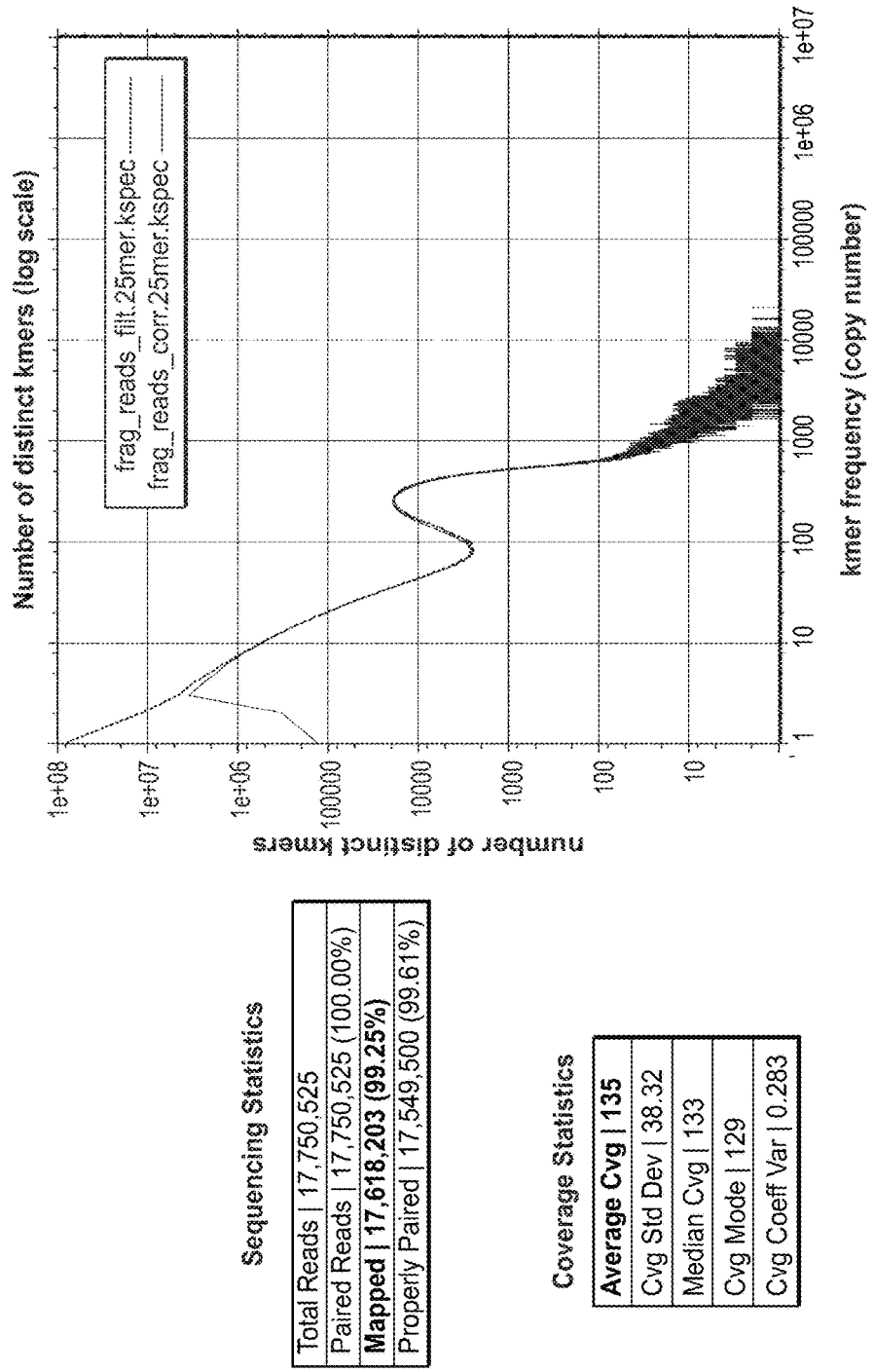

FIGS. 49A and 49B shows efficient sample preparation with ~1000 *E. coli* cells and the sequencing quality of the sequencing library. Coverage plot, coverage histogram, sequencing statistics, kmer plot, and coverage statistics are shown.

FIG. 50 is a chart showing the reduced cost of sequencing using the microfluidic chip. A breakdown of costs, including costs for labor and plastics, shows the feasibility of <$1 sequencing sample preparation. Minimizing labor through full automation and driving the reaction volumes by more than 100 fold, can reduce the cost to less than about $1/sample, e.g., processing cells to sequence libraries on the microfluidic chip. At this level, the reagent costs become so inexpensive that the pipette tip cost starts to become significant.

Integrating the sample preparation on the cell sorting chip allows tracking the evolutionary trajectory of single cells. In one embodiment of the microfluidic device (see e.g., FIG. 6), optical traps are used to sort the cells in the chip. A single bacterium can be targeted and moved around the channels of the chip. With the optical trap, single cells can be sorted, and sample prep reactors integrated in the ring are used to process their DNA.

Figure 55:
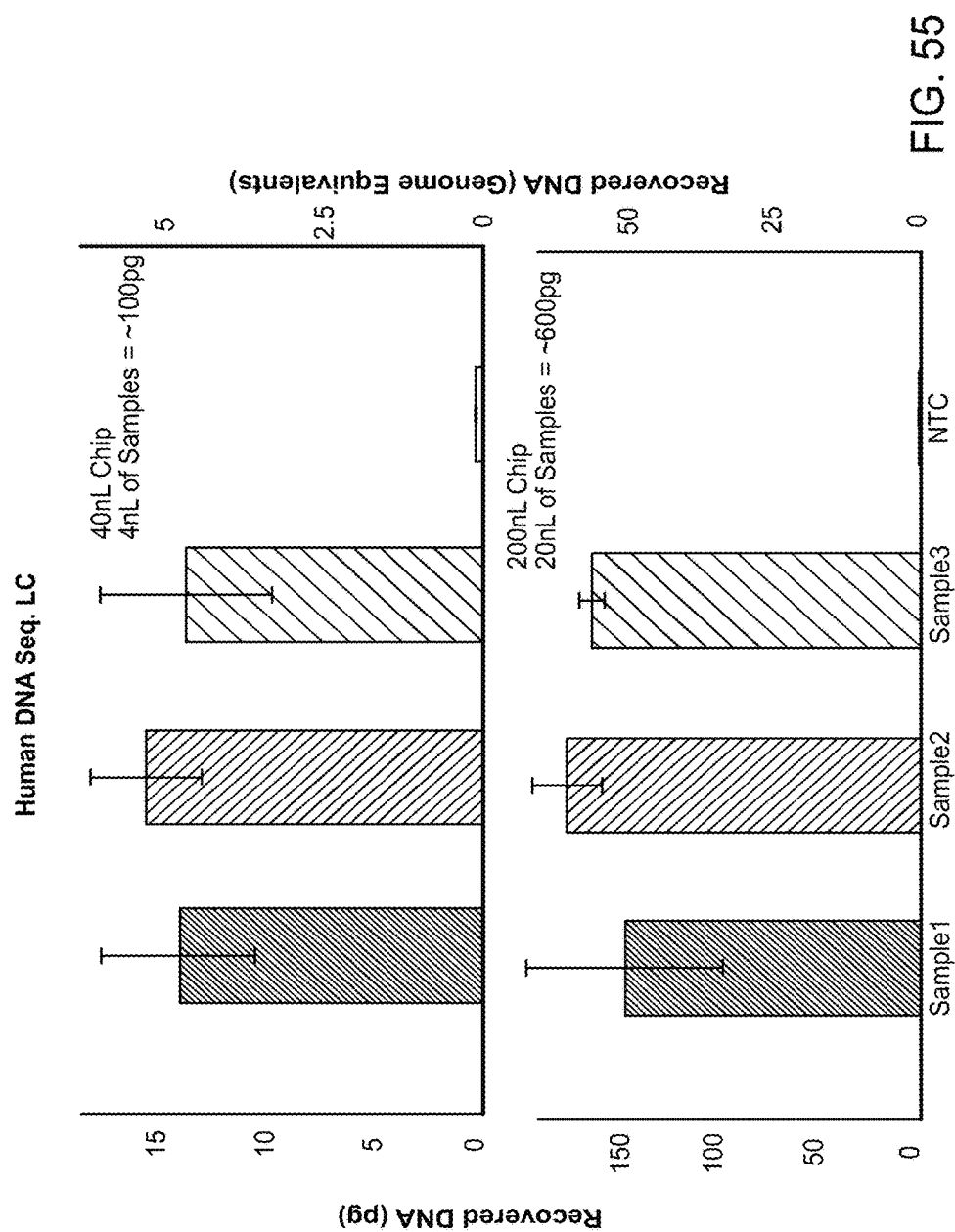
FIG. 55 depicts on chip recovery of human DNA for library conversion.

FIG. 55 are graphs depicting the amount of human genomic DNA recovered on a 40 nL chip is ~15 pg or ~5 genome equivalents and on 200 nL chips is ~150 pg or ~50 genome equivalents.

Figure 56:
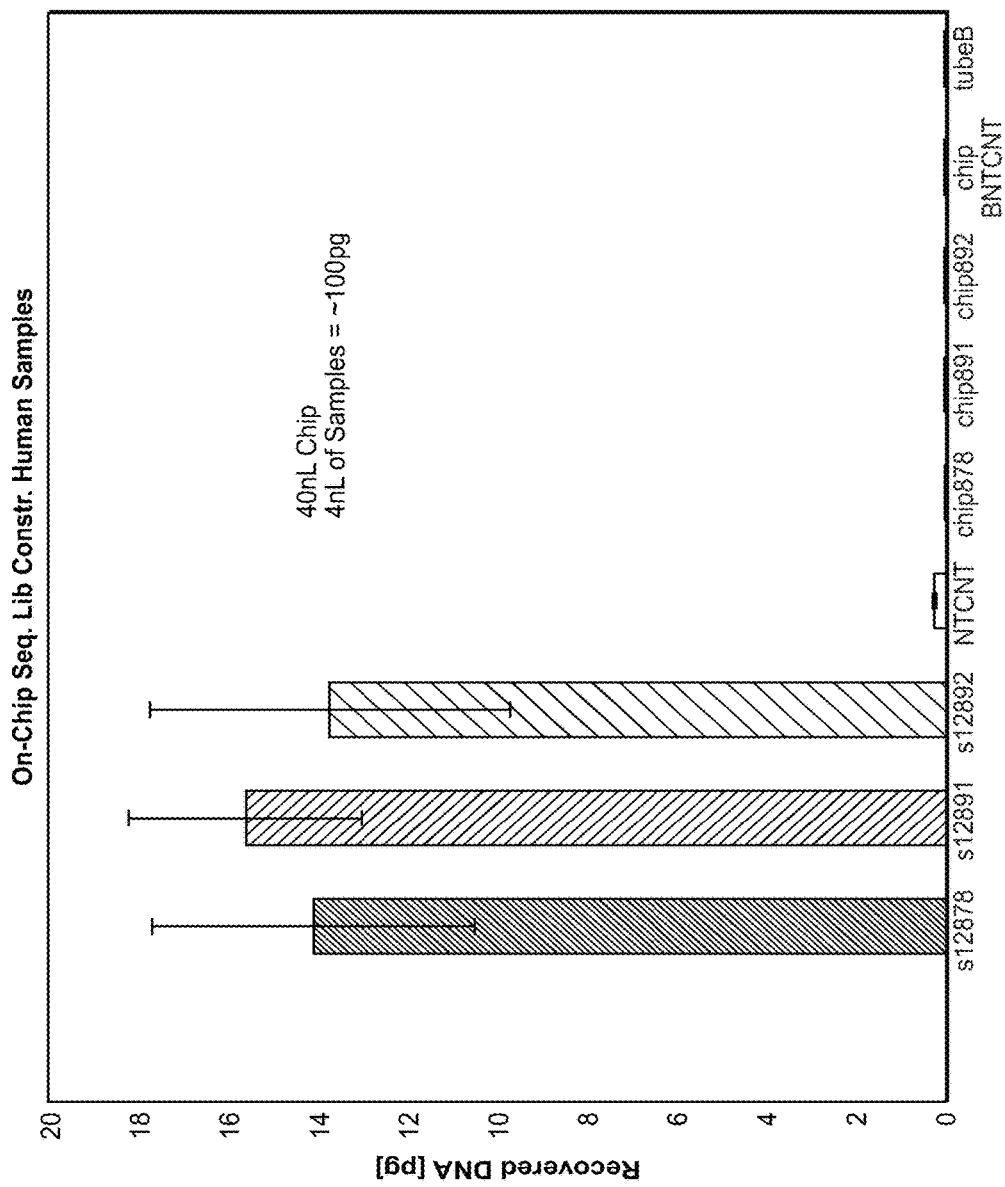
FIG. 56 depicts sequence library construction on a 40 nL chip with human samples.

FIG. 56 is a graph depicting the amount of genomic DNA recovered from human samples on a 40 nL chip is ~14-16 pg compared to controls.

Figure 57:
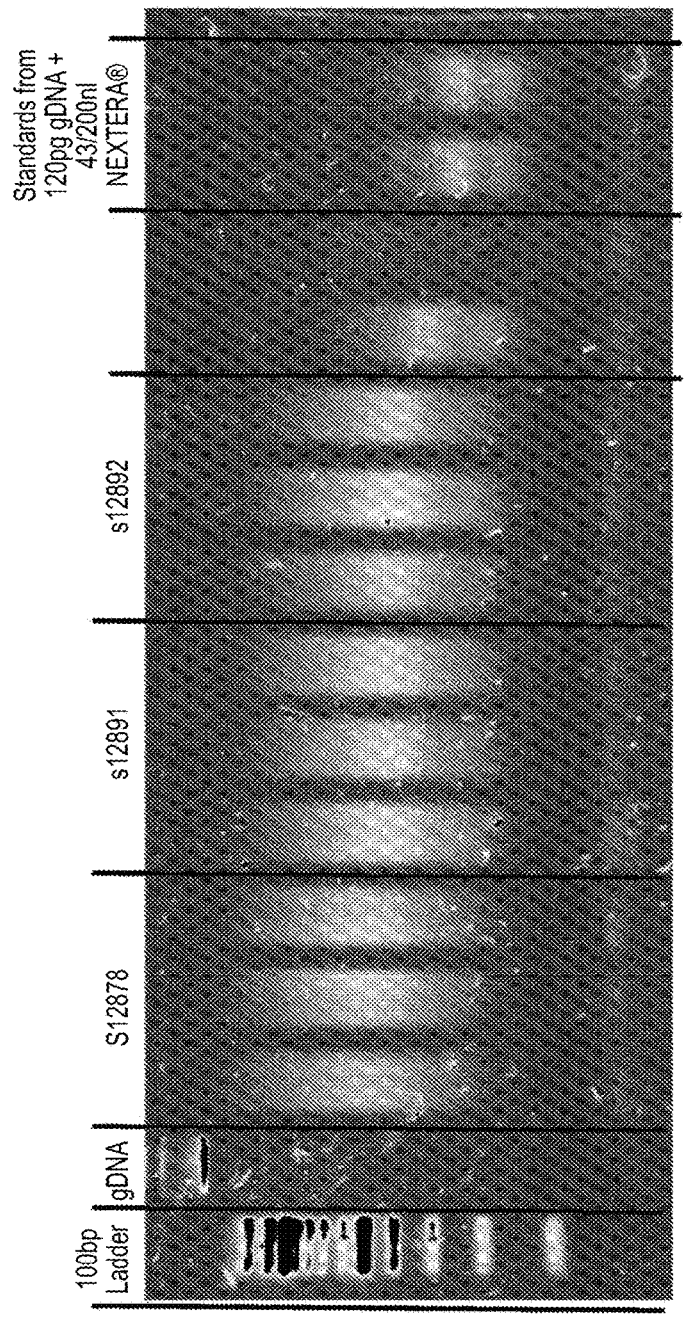
FIG. 57 depicts fragment size distribution of human genomic DNA in a 40 nL chip for next generation sequencing (e.g., ILLUMINA®)

FIG. 57 is depicts fragment size distribution of genomic DNA recovered from human samples on a 40 nL chip can be used for next generation sequencing (e.g., ILLUMINA®).

Figure 58:
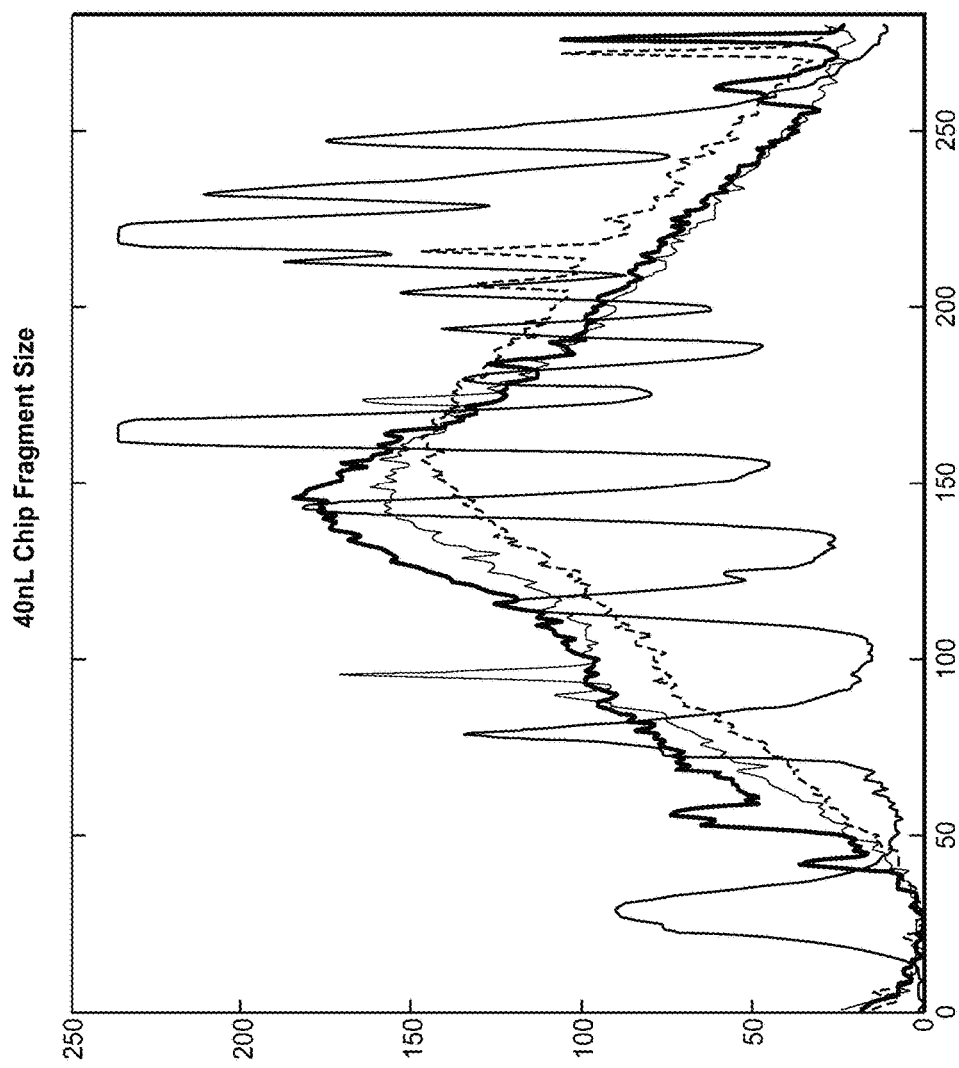
FIG. 58 is an analysis of fragment size distribution of human genomic DNA in a 40 nL chip.

FIG. 58 is an analysis of fragment size distribution of human genomic DNA recovered on a 40 nL chip.

Figure 59:
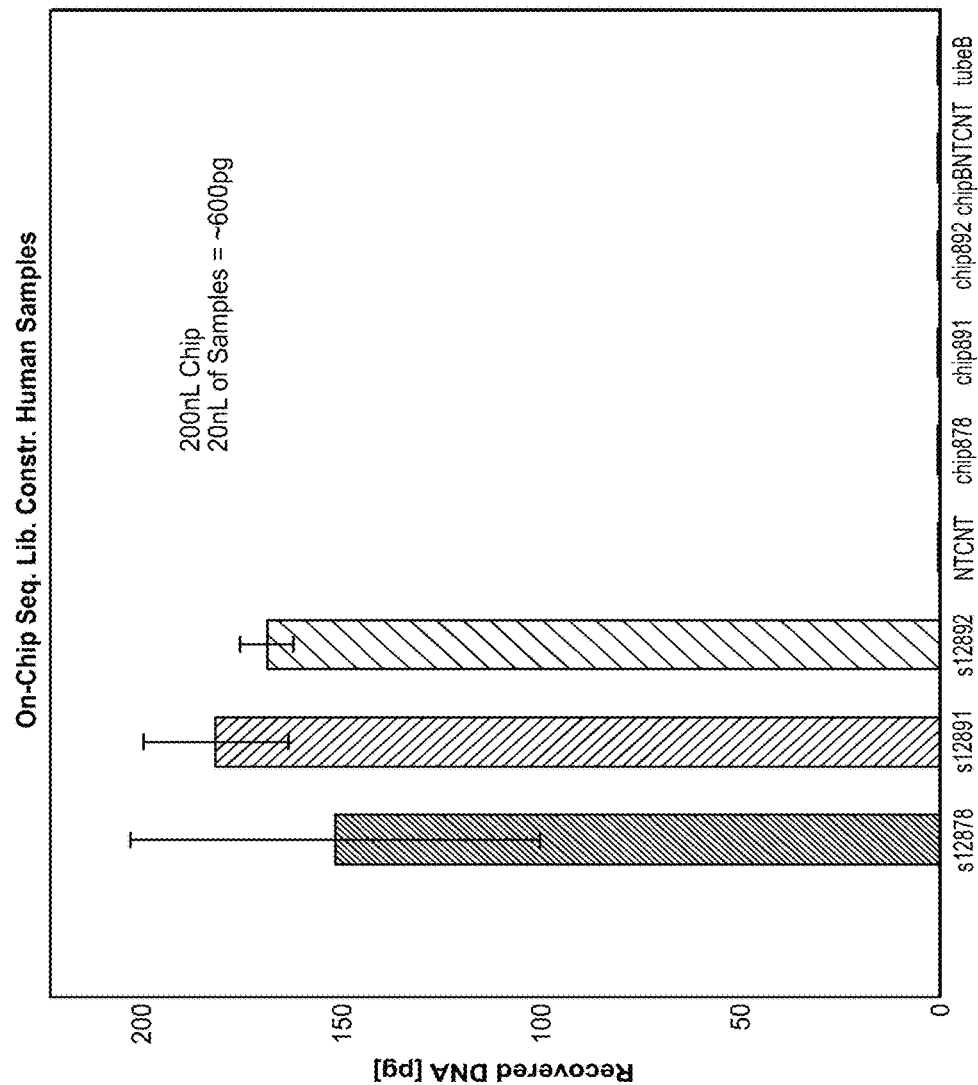
FIG. 59 depicts sequence library construction on a 200 nL chip with human samples.

FIG. 59 is a graph depicting the amount of genomic DNA recovered from human samples on a 200 nL chip is ~150-180 pg compared to controls.

Figure 60:
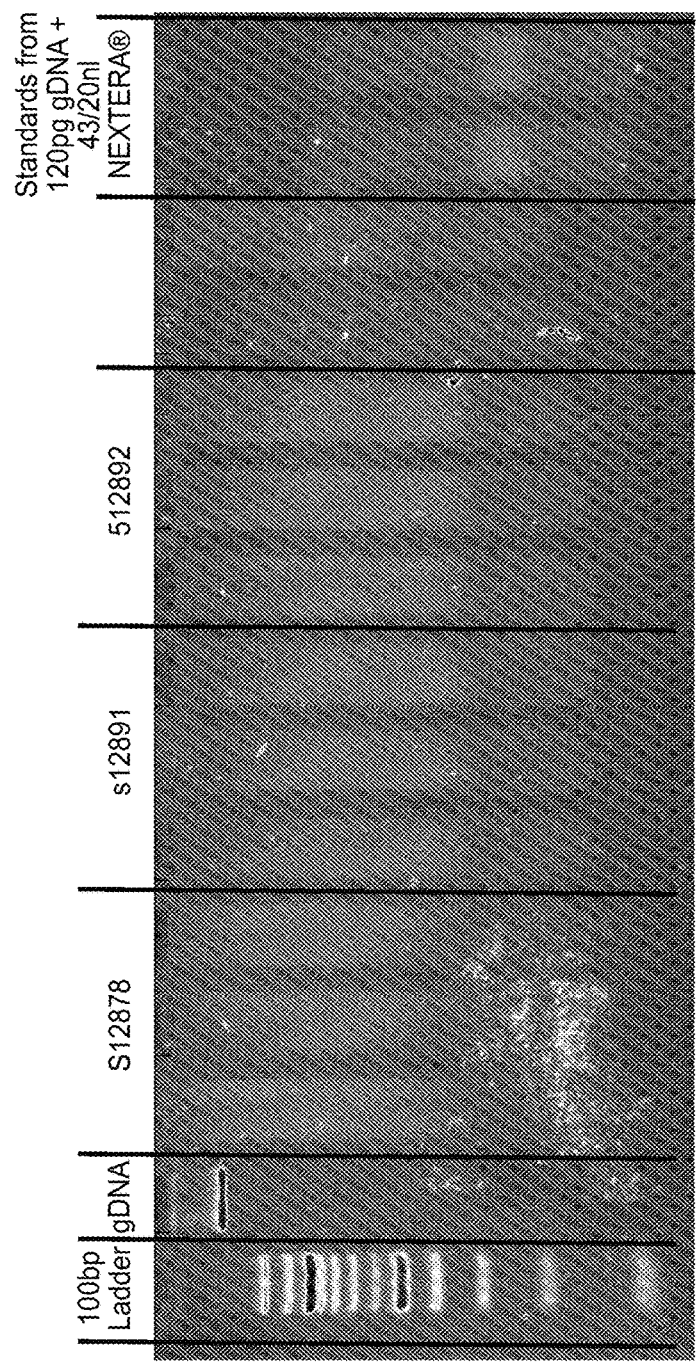
FIG. 60 depicts fragment size distribution of human genomic DNA obtained in a 200 nL chip.

FIG. 60 depicts fragment size distribution of human genomic DNA in a 200 nL chip.

Figure 61:
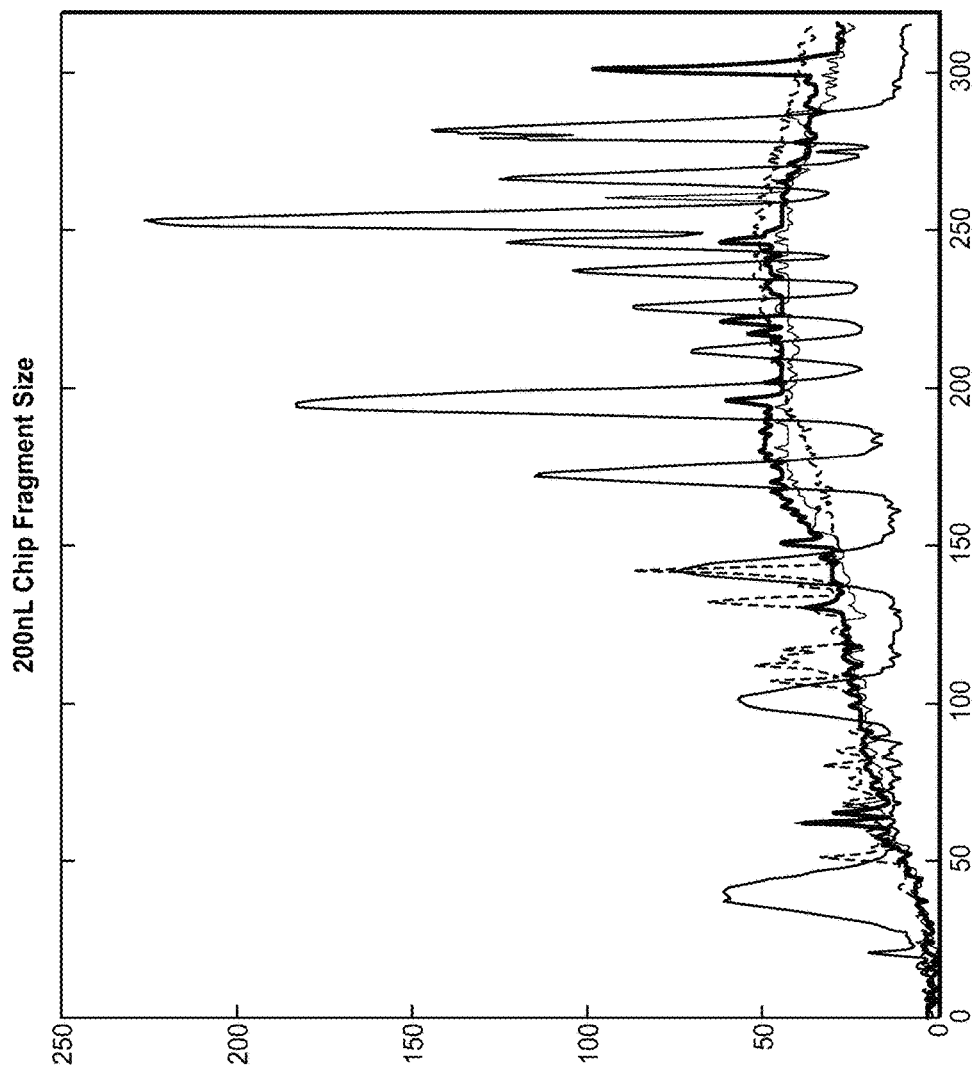
FIG. 61 is an analysis of fragment size distribution of human genomic DNA in a 200 nL chip.

FIG. 61 is an analysis of fragment size distribution of human genomic DNA obtained in a 200 nL chip.

FIG. 62 depicts fragment diversity and information complexity of human genomic DNA in sequencing library prepared on chip. The conversion efficiency is important because it provides a quantity of the amplifiable fragments of DNA, when starting from such low amounts. Approximately, 20× sequencing depth can be obtained even without amplifying the DNA fragments—which confirms that 100 pg DNA amounts are perfectly acceptable. The complexity of the reads and read numbers is about 20 genome equivalents from 20K cell input.

Figure 63:
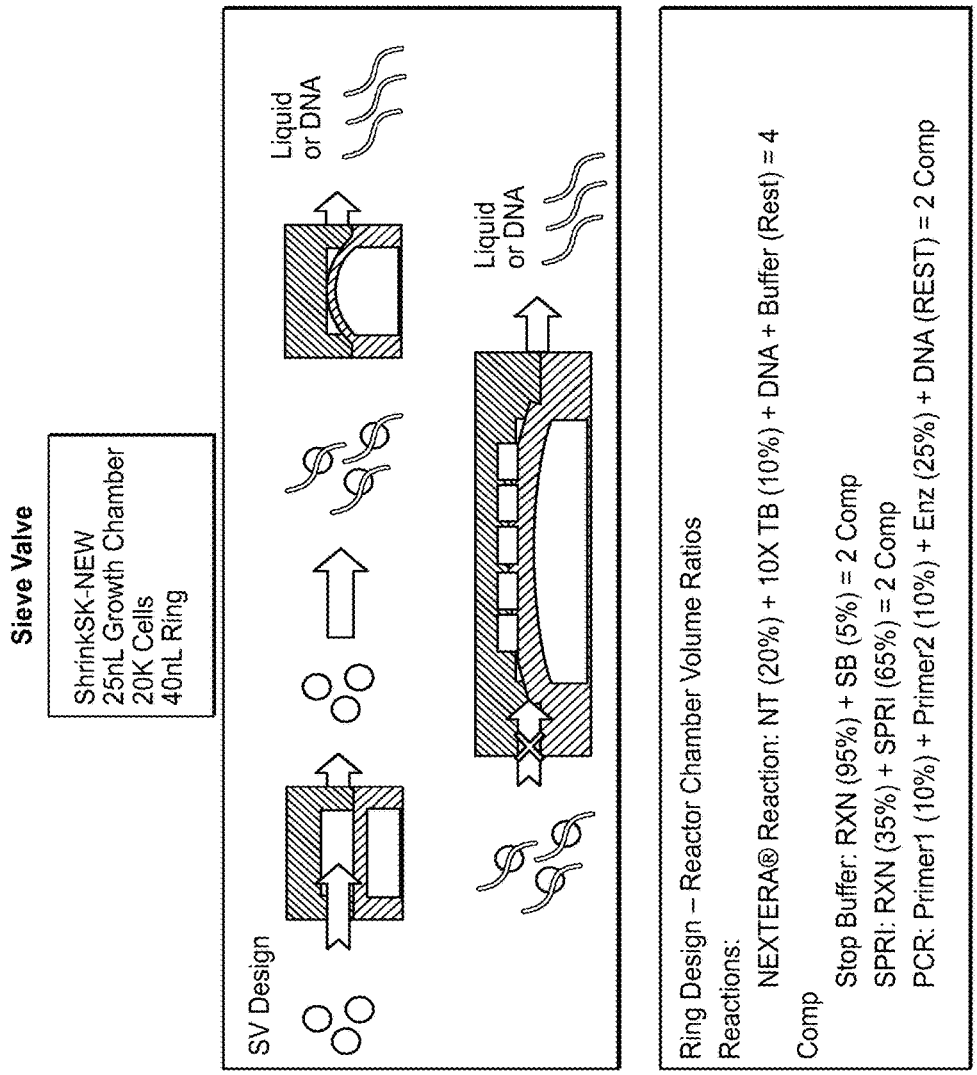
FIG. 63 depicts sieve valve design and use in biochemical reactions.

FIG. 63 depicts sieve valve design and use in biochemical reactions. The sieve valve can be used to filter particulate matter to process liquid or DNA. Reagents for various biochemical reactions are provided.

FIG. 64 is a graph depicting on chip reverse transcription and cDNA conversion (e.g., for preparation of sequencing library). On-chip reverse transcription and cDNA conversion was performed using Smart-Seq2 reagents. Validation of successful RT→cDNA was done by quantifying the relative amount of GAPDH gene present in the samples recovered from the chip after the RT/cDNA reaction using Smart-Seq2 reagents. The histogram bars are; a) No RNA, b) RNA only, c) all reagents, d) chip wash buffer collected to measure washing efficiency of the reactor walls, f) water only control.

FIG. 65 is a graph depicting on-chip RNA-seq library construction. On-chip RNA-sequencing library construction with Smart-Seq2 reagents. Validation of successful RT→cDNA→library construction with NEXTERA on-chip was done by quantifying the relative amounts of fragments that have the NEXTERA adapter sequence tagged. This quantification is done by performing qPCR on the samples recovered from the device after the entire on-chip Smart-Seq2 reaction, with PCR primers against the adapter sequence. The histogram bars are; a) RNA only, b) RNA only with NEXTERA enzymes, c) all reagents without NEXTERA enzymes, d) all reagents with NEXTERA enzymes, e) chip wash buffer collected to measure washing efficiency of the reactor walls, f) water only control.

Figure 66:
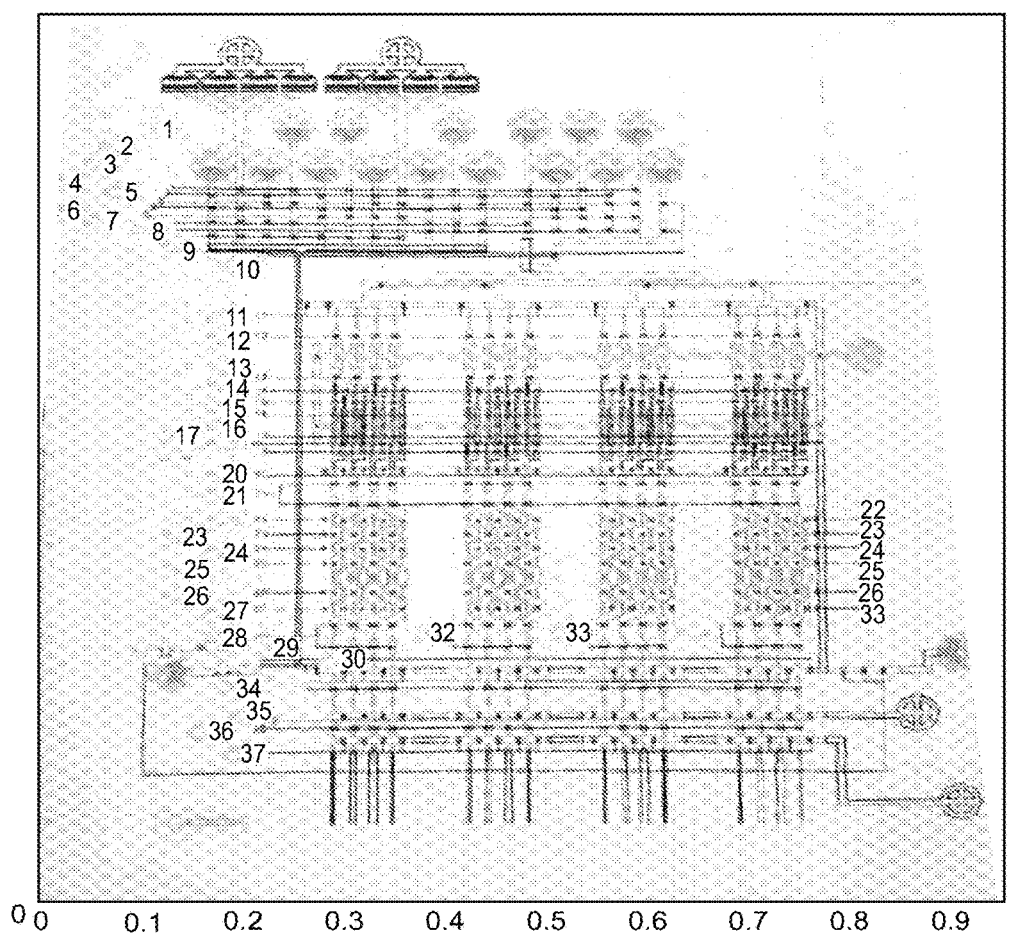
FIG. 66 depicts a microfluidic device for use in cell lysis and sequencing library preparation.

FIG. 66 depicts a microfluidic device used for cell lysis and sequencing library preparation performed entirely on chip; and The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the compositions of the invention, and are not intended to limit the scope of what the inventors regard as their invention.

EXAMPLES

Example 1. Polymerase Chain Reaction (PCR) on Chip

Polymerase chain reaction was performed using DNA amplicons (1.5 pg) from *E. coli* genomic DNA as input. The PCR reaction mix contained high concentration of BSA (1 mg/ml final concentration), 0.5 µM dNTP, 0.5 µM Primer1, 0.5 µM Primer2, 0.002 U of KAPA BIOSYSTEMS® HIFI™ DNA Polymerase suspended in a PCR reaction buffer (e.g., KAPA Biosystems high fidelity 1× Buffer). After 10 cycles of PCR in chip using 5° C. higher annealing temperature than the primer Tm (as advised by KAPA BIOSYSTEMS® protocol), amplification of product was obtained, about 100× fold (quantified by qPCR). Data showing on chip target specific PCR amplification are shown at FIG. 39.

Example 2. Cell Lysis and Library Conversion on Chip

A protocol combining cell lysis, nucleic acid isolation (e.g., DNA and/or RNA), and on chip library conversion is provided. Specifically, the protocol detailed below was used to obtain DNA from bacteria, which was used to generate sequencing library. The microfluidics device shown in FIG. 62 was used. The protocol can also be adapted to obtain RNA to generate sequencing library (e.g., DNase treatment). The protocol can also be adapted to purify nucleic acids from eukaryotic cells with modifications (e.g., higher channels>~15 µm, less harsh lysis conditions, etc.).

Buffer Preparation

Wash buffer: 10 mM Tris-HCl, 1% Tween20

Pre-treat buffer: 5% Tween20, 10 mM Tris-HCl pH 8.0, 1% KOLLIPHOR® 188 (Poly(ethylene glycol)-block-poly(propylene glycol)-block-poly(ethylene glycol); Sigma- Aldrich Catalog Number 15759), PLURONIC® F-127 (Sigma-Aldrich Catalog Number P2443)

Fragmentation Buffer: QIAGEN® P1 (e.g., 50 mM Tris-HCl pH 8.0, 10 mM EDTA, 100 μg/ml RNaseA)+0.5% Tween20+5% NP40+10 mM $CaCl_2$+3 mM $MgCl_2$ Binding Buffer: 4.3M NaCl, 33% PEG 8000, 1% Tween20

20× TB (Tag buffer): 200 mM Tris-HCl pH 8.0, 100 mM $MgCl_2$

Pre-Treat Chip

Flow pre-treat buffer into device and incubate for 1 Hour—treat all channels. Wash out the pre-treat buffer with wash buffer and dry.

I. Prep
  a. Thaw sample (e.g., human gut microbiome (HGMB)) →Dilute 5× to make 1000 cells/20 nL
  b. Make sieve valve (SV) beads with 2 μL DYNABEADS® M270-COOH+1 μL CML (carboxylate modified beads; 6 μm)+2 μL wash buffer II. Load
  a. Create bead column with SV beads
    i. Load Wash buffer first
    ii. Close top SV with 40 PSI
    iii. Prime with beads
    iv. Load until SV is ¾ packed
    v. Close bottom SV
    vi. Flush out with air (open end waste gate)
    vii. Close valve 20→close all waste gates→keep all SV closed
  b. Load cells
    i. Load cells into the holding tank
    ii. Close the top of the holding tank and flush out the prime with Wash buffer→air dry
  c. Filter cells
    i. Open top SV
    ii. Open bottom SV waste gate
    iii. Open bottom of the holding tank
    iv. Pump air Top to bottom
    v. Open top of the holding tank III. Fragmentation
  a. With valve 15 closed, wash the holding tank and all prime line Top to bottom then dry
  b. Make 0.05× (20× dilution) dsDNA fragmentase
    i. Add 1 μL dsDNA fragmentase+2 μL fresh 10×BSA in 17 μL of Fragmentation buffer
  c. Prime Top to bottom with Fragmentation buffer by washing channels with Fragmentation buffer
  d. Close all Ring channels inlets input from top and bottom
  e. Open Ring Top
  f. Add Fragmentation buffer through SV bead+cells (while SV closed) to 10% ring (vol.=~4 nl)
  g. Close valve 15
  h. Wash Top to bottom with wash buffer→dry
  i. Incubate chip 25 min@~37° C.→3 min@~75° C.→1 min@~4° C.

IV. Lysis
  a. Make Lysis buffer
    i. 0.5% 40% SDS+1 μL Proteinase K (20 mg/ml)+2 μL Mutanolysin (3 KU/ml)+2 μL Lysozyme (20 mg/ml)+14.5 μL Fragmentation buffer
  b. Prime Top to bottom by washing channels with Lysis buffer→dry→Lysis buffer
  c. Open 20% ring pushed (10% Ring Left+10% Ring Right) from left and right pushed in
  d. Open SV
  e. Add Lysis buffer
  f. Close valve 15
  g. Wash Top to bottom with wash buffer→dry
  h. Incubate chip 25 min@37° C.→30 min@56° C.→3 min@4° C.→1 min@4° C.
  i. Open 20% of the ring
  j. Flush with AIR
  k. Fill with wash buffer
  l. Wash Top to bottom with wash buffer→dry V. DNA purification
  a. Make SPRI (solid-phase reversible immobilization) Mix (4 μL M270+4 μL CML (carboxylate modified beads; 6 μm)→solution exchanged with 10 μL binding buffer
  b. Prime Bottom to top with SPRI Mix
    i. Open SPRI input channel for about 3 sec
    ii. Purge B with air (coat channels with SPRI)
    iii. Prime B with SPRI
    iv. Let equilibrate for about 20 seconds
  c. Inject into Ring
    i. Open all Ring Pump except valve 27
    ii. Open all Ring Bottom to top input
    iii. Pulse Ring Bottom to top and SPRI input to unclog
    iv. Once filled, mix about 1200 sec×2
  d. SV Beads+DNA
    i. Purge Bottom to top Dry with Air
    ii. Pressurize Bottom to top
    iii. Close SV top with 34 PSI
    iv. Open SV waste Top
    v. Open Ring Top to bottom→close some valves of the ring a few times to relieve pressure in the ring
    vi. Select Right RING Path
    vii. Pump AIR
    viii. Open ALL RING B
    ix. Wait until all is filtered
    x. Close ALL RING B
    xi. Switch to Left RING Path
    xii. Pump AIR
    xiii. Open ALL RING B
    xiv. Switch Left→Right Ring to filter all
    xv. Close all ring Bottom to top
    xvi. Close SV waste Top
  e. Alcohol Wash
    i. Prime line with Alcohol (e.g., ethanol)
    ii. Select Right Ring path
    iii. Open all ring Bottom to top
    iv. Wait to fill ethanol (ETOH)
    v. Open SV waste Top—pulse for about 10 sec+
    vi. Close SV waste top
    vii. Switch to Left Ring path
    viii. Wait to fill ETOH
    ix. Open SV waste Top—Pulse for about 10 sec+
    x. Close SV waste top
    xi. Close All Ring Bottom to top
    xii. Purge Bottom to top with AIR
    xiii. Pressurize Bottom to top
    xiv. Open SV waste Top
    xv. Open Ring Top to bottom→close some valves of the ring a few times to relieve pressure in the ring
    xvi. Select Right RING Path
    xvii. Pump AIR
    xviii. Open ALL RING Bottom to top
    xix. Wait until all is filtered
    xx. Close ALL RING Bottom to top
    xxi. Switch to Left RING Path
    xxii. Pump AIR
    xxiii. Open ALL RING Bottom to top
    xxiv. Switch Left→Right to filter all
    xxv. Close all ring Bottom to top xxvi. Close SV waste Top
xxvii. Repeat×2
f. Elute
  i. Prime Bottom to top with wash buffer
  ii. Select Right Ring Path
  iii. Open Ring Bottom to top
  iv. Wait to fill
  v. Open holding tank Bottom to top—Pulse over about 2 min
  vi. Close holding tank Bottom to top
g. Wash out Ring
  i. Open SV Top
  ii. Pulse oven SV waste top
  iii. Pulse for about 10 sec
  iv. Close SV waste top
  v. Switch to Left Ring Path
  vi. Pulse oven SV waste top
  vii. Pulse for about 10 sec
  viii. Close SV Waste top
  ix. Close Ring Bottom to top
  x. Open SV waste top
  xi. Select Right Ring path
  xii. Purge Bottom to top with AIR
  xiii. Pump AIR
  xiv. Open ALL RING Bottom to top
  xv. Wait until all is filtered
  xvi. Close ALL RING Bottom to top
  xvii. Switch to Left RING Path
  xviii. Pump AIR
  xix. Open ALL RING B
  xx. Switch Left→Right to filter all
  xxi. Close all ring Bottom to top
  xxii. Close SV waste Top
VI. NEXTERA®
a. Make 10× TB (1 μL CML+9 μL wash buffer+10 μL 20× TB)
b. Close all ring pumps
c. Prime Bottom to top with 10× TB
d. Open all Ring Bottom to top
e. Close all Ring Bottom to top
f. Prime Bottom to top with NT (NEXTERA® enzyme—tn5 from Illumina)
g. Open appropriate section for NT loading
h. Open Ring Bottom to top (appropriate reps)
i. Close all Ring Bottom to top
j. Prime Bottom to top with wash buffer
k. Open+10% of Ring
l. Open all Ring Bottom to top
m. Close all Ring Bottom to top
n. Open all Ring except for valve 27
o. Fill Top to bottom with wash buffer
p. Open holding tank Bottom to top
q. Open holding tank Top to bottom
VII. DNA purification
VIII. Extract DNA from chip through bottom I/O port with pipette tips (collect 3-5 μL).

Example 3: Microfluidic Library Construction

Figure 67A:
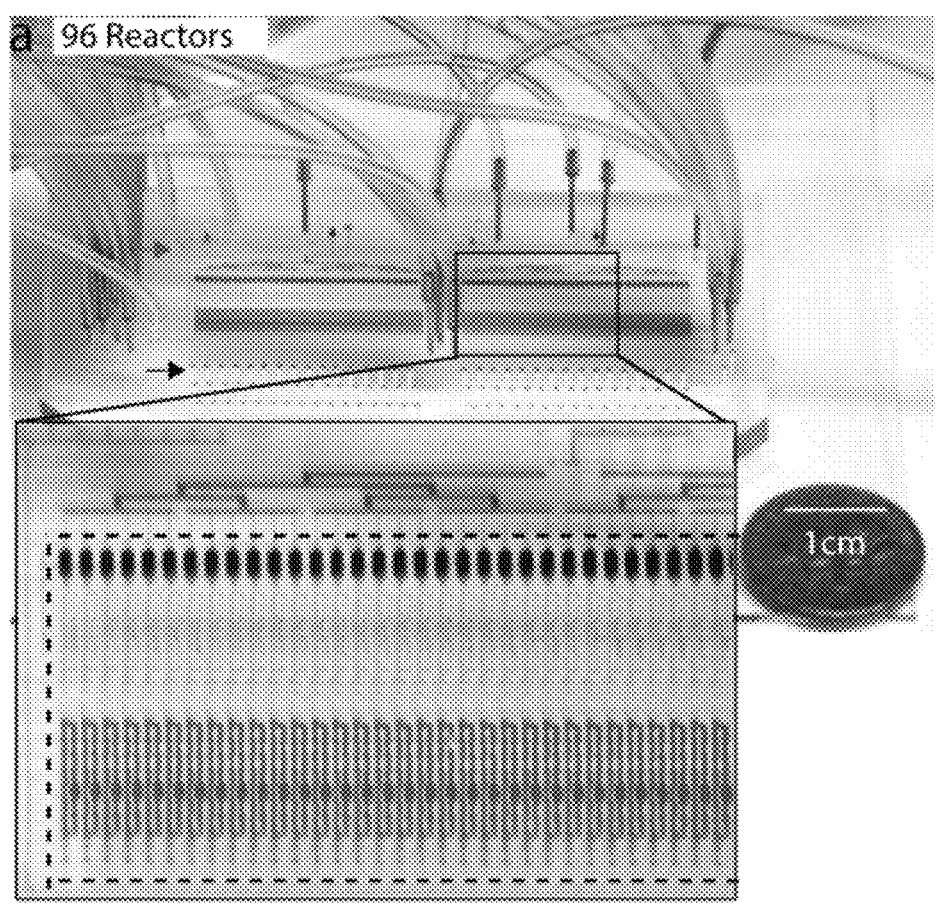
FIGS. 67A-67F depict a library construction device, operation, and performance.
Figure 67B:
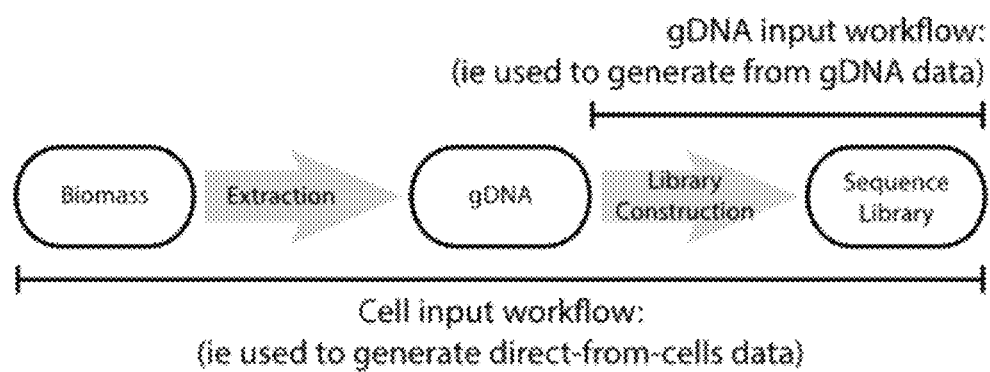
Figure 67C:
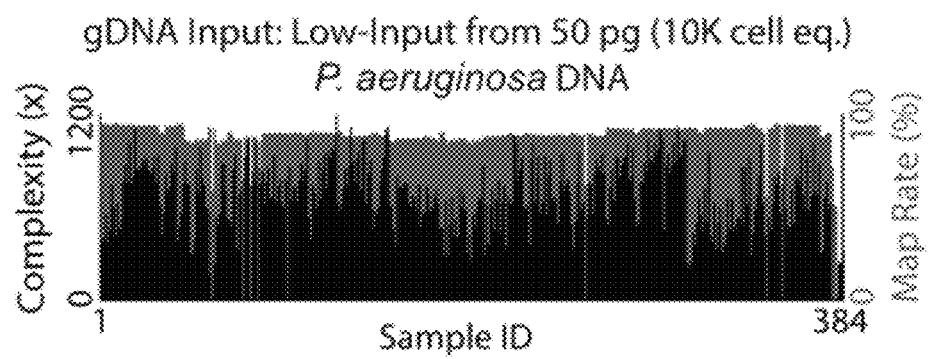

The microfluidic library construction device described herein was used to carry out on-device cell lysis and library construction for *P. aeruginosa*, *E. coli*, *M. tuberculosis*, and soil bacteria using the protocol described Examples 1 and 2. FIG. 67A provides a photograph of the 96×36 nL microfluidic library construction device and FIG. 67B is a schematic diagram that describes a microfluidic sample preparation workflow. FIG. 67C shows the estimated complexity and mapping rate to the *P. aeruginosa* PA14 reference genome for the clinical *P. aeruginosa* isolate DNA. In this case, the input to the device was gDNA.

Figure 67D:
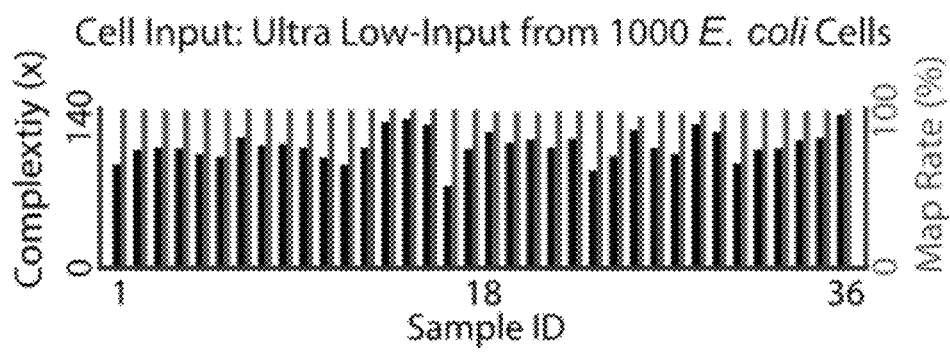

FIG. 67D shows the sequencing statistics for low input *E. coli* processed with the microfluidic library construction device. The *E. coli* mapping rate is that mapped to the reference *E. coli* BL21-DE3. For each of FIGS. 67D, E, and F, the library complexity was calculated using Picard tools (http://broadinstitute.github.io/picard/) and the human DNA read fraction was determined using deconseq (http://deconseq.sourceforge.net/).

Figure 67E:
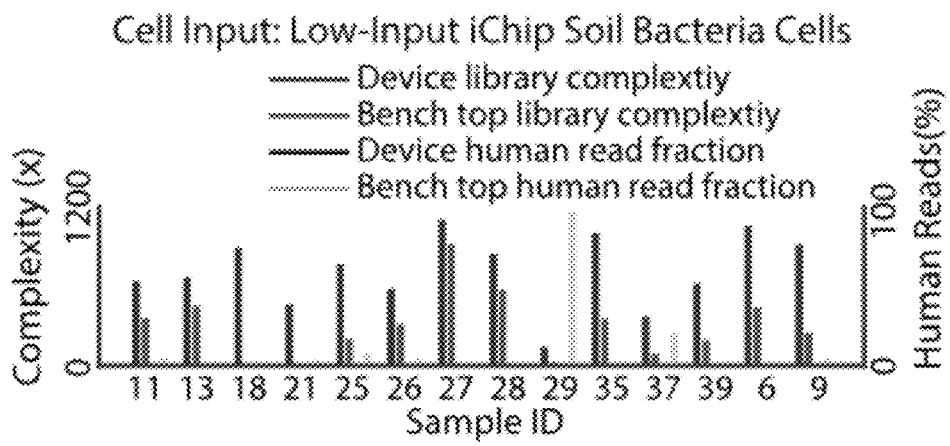

FIG. 67E shows the sequencing statistics for low input soil microbes processed with the device. The table below shows the assembly statistics of soil bacteria processed in the microfluidic library construction device versus a library processed using a conventional "bench-top" approach (i.e., that does not involve the use of a microfluidic device). The tables below provide statistics relevant to the performance of the device in constructing genome assemblies.

Genome assemblies are composed of scaffolds and contigs. Contigs are contiguous consensus sequences that are derived from collections of overlapping reads. Scaffolds are ordered and orientated sets of contigs that are linked to one another by mate pairs of sequencing reads. A contig N50 is calculated by first ordering every contig by length from longest to shortest. Next, starting from the longest contig, the lengths of each contig are summed, until this running sum equals one-half of the total length of all contigs in the assembly. The contig N50 of the assembly is the length of the shortest contig in this list.

| samples\metrics | N50(bp) | Largest Contig (bp) | Total Length (bp) | GC (%) |
|---|---|---|---|---|
| Device | | | | |
| CD6 | 347052 | 1152193 | 6544117 | 59.04 |
| CD9 | 308741 | 571008 | 6444770 | 60.45 |
| CD11 | 209156 | 510820 | 6496978 | 59.41 |
| CD13 | 339367 | 911230 | 6692556 | 59.64 |
| CD18 | 293004 | 850614 | 6427234 | 61.27 |
| CD21 | 209156 | 544659 | 6487866 | 59.41 |
| CD25 | 382109 | 825690 | 6749403 | 59.72 |
| CD26 | 524500 | 980681 | 7308890 | 66.23 |
| CD27 | 319334 | 910854 | 6679790 | 59.64 |
| CD28 | 368255 | 617459 | 6432614 | 59.07 |
| CD29 | 4202 | 46516 | 7725873 | 55.59 |
| CD35 | 372180 | 889133 | 6751657 | 59.73 |
| CD37 | 246728 | 825257 | 6759393 | 59.72 |
| CD39 | 181716 | 564849 | 5091447 | 56.44 |
| Bench | | | | |
| CT6 | 302895 | 1152180 | 6539354 | 59.04 |
| CT9 | 305129 | 571008 | 6452957 | 60.44 |
| CT11 | 261511 | 548268 | 6511807 | 59.38 |
| CT13 | 338637 | 910762 | 6681370 | 59.64 |
| CT18 | NA | NA | NA | NA |
| CT21 | 1304 | 1955 | 8179 | 55.12 |
| CT25 | 244961 | 889480 | 6745410 | 59.72 |
| CT26 | 522807 | 1297641 | 7313190 | 66.22 |
| CT27 | 294494 | 654165 | 6684891 | 59.65 |
| CT28 | 344743 | 857050 | 6444123 | 59.05 |
| CT29 | 6803 | 29888 | 5279588 | 54.99 |
| CT35 | 357841 | 889693 | 6747895 | 59.73 |
| CT37 | 171699 | 439443 | 6742929 | 59.71 |
| CT39 | 72149 | 197665 | 5075245 | 56.45 |

Table legend:
GC% refers to guanine-cytosine content.

Figure 67F:
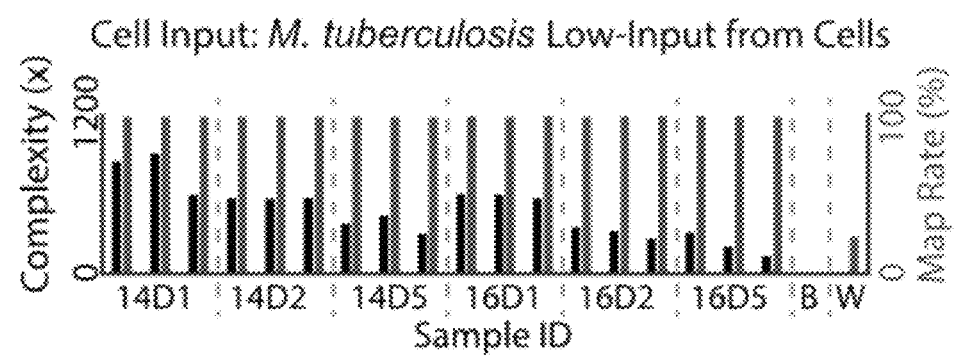

FIG. 67F shows the sequencing statistics for low input *M. tuberculosis* cells processed with the device. The *M. tuberculosis* reads were mapped to the *M. tuberculosis* OFXR-14 reference genome.

EQUIVALENTS

Those skilled in the art will recognize, or be able to ascertain using no more than routine experimentation, many equivalents of the specific embodiments of the invention described herein. Such equivalents are intended to be encompassed by the following claims.

From the foregoing description, it will be apparent that variations and modifications may be made to the invention described herein to adopt it to various usages and conditions. Such embodiments are also within the scope of the following claims.

For example, the methods described herein can be implemented as object code or machine code stored on non-transitory, tangible computer-readable media for execution by a general-purpose or a special-purpose computer. For example, the methods can be implemented by a device that is adapted, configured, and/or programmed to fluidically interface with a microfluidic structure as described herein. Such devices include the IFC Controller RX available from Fluidigm Corporation of South San Francisco, Calif.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of isolating an analyte, the method comprising:
   (i) loading a sample into a holding chamber of a microfluidic circuit, wherein the microfluidic circuit comprises:
      one or more holding chambers in fluid communication with an input valve;
      a mixing circuit comprising a plurality of chambers in fluid communication with the one or more holding chambers, wherein the one or more holding chambers and/or the mixing circuit comprises a capture substrate for capturing and isolating the analyte or component;
      one or more sieve valves positioned between the holding chamber and the mixing circuit and positioned in at least partial fluid communication with one or more of the plurality of chambers of the mixing circuit, and
      one or more sieve valves positioned in at least partial fluid communication with one or more of the plurality of the chambers of the mixing circuit,
      wherein each of the one or more sieve valves includes:
      a substrate defining a channel;
      a flexible membrane adapted and configured for deployment at an intersection with the channel; wherein one or more protrusions extends into the channel from the substrate and is situated opposite the flexible membrane, the one or more protrusions defining a plurality of recesses extending beyond the intersection between the channel and the flexible membrane; and
      an output valve;
   (ii) passing the sample into the mixing circuit;
   (iii) capturing the analyte on the capture substrate in the mixing circuit;
   (iv) washing the capture substrate to remove uncaptured components; and
   (v) releasing the analyte from the capture substrate.

2. The method of claim 1, wherein the capture substrate is loaded into the microfluidic circuit, the holding chamber, and/or the mixing circuit.

3. The method of claim 1, wherein the capture substrate comprises a bead, microbead, surface of the microfluidic circuit, or a capture reagent.

4. The method of claim 1, wherein the microfluidic circuit is contained in a microfluidic device.

5. The method of claim 4, wherein the microfluidic device comprises a plurality of microfluidic circuits which lie in a plurality of laminar layers of the microfluidic device.

6. The method of claim 5, wherein the plurality of microfluidic circuits of the microfluidic device span across a plurality of laminar layers of the microfluidic device.

7. The method of claim 1, further comprising opening at least one of the sieve valves to remove the capture substrate from the microfluidic circuit, the holding chamber, and/or the mixing circuit.

8. The method of claim 1, wherein the method further comprises:
   activating the sieve valve positioned between the holding chamber and the mixing circuit in order to retain the capture substrate and the sample within the holding chamber while permitting fluid to pass through the sieve valve.

9. The method of claim 3, wherein the capture reagent comprises an antibody, carboxylic acid, cation, anion, cationic group, anionic group, hydrophobic group, magnetic material, protein, ligand, nucleic acid, affinity agent, or a combination thereof.

10. The method of claim 1, wherein the sample comprises one or more of a single cell, a plurality of cells, a tissue, an organelle, a particle, an organism, a virus, a microorganism, a spore, a fungus, a nucleic acid molecule, a polypeptide, a carbohydrate, a lipid, or a small molecule.

11. The method of claim 10, wherein the sample comprises a prokaryotic cell, a eukaryotic cell, or a plurality thereof.

12. The method of claim 1, wherein the analyte comprises one or more of a nucleic acid molecule, polypeptide, carbohydrate, lipid, or small molecule.

13. The method of claim 1, further comprising:
   loading one or more reagents for modifying the analyte in the microfluidic circuit;
   mixing the one or more reagents and the analyte in the mixing circuit to modify the analyte; and
   removing the modified analyte from the microfluidic circuit.

14. The method of claim 13, wherein the modifying comprises fixing a label, reporter, nucleic acid molecule, polypeptide, or synthetic molecule to the analyte.

15. The method of claim 13, wherein the analyte is a nucleic acid molecule and the method comprises:
   loading one or more reagents for fragmenting the nucleic acid molecule in the microfluidic circuit;
   mixing the one or more reagents and the nucleic acid molecule in the mixing circuit to fragment the nucleic acid molecule;
   removing the nucleic acid fragments from the microfluidic circuit; and optionally, fixing an amplification adaptor to the 5' and 3' ends of the nucleic acid fragments.

16. The method of claim 15, further comprising:
contacting the nucleic acid fragments with primers that hybridize to the amplification adaptors inside the mixing circuit; and
amplifying the nucleic acid fragments inside the mixing circuit.

17. The method of claim 16, wherein the amplifying comprises polymerase chain reaction (PCR) amplification, helicase-dependent amplification (HAD), nicking enzyme amplification reaction (NEAR), loop mediated isothermal amplification (LAMP), rolling circle amplification (RCA), or recombinase polymerase amplification (RPA).

18. The method of claim 17, wherein the nucleic acid fragments provide a sequence library pool of individual samples having a coefficient of variation (COV) of 0.5 or less in their respective quantities.

19. A method of isolating an analyte, the method comprising:
(i) loading a sample into a holding chamber of a microfluidic circuit, wherein the microfluidic circuit comprises:
one or more holding chambers;
a mixing circuit comprising a plurality of chambers in fluid communication with the one or more holding chambers, wherein the one or more holding chambers and/or the mixing circuit comprises a capture substrate for capturing and isolating the analyte or component;
one or more sieve valves positioned between the holding chamber and the mixing circuit and positioned in at least partial fluid communication with one or more of the plurality of chambers of the mixing circuit;
one or more sieve valves positioned in at least partial fluid communication with one or more of the plurality of the chambers of the mixing circuit;
wherein each of the one or more sieve valves includes:
a substrate defining a channel;
a flexible membrane adapted and configured for deployment at an intersection with the channel; wherein
one or more protrusions extends into the channel from the substrate and is situated opposite the flexible membrane, the one or more protrusions defining a plurality of recesses extending beyond the intersection between the channel and the flexible membrane; and
an output valve;
(ii) passing the sample into the mixing circuit;
(iii) capturing the analyte on the capture substrate in the mixing circuit;
(iv) washing the capture substrate to remove uncaptured components; and
(v) releasing the analyte from the capture substrate.

* * * * *